US010314906B2

(12) United States Patent
Ogembo et al.

(10) Patent No.: US 10,314,906 B2
(45) Date of Patent: Jun. 11, 2019

(54) VIRUS-LIKE PARTICLE COMPOSITIONS AND VACCINES AGAINST EPSTEIN-BARR VIRUS INFECTION AND DISEASE

(71) Applicant: THE UNIVERSITY OF MASSACHUSETTS, Boston, MA (US)

(72) Inventors: Javier Gordon Ogembo, North Grafton, MA (US); Trudy Morrison, Northborough, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 15/558,942

(22) PCT Filed: Mar. 16, 2016

(86) PCT No.: PCT/US2016/022663
§ 371 (c)(1),
(2) Date: Sep. 15, 2017

(87) PCT Pub. No.: WO2016/149384
PCT Pub. Date: Sep. 22, 2016

(65) Prior Publication Data
US 2018/0078634 A1    Mar. 22, 2018

Related U.S. Application Data

(60) Provisional application No. 62/134,785, filed on Mar. 18, 2015.

(51) Int. Cl.
| | |
|---|---|
| *A61K 39/245* | (2006.01) |
| *A61K 39/17* | (2006.01) |
| *A61K 39/12* | (2006.01) |
| *C12N 7/00* | (2006.01) |
| *G01N 33/574* | (2006.01) |
| *A61K 39/00* | (2006.01) |

(52) U.S. Cl.
CPC ............ *A61K 39/245* (2013.01); *A61K 39/12* (2013.01); *C12N 7/00* (2013.01); *G01N 33/574* (2013.01); *A61K 2039/5256* (2013.01); *A61K 2039/5258* (2013.01); *A61K 2039/575* (2013.01); *A61K 2039/585* (2013.01); *A61K 2039/70* (2013.01); *C12N 2710/16222* (2013.01); *C12N 2710/16223* (2013.01); *C12N 2710/16234* (2013.01); *C12N 2710/16271* (2013.01); *C12N 2710/20022* (2013.01); *C12N 2710/20023* (2013.01); *C12N 2710/20034* (2013.01); *C12N 2710/20071* (2013.01); *C12N 2760/18122* (2013.01); *C12N 2760/18123* (2013.01); *C12N 2760/18134* (2013.01); *C12N 2760/18171* (2013.01); *G01N 2333/05* (2013.01)

(58) Field of Classification Search
None
See application file for complete search history.

(56) References Cited

U.S. PATENT DOCUMENTS

| | | | |
|---|---|---|---|
| 7,951,384 B2 | 5/2011 | Morrison et al. | 424/214.1 |
| 8,974,797 B2 | 3/2015 | Morrison | 424/193.1 |
| 2009/0252761 A1 | 10/2009 | Frazer et al. | 424/204.1 |
| 2014/0227305 A1 | 8/2014 | Lange-Ruiss et al. | 424/186.1 |

FOREIGN PATENT DOCUMENTS

WO    WO/2014/018858    1/1914

OTHER PUBLICATIONS

Pantua et al. Requirements for the Assembly and Release of Newcastle Disease Virus-Like Particles. J. Virol. 2006, 80: 11062-11073.*
Adhikary, D. et al. (2008) "Standardized and Highly Efficient Expansion of Epstein-Barr Virus-Specific CD4(+) T Cells by Using Virus-Like Particles," *Journal of Virology* 82(8), 3903-3911.
Apcher, S. et al. (2010) "Epstein Barr Virus-Encoded EBNA1 Interference with MHC Class I Antigen Presentation Reveals a Close Correlation between mRNA Translation Initiation and Antigen Presentation," *PLoS Pathogens* 6(10), e1001151.
Babcock, G. J. et al. (1998) "EBV Persistence in Memory B Cells In Vivo," *Immunity* 9(3), 395-404.
Balfour, H. H. (2014) "Progress, Prospects, and Problems in Epstein-Barr Virus Vaccine Development," *Current opinion in virology* 0, 1-5.
Battisti, A. J. et al. (2012) "Structure and assembly of a paramyxovirus matrix protein," *Proceedings of the National Academy of Sciences of the United States of America* 109(35), 13996-14000.

(Continued)

*Primary Examiner* — Nianxiang Zou
(74) *Attorney, Agent, or Firm* — Medlen & Carroll, LLP

(57) ABSTRACT

The present inavcation relates to prophylactic and/or therapeutic vaccines thatpoatairj Newcastle disease Virus (NDV) virus-like particles (VLPs) comprising one or more Epstein-Barr Virus (EBV) antigens, in one embodiment, the invention provides a recombinant virus-like particle (V'UP) comprising, i is operable combination, a) Newcastle disease virusA iNDVj matrix (M) protein, and b) one or more Epstein-Barr Virus (BBV) antigens. The im'eniion's prophylactic and/or therapeutic vacclrses are useful for preventing asc/or treatmg, infection with EBY aixi/or disease associated Epstein-Barr Virus, such as cancer.

23 Claims, 89 Drawing Sheets

(56) References Cited

OTHER PUBLICATIONS

Biggar, R. J. et al. (1978) "Primary epstein-barr virus infections in African infants. II. Clinical and serological observations during seroconversion," *International Journal of Cancer* 22(3), 244-250.

Biggar, R. J. et al. (1978) "Primary epstein-barr virus infections in african infants. I. Decline of maternal antibodies and time of infection," *International Journal of Cancer* 22(3), 239-243.

Biggin, M. et al. (1987) "Epstein-Barr virus gene expression in P3HR1-superinfected Raji cells," *Journal of Virology* 61(10), 3120-3132.

Borza, C. M. et al. (2002) "Alternate replication in B cells and epithelial cells switches tropism of Epstein-Barr virus," *Nature Medicine* 8, 594.

Braciale, T. J. et al. (1987) "Antigen Presentation Pathways to Class I and Class II MHC-Restricted T Lymphocytes," *Immunological Reviews* 98(1), 95-114.

Chatterjee, B. et al. (2014) "Animal models of Epstein Barr virus infection," *Journal of Immunological Methods* 410(Supplement C), 80-87.

Chesnokova, L. S. et al. (2011) "Fusion of Epstein-Barr Virus with Epithelial Cells Can Be Triggered by αvβ5 in Addition to αvβ6 and αvβ8, and Integrin Binding Triggers a Conformational Change in Glycoproteins gHgL," *Journal of Virology* 85(24), 13214-13223.

Chia, W. K. et al. (2012) "A phase II study evaluating the safety and efficacy of an adenovirus-ΔLMP1-LMP2 transduced dendritic cell vaccine in patients with advanced metastatic nasopharyngeal carcinoma," *Annals of Oncology* 23(4), 997-1005.

Civoli, F. et al. (2012) "Development and optimization of neutralizing antibody assays to monitor clinical immunogenicity," *Bioanalysis* 4(22), 2725-2735.

Cohen, J. I. (2015) "Epstein-barr virus vaccines," *Clinical & Translational Immunology* 4(1), e32.

Cohen, J. I. et al. (2011) "Epstein-Barr Virus: An Important Vaccine Target for Cancer Prevention," *Science Translational Medicine* 3(107), 107fs107-107fs107.

Coté, T. R. et al. (1997) "Non-Hodgkin's lymphoma among people with AIDS: Incidence, presentation and public health burden," *International Journal of Cancer* 73(5), 645-650.

Eisenberg, R. J. et al. (2012) "Herpes Virus Fusion and Entry: A Story with Many Characters," *Viruses* 4(5), 800-832.

Fingeroth, J. D. et al. (1984) "Epstein-Barr virus receptor of human B lymphocytes is the C3d receptor CR2," *Proceedings of the National Academy of Sciences of the United States of America* 81(14), 4510-4514.

Fogg, M. H. et al. (2009) "Decreased EBNA-1-specific CD8+ T cells in patients with Epstein-Barr virus-associated nasopharyngeal carcinoma," *Proceedings of the National Academy of Sciences of the United States of America* 106(9), 3318-3323.

Fuller, A. O. et al. (1989) "Neutralizing antibodies specific for glycoprotein H of herpes simplex virus permit viral attachment to cells but prevent penetration," *Journal of Virology* 63(8), 3435-3443.

Gallot, G. et al. (2014) "T-cell therapy using a bank of EBV-specific cytotoxic T cells: lessons from a phase I/II feasibility and safety study," *Journal of Immunotherapy* 37(3), 170-179.

Ghiran, I. et al. (2008) "Ligation of erythrocyte CR1 induces its clustering in complex with scaffolding protein FAP-1," *Blood* 112(8), 3465-3473.

Goedert, J. J. et al. "Spectrum of AIDS-associated malignant disorders," *The Lancet* 351(9119), 1833-1839.

Gompels, U. A. et al. (1991) "Characterization and sequence analyses of antibody-selected antigenic variants of herpes simplex virus show a conformationally complex epitope on glycoprotein H," *Journal of Virology* 65(5), 2393-2401.

Gottschalk, S. et al. (2005) "Post-Transplant Lymphoproliferative Disorders," *Annual Review of Medicine* 56(1), 29-44.

Gu, S. Y. et al. (1995) "First EBV vaccine trial in humans using recombinant vaccinia virus expressing the major membrane antigen," *Developments in Biological Standardization* 84, 171-177.

Gujer, C. et al. (2015) "Animal models of Epstein Barr virus infection," *Current Opinion in Virology* 13(Supplement C), 6-10.

Heslop, H. E. et al. (1996) "Long-term restoration of immunity against Epstein-Barr virus infection by adoptive transfer of gene-modified virus-specific T lymphocytes," *Nature Medicine* 2(5), 551-555.

Hjalgrim, H. et al. (2007) "The epidemiology of EBV and its association with malignant disease," in *Human Herpesviruses: Biology, Therapy, and Immunoprophylaxis* (Arvin, A., et al., Eds.), Cambridge.

Hui, E. P. et al. (2013) "Phase I Trial of Recombinant Modified Vaccinia Ankara Encoding Epstein-Barr Viral Tumor Antigens in Nasopharyngeal Carcinoma Patients," *Cancer Research* 73(6), 1676.

Icheva, V. et al. (2013) "Adoptive Transfer of Epstein-Barr Virus (EBV) Nuclear Antigen 1—Specific T Cells As Treatment for EBV Reactivation and Lymphoproliferative Disorders After Allogeneic Stem-Cell Transplantation," *Journal of Clinical Oncology* 31(1), 39-48.

Jackman, W. T. et al. (1999) "Expression of Epstein-Barr virus gp350 as a single chain glycoprotein for an EBV subunit vaccine," *Vaccine* 17(7), 660-668.

Janz, A. et al. (2000) "Infectious Epstein-Barr Virus Lacking Major Glycoprotein BLLF1 (gp350/220) Demonstrates the Existence of Additional Viral Ligands," *Journal of Virology* 74(21), 10142-10152.

Kirschner, A. N. et al. (2006) "Soluble Epstein-Barr Virus Glycoproteins gH, gL, and gp42 Form a 1:1:1 Stable Complex That Acts Like Soluble gp42 in B-Cell Fusion but Not in Epithelial Cell Fusion," *Journal of Virology* 80(19), 9444-9454.

Kohrt, H. et al. (2009) "Dynamic CD8 T-cell responses to tumor-associated Epstein-Barr virus antigens in patients with Epstein-Barr virus-negative Hodgkin's disease," *Oncology Research* 18(5-6), 287-292.

Kutok, J. L. et al. (2006) "Spectrum of Epstein-Barr Virus-Associated Diseases," *Annual Review of Pathology: Mechanisms of Disease* 1(1), 375-404.

Laliberte, J. P. et al. (2006) "Integrity of Membrane Lipid Rafts Is Necessary for the Ordered Assembly and Release of Infectious Newcastle Disease Virus Particles," *Journal of Virology* 80(21), 10652-10662.

Lee, S. P. et al. (2004) "CD8 T Cell Recognition of Endogenously Expressed Epstein-Barr Virus Nuclear Antigen 1," *Journal of Experimental Medicine* 199(10), 1409-1420.

Li, Q. et al. (1997) "Epstein-Barr virus uses HLA class II as a cofactor for infection of B lymphocytes," *Journal of Virology* 71(6), 4657-4662.

Li, Q. et al. (1995) "The Epstein-Barr virus (EBV) BZLF2 gene product associates with the gH and gL homologs of EBV and carries an epitope critical to infection of B cells but not of epithelial cells," *Journal of Virology* 69(7), 3987-3994.

Lin, X. et al. (2008) "CD4 and CD8 T cell responses to tumour-associated Epstein-Barr virus antigens in nasopharyngeal carcinoma patients," *Cancer Immunology Immunotherapy* 57(7), 963-975.

Long, H. M. et al. (2013) "MHC II tetramers visualize human CD4(+) T cell responses to Epstein-Barr virus infection and demonstrate atypical kinetics of the nuclear antigen EBNA1 response," *Journal of Experimental Medicine* 210(5), 933-949.

Louis, C. U. et al. (2010) "Adoptive transfer of EBV-specific T cells results in sustained clinical responses in patients with locoregional nasopharyngeal carcinoma," *Journal of immunotherapy (Hagerstown, Md. : 1997)* 33(9), 983-990.

Luzuriaga, K. et al. (2010) "Infectious Mononucleosis," *New England Journal of Medicine* 362(21), 1993-2000.

McGinnes, L. W. et al. (2013) "Newcastle Disease Virus-Like Particles: Preparation, Purification, Quantification, and Incorporation of Foreign Glycoproteins," *Current protocols in microbiology* 30, Unit-18.12.

McGinnes, L. W. et al. (2003) "Evidence for Mixed Membrane Topology of the Newcastle Disease Virus Fusion Protein," *Journal of Virology* 77(3), 1951-1963.

Miller, N. et al. (1988) "A monoclonal antibody to glycoprotein gp85 inhibits fusion but not attachment of Epstein-Barr virus," *Journal of Virology* 62(7), 2366-2372.

(56) References Cited

OTHER PUBLICATIONS

Molesworth, S. J. et al. (2000) "Epstein-Barr Virus gH Is Essential for Penetration of B Cells but Also Plays a Role in Attachment of Virus to Epithelial Cells," *Journal of Virology* 74(14), 6324-6332.
Moutschen, M. et al. (2007) "Phase I/II studies to evaluate safety and immunogenicity of a recombinant gp350 Epstein-Barr virus vaccine in healthy adults," *Vaccine* 25(24), 4697-4705.
Murawski, M. R. et al. (2010) "Newcastle Disease Virus-Like Particles Containing Respiratory Syncytial Virus G Protein Induced Protection in BALB/c Mice, with No Evidence of Immunopathology," *Journal of Virology* 84(2), 1110-1123.
Naranatt, P. P. et al. (2002) "Characterization of gamma2-human herpesvirus-8 glycoproteins gH and gL," *Archives of Virology* 147(7), 1349-1370.
Nemerow, G. R. et al. (1984) "Early events in the infection of human B lymphocytes by Epstein-Barr virus: The internalization process," *Virology* 132(1), 186-198.
Nemerow, G. R. et al. (1989) "Identification of an epitope in the major envelope protein of Epstein-Barr virus that mediates viral binding to the B lymphocyte EBV receptor (CR2)," *Cell* 56(3), 369-377.
Nokta, M. et al. (1994) "Human monoclonal anti-cytomegalovirus (CMV) antibody (MSL 109): enhancement of in vitro foscarnet- and ganciclovir-induced inhibition of CMV replication," *Antiviral Research* 24(1), 17-26.
Ogembo, Javier G. et al. (2013) "Human Complement Receptor Type 1/CD35 Is an Epstein-Barr Virus Receptor," *Cell Reports* 3(2), 371-385.
Ogembo, J. G. et al. (2015) "A chimeric EBV gp350/220-based VLP replicates the virion B-cell attachment mechanism and elicits long-lasting neutralizing antibodies in mice," *Journal of Translational Medicine* 13(1), 50.
Paliard, X. et al. (2000) "Priming of Strong, Broad, and Long-Lived HIV Type 1 p55gag-Specific CD8+ Cytotoxic T Cells after Administration of a Virus-Like Particle Vaccine in Rhesus Macaques," *AIDS Research and Human Retroviruses* 16(3), 273-282.
Pantua, H. et al. (2005) "Characterization of an Alternate Form of Newcastle Disease Virus Fusion Protein," *Journal of Virology* 79(18), 11660-11670.
Pantua, H. D. et al. (2006) "Requirements for the Assembly and Release of Newcastle Disease Virus-Like Particles," *Journal of Virology* 80(22), 11062-11073.
Paramita, D. K. et al. (2011) "Humoral immune responses to Epstein-Barr virus encoded tumor associated proteins and their putative extracellular domains in nasopharyngeal carcinoma patients and regional controls," *Journal of Medical Virology* 83(4), 665-678.
Pavlova, S. et al. (2013) "An Epstein-Barr Virus Mutant Produces Immunogenic Defective Particles Devoid of Viral DNA," *Journal of Virology* 87(4), 2011-2022.
Rees, L. et al. (2009) "A phase I trial of epstein-barr virus gp350 vaccine for children with chronic kidney disease awaiting transplantation," *Transplantation* 88(8), 1025-1029.
Rickinson, A. B. et al. (2007) "Epstein-Barr Virus," in *Fields Virology* (Knipe, D., et al., Eds.) Fifth ed., pp. 2680-2700, Lippincott Wilkins and Williams, Philadelphia.
Roche, P. A. et al. (2015) "The ins and outs of MHC class II-mediated antigen processing and presentation," *Nature Reviews Immunology* 15, 203.

Rowe, C. L. et al. (2013) "A soluble form of Epstein-Barr virus gH/gL inhibits EBV-induced membrane fusion and does not function in fusion," *Virology* 436(1), 118-126.
Ruiss, R. et al. (2011) "A Virus-Like Particle-Based Epstein-Barr Virus Vaccine," *Journal of Virology* 85(24), 13105-13113.
Sashihara, J. et al. (2009) "Human Antibody Titers to Epstein-Barr Virus (EBV) gp350 Correlate with Neutralization of Infectivity Better than Antibody Titers to EBV gp42 Using a Rapid Flow Cytometry-Based EBV Neutralization Assay," *Virology* 391(2), 249-256.
Schirmbeck, R. et al. (1996) "Virus-like particles induce MHC class I-restricted T-cell responses. Lessons learned from the hepatitis B small surface antigen," *Intervirology* 39(1-2), 111-119.
Smith, C. et al. (2012) "A new approach for cellular immunotherapy of nasopharyngeal carcinoma," *Oncoimmunology* 1(8), 1440-1442.
Sokal, E. M. et al. (2007) "Recombinant gp350 vaccine for infectious mononucleosis: a phase 2, randomized, double-blind, placebo-controlled trial to evaluate the safety, immunogenicity, and efficacy of an Epstein-Barr virus vaccine in healthy young adults," *Journal of Infectious Diseases* 196(12), 1749-1753.
Speck, P. et al. (1999) "Epstein-Barr virus (EBV) infection visualized by EGFP expression demonstrates dependence on known mediators of EBV entry," *Archives of Virology* 144(6), 1123-1137.
Tanner, J. et al. (1987) "Epstein-barr virus gp350/220 binding to the B lymphocyte C3d receptor mediates adsorption, capping, and endocytosis," *Cell* 50(2), 203-213.
Tanner, J. et al. (1988) "Soluble gp350/220 and deletion mutant glycoproteins block Epstein-Barr virus adsorption to lymphocytes," *Journal of Virology* 62(12), 4452-4464.
Taylor, G. S. et al. (2004) "Dual Stimulation of Epstein-Barr Virus (EBV)-Specific CD4+- and CD8+-T-Cell Responses by a Chimeric Antigen Construct: Potential Therapeutic Vaccine for EBV-Positive Nasopharyngeal Carcinoma," *Journal of Virology* 78(2), 768-778.
Taylor, G. S. et al. (2014) "A recombinant modified vaccinia Ankara vaccine encoding Epstein-Barr virus (EBV) target antigens: a phase I trial in UK patients with EBV-positive cancer," *Clinical Cancer Research* 20(19), 5009-5022.
Wang, H.-B. et al. (2015) Neuropilin 1 is an entry factor that promotes EBV infection of nasopharyngeal epithelial cells, in *Nature Communications*, p. 6240.
Wang, X. et al. (1998) "Epstein-Barr Virus Lacking Glycoprotein gp42 Can Bind to B Cells but Is Not Able To Infect," *Journal of Virology* 72(1), 158-163.
Wu, L. et al. (2005) "Mutations of Epstein-Barr Virus gH That Are Differentially Able To Support Fusion with B Cells or Epithelial Cells," *Journal of Virology* 79(17), 10923-10930.
Wussow, F. et al. (2014) "Human cytomegalovirus vaccine based on the envelope gH/gL pentamer complex," *PLoS Pathogens* 10(11), e1004524.
Yajima, M. et al. (2008) "A New Humanized Mouse Model of Epstein-Barr Virus Infection That Reproduces Persistent Infection, Lymphoproliferative Disorder, and Cell-Mediated and Humoral Immune Responses," *Journal of Infectious Diseases* 198(5), 673-682.
PCT International Search Report of International Application No. PCT/US2016/022663 dated Jul. 22, 2016.

\* cited by examiner

FIGURE 7

Goal 2: Development of a novel gH/gL VLPs
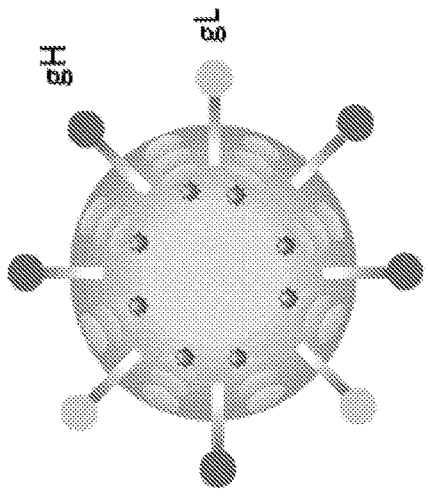
Specific Aims:
① Construct and determine the role of the gH/gL protein complex in generating EBV-specific neutralizing antibody responses in BALB/c mice.
FIGURE 12

Summary 1

① We have shown that EBV gp350/220 VLP-based vaccine can be generated using NDV platform.

① These gp350/220 VLPs were functionally active
- Bound CD21 and CD35
- Reactive to anti-gp350/220 mAbs ① gp350/220 VLPs generated nAbs in BALB/c mice comparable to EBV
- gp350/220 (-)HR2 F VLPs
- gp350/220/HR2 F ② Despite generation of anti-gp350/220 neutralizing mAbs, as in the cases of clinical trials, EBV infection was not completely neutralized.

③ We now aim to explore other glycoproteins as alternative vaccine candidates that can be used independently or together with gp350/220 VLPs to neutralize EBV infection.

FIGURE 13

Key Questions: Development of EBV vaccine candidates

- Is the EBV-glycoproteins VLP based vaccine candidates optimal as immunogens for preventing EBV infection and EBV-associated diseases?

- Can other viral antigens such as EBNA1-3, LMP1 and LMP2 be incorporated into VLPs to develop effective vaccine capable of inducing both humoral and cellular responses?

FIGURE

Goal 2: Development of a novel gH/gL-EBNA1-LMP2 VLPs

1. NDV-M (?)
2. NDV-NP (EBNA1/LMP2)
3. NDV-F/HN (gH/gL)

FIGURE 17

Rationale

- Despite strong evidence indicating that antibodies to gH/gL are capable of neutralizing EBV infection (*and also in other herpesviruses*), to my knowledge, no vaccine candidate has exploited the use of these proteins against EBV infection.

- Adoptive transfer of PBMCs for treatment of PTLDs and NPCs targeting LMP2 and EBNA1 is currently used in several clinical settings.
  1. Louis, et al., 2009, 2010, Heslop et al 1996 T cells adoptive transfer
  2. Chia et al., 2012 Phase 1 targeting NPC patients in China. Dendritic cells are transduced with adenovirus vector expressing LMP1 LMP2.

- DNA Vaccine: MVA-vector expressing EBNA1 and LMP1 or LMP2
  - Taylor et al., 2004 & Hui et al, 2013- EBNA1LMP2 (Phase I targeting NPC patients in China)
  - Taylor et al, 2014 (Phase I clinical trials in England)

- Safety is a major concern with this strategies
  - Can VLPs be used as a carrier for both virus glycoproteins and viral antigens expressed by infected or transformed cells?

FIGURE 18

Proof of principle: Can we generate EBVgp350/220 F VLPs expressing EGFP?

FIGURE 19

Summary 2

① We have shown that NDV-NP protein can be used as a carrier for EGFP

① The chimera NP-EGFP can be incorporated into gp350/220 VLPs which are functionally active
  • Bound CD21 and CD35
  • Reactive to anti-gp350/220 mAbs

FIGURE 29 gH/gL-NP-EBNA1-LMP2 VLPs

1. NDV-M (?)
2. NDV-NP (EBNA1/LMP2)
3. NDV-F/HN (gH/gL)

FIGURE 35

Summary 3

(1) We have shown that generation of EBNA1-gp350/220 VLP-based vaccine using NDV platform is feasible.

(1) We will now use the same platform to generate LMP2-gp350/220 VLPs.

(1) As indicated earlier, despite generation of anti-gp350/220 neutralizing mAbs, as in the cases of clinical trials, EBV infection was not completely neutralized, thus we aim to generate a second generation EBNA1-LMP2gH/gL VLPs (2) These EBV-VLP vaccine candidates will be used in Balb/c mice to test their efficacy in generation of humoral and cellular responses against EBV infection.

(3) Our study, is the first to show that viral intracellular protein can be packaged inside a VLP, with a potential to be used as a therapeutic vaccine.

(4) Can we use the same strategy to make candidate vaccines against other oncogenic viruses such as HPV, KSHV, HCV, HBV, HTLV1, Merckel Cell polyomervirus etc?

Generating NP-tEBNA1 Chimera Protein

FIGURE 50

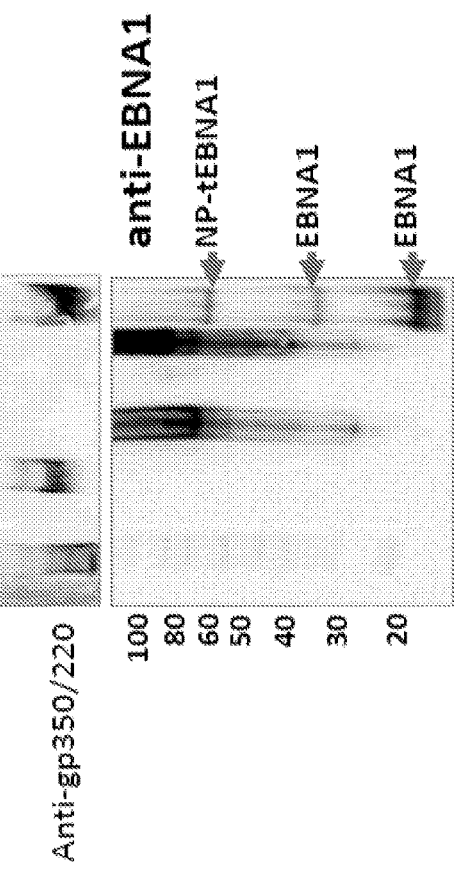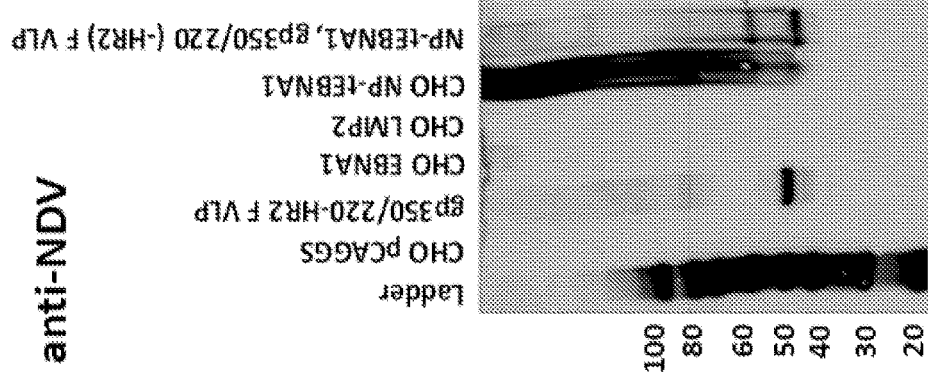
FIGURE 51

Terminal protein LMP2A [Human herpesvirus 4] (SEQ ID NO:01)

NCBI Reference Sequence: YP_401631.1

```
MGSLEMVPMGAGPPSPGGDPDGYDGGNNSQYPSASGSSGNTPTPPNDEERESNEEPPPPYEDPYWGNGDR
HSDYQPLGTQDQSLYLGLQHDGNDGLPPPPYSPRDDSSQHIYEEAGRGSMNPVCLPVIVAPYLFWLAAIA
ASCFTASVSTVVTATGLALSLLLLAAVASSYAAAQRKLLTPVTVLTAVVTFFAICLTWRIEDPPFNSLLF
ALLAAAGGLQGIYVLVMLVLLILAYRRRWRRLTVCGGIMFLACVLVLIVDAVLQLSPLLGAVTVVSMTLL
LLAFVLWLSSPGGLGTLGAALLTLAAALALLASLILGTLNLTTMFLLMLLWTLVVLLICSSCSSCPLSKI
LLARLFLYALALLLLASALIAGGSILQTNFKSLSSTEFIPNLFCMLLLIVAGILFILAILTEWGSGNRTY
GPVFMCLGGLLTMVAGAVWLTVMSNTLLSAWILTAGFLIFLIGFALFGVIRCCRYCCYYCLTLESEERPP
TPYRNTV
```

Figure 54

Glycoprotein gp110 precursor [Human herpesvirus 4] (SEQ ID NO:02)

NCBI Reference Sequence: YP_401713.1

```
  1 mtrrrvlsvv vllaalacrl gaqtpeqpap pattvqptat rqqtsfpfrv celsshgdlf
 61 rfssdiqcps fgtrenhteg llmvfkdnii pysfkvrsyt kivtniliyn gwyadsvtnr
121 heekfsvdsy etdqmdtiyq cynavkmtkd gltrvyvdrd gvnitvnlkp tgglangvrr
181 yasqtelyda pgwliwtyrt rttvnclitd mmaksnspfd ffvtttgqtv emspfydgkn
241 ketfherads fhvrtnykiv dydnrgtnpq gerrafldkg tytlswklen rtaycplqhw
301 qtfdstiate tgksihfvtd egtssfvtnt tvgielpdaf kcieeqvnkt mhekyeavqd
361 rytkgqeait yfitsgglll awlpltprsl atvknltelt tptssppssp sppapsaarg
421 stpaavlrrr rrdagnattp vpptapgksl gtlnnpatvq iqfaydslrr qinrmlgdla
481 rawcleqkrq nmvlreltki npttvmssiy gkavaakrlg dvisvsqcvp vnqatvtlrk
541 smrvpgsetm cysrplvsfs findtktyeg qlgtdneifl tkkmtevcqa tsqyyfqsgn
601 eihvyndyhh fktieldgia tlqtfislnt slienidfas lelysrdeqr asnvfdlegi
661 freynfqaqn iaglrkdldn avsngrnqfv dglgelmdsl gsvgqsitnl vstvgglfss
721 lvsgfisffk npfggmlilv lvagvvilvi sltrrtrqms qqpvqmlypg idelaqqhas
781 gegpginpis ktelqaimla lheqnqeqkr aaqraagpsv asralqaard rfpglrrrry
841 hdpetaaall geaetef
```

Figure 55

Glycoprotein gp85 precursor [Human herpesvirus 4] (SEQ ID NO:03)

NCBI Reference Sequence: YP_401700.1

```
  1 mqllcvfclv llwevgaasl sevklhldie ghashytipw telmakvpgl spealwrean
 61 vtedlasmln rykliyktsg tlgialaepv dipavsegsm qvdaskvhpg visglnspac
121 mlsaplekql fyyigtmlpn trphsyvfyq lrchlsyval singdkfqyt gamtskflmg
181 tykrvtekgd ehvlslvfgk tkdlpdlrgp fsypsltsaq sgdyslvivt tfvhyanfhn
241 yfvpnlkdmf sravtmtaas yaryvlqklv llemkggcre peldtetltt mfevsvaffk
301 vghavgetgn gcvdlrwlak sffeltvlkd iigicygatv kgmqsygler laamlmatvk
361 meelghltte kqeyalrlat vgypkagvys gliggatsvl lsaynrhplf qplhtvmret
421 lfigshvvlr elrlnvttqg pnlalyqlls talcsaleig evlrglalgt esglfspcyl
481 slrfdltrdk llsmapqeat ldqaavsnav dgflgrlsle redrdawhlp aykcvdrldk
541 vlmiiplinv tfiissdrev rgsalyeast tylssslfls pvimnkcsqg avageprqip
601 kiqnftrtqk scifcgfall sydekeglet ttyitsqevq nsilssnyfd fdnlhvhyll
661 lttngtvmei aglyeerahv vlaiilyfia falgiflvhk ivmffl
```

Figure 56 gL (BKRF2) [Human herpesvirus 4 type 2] (SEQ ID NO:04)

NCBI Reference Sequence: YP_001129472.1

```
  1 mrtvgvflat clvtifvlpt wgnwaypcch vtqlraqhll alenisdiyl vsnqtcdgfs
 61 laslnspkng snqlvisrca nglnvvsffi silkrsssal tghlrelltt letlygsfsv
121 edlfganlnr yawhrgg
```

Figure 57

L1 [Human papillomavirus type 16] (SEQ ID NO:05)

GenBank: AAD33259.1

```
  1 mqvtfiyilv itcyendvnv yhiffqmslw lpseatvylp pvpvskvvst deyvartniy
 61 yhagtsrlla vghpyfpikk pnnnkilvpk vsglqyrvfr ihlpdpnkfg fpdtsfynpd
121 tqrlvwacvg vevgrgqplg vgisghplln klddtenasa yaanagvdnr ecismdykqt
181 qlcligckpp igehwgkgsp ctnvavnpgd cpplelintv iqdgdmvdtg fgamdfttlq
241 anksevpldi ctsickypdy ikmvsepygd slffylrreq mfvrhlfnra gavgenvpdd
301 lyikgsgsta nlassnyfpt psgsmvtsda qifnkpywlq raqghnngic wgnqlfvtvv
361 dttrstnmsl caaistsett ykntnfkeyl rhgeeydlqf ifqlckitlt advmtyihsm
421 nstiledwnf glqpppggtl edtyrfvtsq aiacqkhtpp apkedplkky tfwevnlkek
481 fsadldqfpl grkfllqagl kakpkftlgk rkatpttsst sttakrkkrk l
```

Figure 58

L2 [Human papillomavirus type 16] (SEQ ID NO:06)

GenBank: AAD33258.1

```
  1 mrhkrsakrt krasatqlyk tckqagtcpp diipkvegkt iadqilqygs mgvffgglgi
 61 gtgsgtggrt gyiplgtrpp tatdtlapvr ppltvdpvgp sdpsivslve etsfidagap
121 tsvpsippdv sgfsittstd ttpaildinn tvttvtthnn ptftdpsvlq pptpaetggh
181 ftlssstist hnyeeipmdt fivstnpntv tsstpipgsr pvarlglysr ttqqvkvvdp
241 afittptkli tydnpayegi dvdntlyfss ndnsiniapd pdfldivalh rpaltsrrtg
301 irysrignkq tlrtrsgksi gakvhyyydf stidsaeeie lqtitpstyt ttshaalpts
361 innglydiya ddfitdtstt pvpsvpstsl sgyipantti pfggaynipl vsgpdipini
421 tdqapslipi vpgspqytii adagdfylhp syymlrkrrk rlpyffsdvs laa
```

Figure 59

L2 protein [Human papillomavirus type 18] (SEQ ID NO:07)

GenBank: AGG40790.1

```
  1 mvshraarrk rasvtdlykt ckqsgtcppd vvpkvegttl adkilqwssl giflgglgig
 61 tgsgtggrtg yiplggrsnt vvdvgptrpp vviepvgptd psivtlieds svvtsgaprp
121 tftgtsgfdi tsagtttpav lditpsstsv sisttnftnp afsdpsiiev pqtgevagnv
181 fvgtptsgth gyeeiplqtf assgtgeepi sstplptvrr vagprlysra yqqvsvanpe
241 fltrpsslit ydnpafepvd ttltfdprsd vpdsdfmdii rlhrpaltsr rgtvrfsrlg
301 qratmftrsg tqigarvhfy hdispiapsp eyielqplvs atedndlfdi yaddmdpavp
361 vpsrsttsfa ffkysptiss assysnvtvp ltsswdvpvy tgpditlpst tsvwpivspt
421 apastqyigi hgthyylwpl yyfipkkrkr vpyffadgfv aa
```

Figure 60

EBNA-1 protein [Human herpesvirus 4] (SEQ ID NO:08)

NCBI Reference Sequence: YP_401677.1

```
  1 msdegpgtgp gnglgekgdt sgpegsggsg pqrrggdnhg rgrgrgrgrg ggrpgapggs
 61 gsgprhrdgv rrpqkrpsci gckgthggtg agagaggaga ggagagggag agggaggagg
121 aggagaggga gagggaggag gagagggaga gggaggagag ggaggaggag agggagaggg
181 aggagaggga ggaggagagg gagaggagga ggagaggaga gggaggagga gaggagagga
241 gaggagagga ggagaggagg agaggaggag agggaggaga gggaggagag gaggagagga
301 ggagaggagg agagggagag gagagggrg rggsggrgrg gsggrgrggs ggrrgrgrer
361 arggsrerar grgrgrgekr prspssqsss sgspprrppp grrpffhpvg eadyfeyhqe
421 ggpdgepdvp pgaieqgpad dpgegpstgp rgqgdggrrk kggwfgkhrg qggsnpkfen
481 iaeglralla rshverttde gtwvagvfvy ggsktslynl rrgtalaipq crltplsrlp
541 fgmapgpgpq pgplresivc yfmvflqthi faevlkdaik dlvmtkpapt cnirvtvcsf
601 ddgvdlppwf ppmvegaaae gddgddgdeg gdgdegeegq e
```

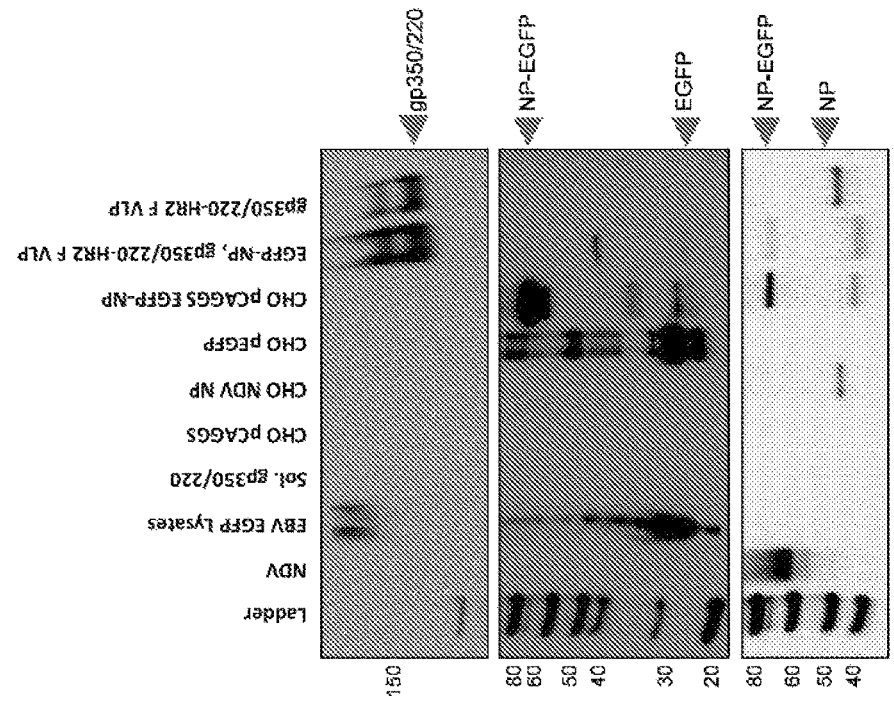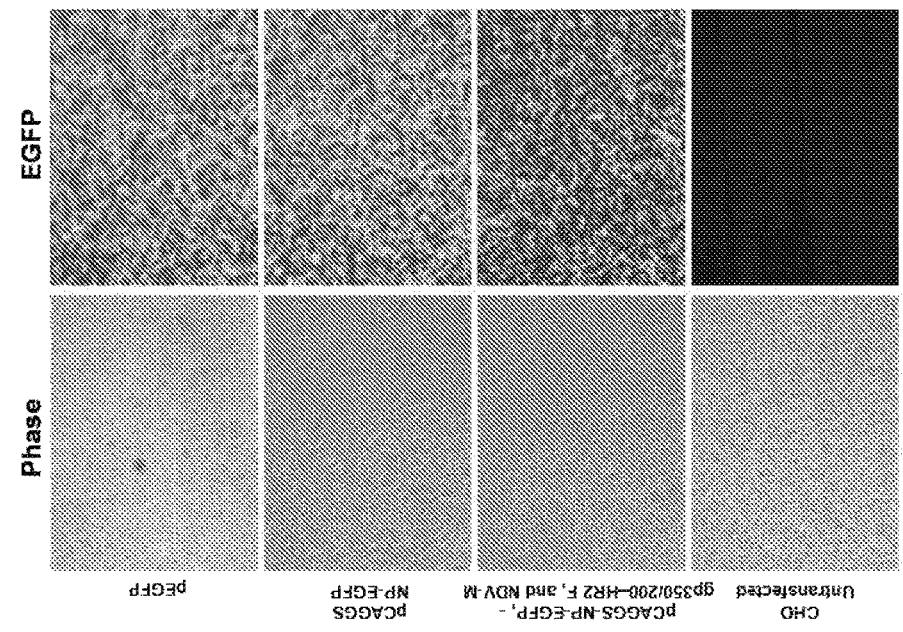
Figure 80

VIRUS-LIKE PARTICLE COMPOSITIONS AND VACCINES AGAINST EPSTEIN-BARR VIRUS INFECTION AND DISEASE

This application claims priority to U.S. provisional Application Ser. No. 62/134,785, filed on Mar. 18, 2015, which is herein incorporated by reference in its entirety.

FIELD OF THE INVENTION

The present invention relates to prophylactic and/or therapeutic vaccines that contain Newcastle disease virus (NDV) virus-like particles (VLPs) comprising one or more Epstein-Barr Virus (EBV) antigens. The invention's prophylactic and/or therapeutic vaccines are useful for preventing and/or treating infection with EBV and/or disease associated Epstein-Barr Virus, such as cancer.

BACKGROUND OF THE INVENTION

Epstein-Barr virus (EBV), an oncogenic gammaherpesvirus, causes acute infectious mononucleosis (AIM) and is linked to the development of several human malignancies. Approaches for EBV vaccine development are limited due in part to the oncogenic potential of the EBV genome and lack of animal models to test vaccine candidates. The EBV envelope glycoprotein, gp350/220, has been proposed as a vaccine antigen. However, in small Phase I/II clinical trials, vaccination with either vector constructs expressing gp350/220, or with the purified recombinant gp350 protein, did not prevent EBV infection although it did reduce the incidence of acute infectious mononucleosis (AIM) in young adults. Importantly, recombinant EBV Δgp350/220 can infect both epithelial and primary B cells in vitro. While previous studies indicate that immunity to gp350/220 can limit infection, the poor success of using gp350/220 as a single vaccine antigen calls for innovative approaches utilizing multiple EBV proteins.

At least 4 EBV gp350/220 vaccine candidates have been tested in "clinical trials" such as Vaccinia vector expressing gp350/220 (Gu et al., 1995 (Phase I-Chinese population, EBV naïve 1-3 years old children), and Recombinant gp350 in CHO cells (non-splicing variant) (3 dose regimen adjuvanted with ASO4) (Jackman et al. 1999; Moutchen et al, 2007. (Phase I/II) Safety and Immunogenicity in aged 18-37 years old EBV naïve Belgians; Sokal et al., 2007. Phase I randomized, double-blind placebo control in aged 16-25 years EBV naïve Belgians; Rees et al., 2009. Phase I chronic kidney disease kids awaiting organ transplants (UK)). However, none of these vaccine candidates achieved complete blockage of EBV infection.

Notably, EBNA1, LMP2 and gp350/220 antigens have been developed and independently tested in various clinical trials as vaccine candidates against EBV infection and EBV+ cells with promising results.

Candidate therapeutic vaccines in clinical trials include MVA-vector expressing EBNA-1 and LMP1 or LMP2 (Taylor et al., 2004 construction of the MVA vector exppressing EBNA1 and or LMP2; Hui et al., 2013-EBNA1-LMP2 (Phase I targeting NPC patients in China); Taylor et al., 2014 EBNA1-LMP2 (A Phase I Trial in UK Patients with EBV-Positive Cancer); as well as Adoptive transfer PBMCs for treatment of PTLDs and NPCs (Louis, et al., 2009, 2010, Heslop et al. 1996 T cells adoptive transfer; and Chia et al., 2012 Phase I targeting NPC patients in China. Dendritic cells are transduced with adenovirus vector expressing ΔLMP1-LMP2). A recent phase I clinical trial of recombinant modified vaccinia Ankara (MVA) vector encoding deletion of Gly-Ala regions from the EBNA1 sequence fused to LMP2 as a vaccine candidate elicited a robust EBV-specific CD4+ and CD8+ T cell response in humans. However, the strategy used to deliver these two important EBV antigens, known for their oncogenic potential, may pose major health risks, particularly in immunosuppressed individuals. Furthermore, these vaccine candidates cannot generate neutralizing antibodies to eliminate reactivation or new EBV infections. There is also a risk of vaccine tolerance since the protein is constantly produced.

Thus, there is an urgent need for EBV vaccines that are safe, prevent EBV infection and/or limit EBV disease symptoms.

BRIEF DESCRIPTION OF THE DRAWINGS

FIG. 4-47. Refer to each drawing for its description.

FIG. 50-53. Refer to each drawing for its description.

FIG. 54. Terminal protein LMP2A [Human herpesvirus 4] (SEQ ID NO:01) NCBI Reference Sequence: YP_401631.1.

FIG. 55. Glycoprotein gp110 precursor [Human herpesvirus 4] (SEQ ID NO:02) NCBI Reference Sequence: YP_401713.1.

FIG. 56. gH, Glycoprotein gp85 precursor [Human herpesvirus 4] (SEQ ID NO:03) NCBI Reference Sequence: YP_401700.1.

FIG. 57. gL (BKRF2) [Human herpesvirus 4 type 2] (SEQ ID NO:04) NCBI Reference Sequence: YP_001129472.1.

FIG. 58. L1 [Human papillomavirus type 16] (SEQ ID NO:05) GenBank: AAD33259.1.

FIG. 59. L2 [Human papillomavirus type 16] (SEQ ID NO:06) GenBank: AAD33258.1.

FIG. 60. L2 protein [Human papillomavirus type 18] (SEQ ID NO:07) GenBank: AGG407090.1.

FIG. 61. EBNA-1 protein [Human herpesvirus 4] (SEQ ID NO:08) NCBI Reference Sequence: YP_401677.1.

Figure 63:
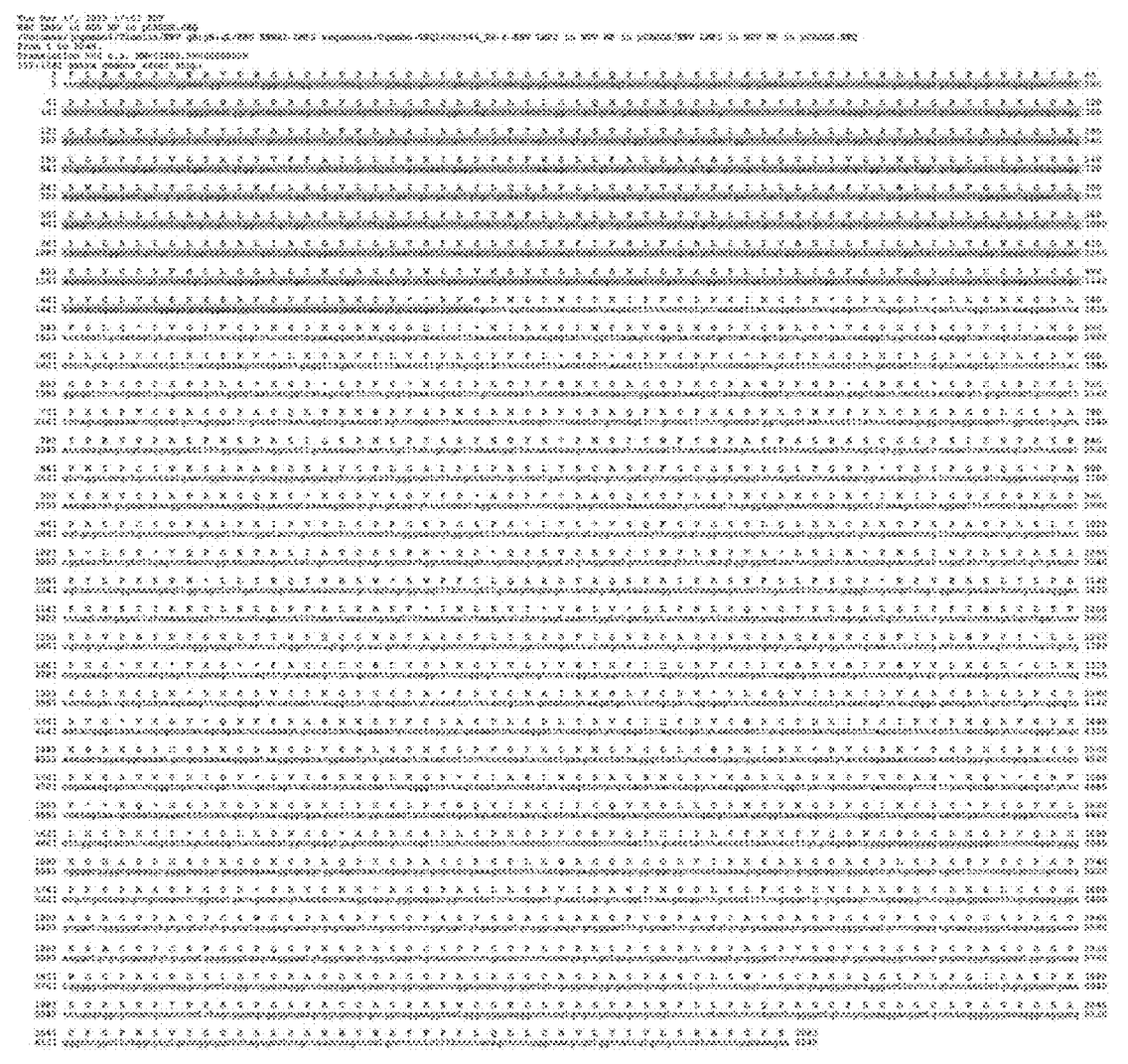

FIG. 63. EBV LMP2 in NDV NP in pCAGGS.SEQ Translation

Figure 64:
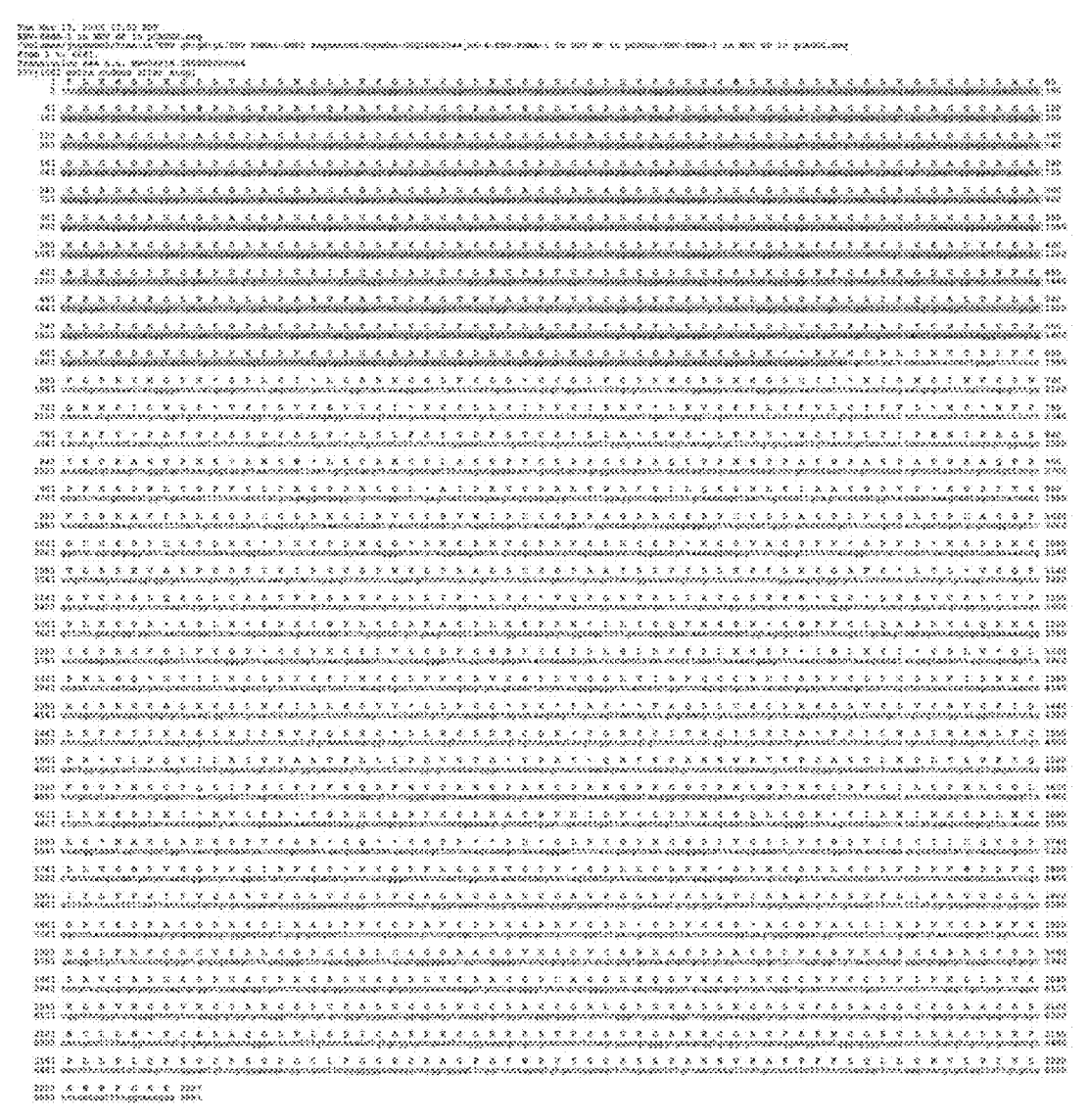

FIG. 64. EBV-EBNA-1 in NDV NP in pCAGGS.seq Translation

Figure 65:
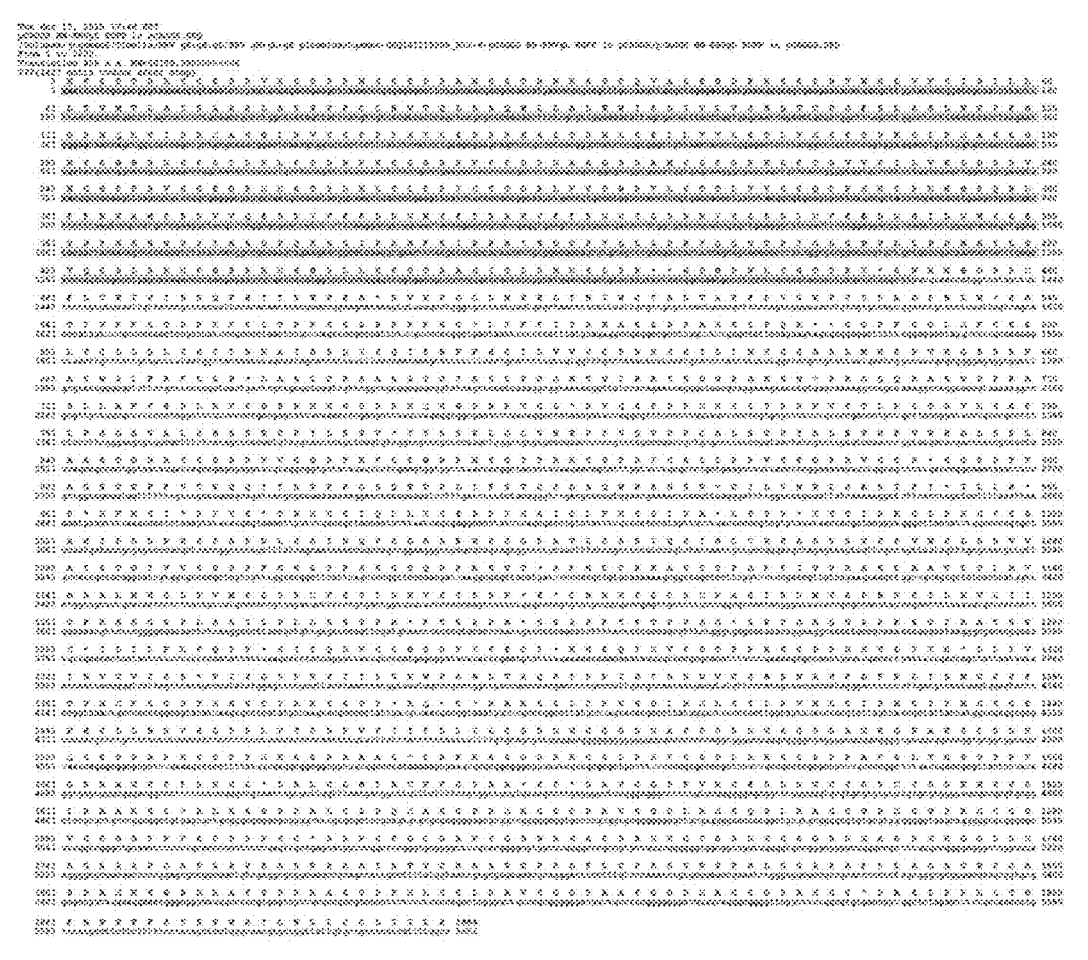

FIG. 65. pCAGGS HN-EBVgL EGFP in pCAGGS.SEQ Translation

Figure 66:
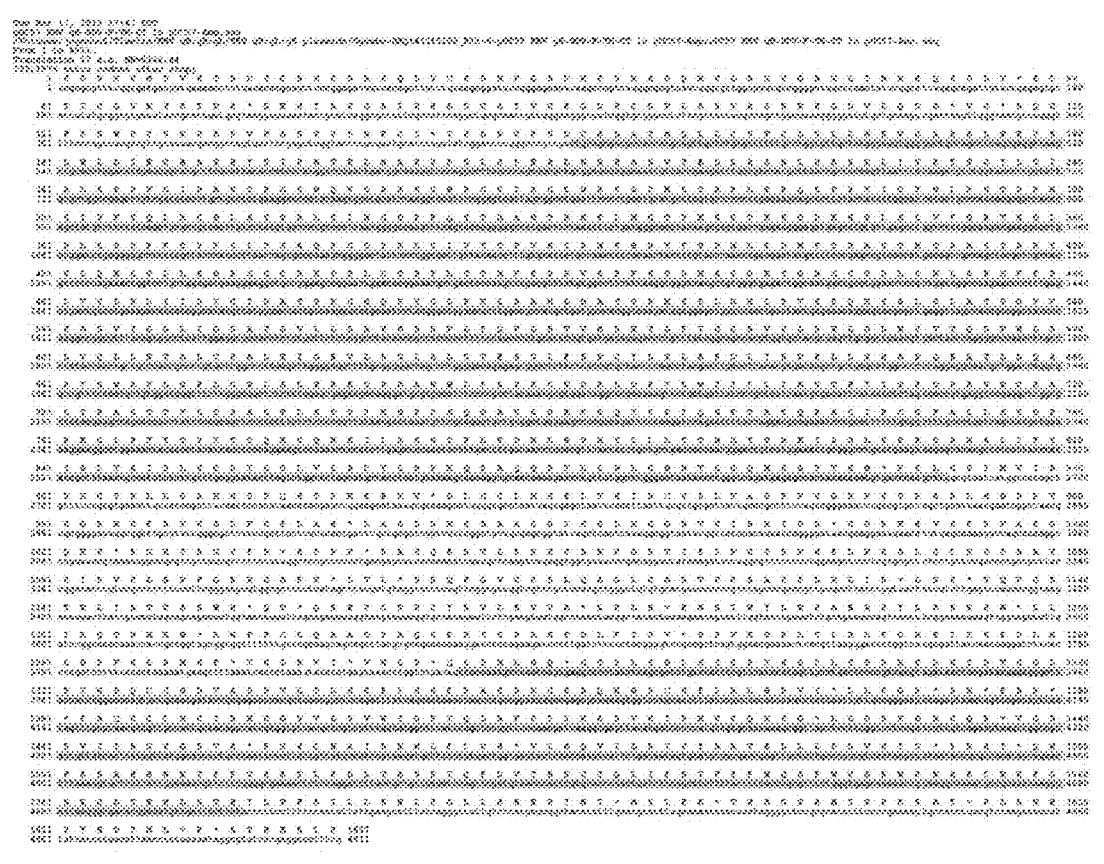

FIG. 66. pUC57 EBV gH-NDV-F-TM-CT in pUC57-Amp.seq Translation

Figure 69:
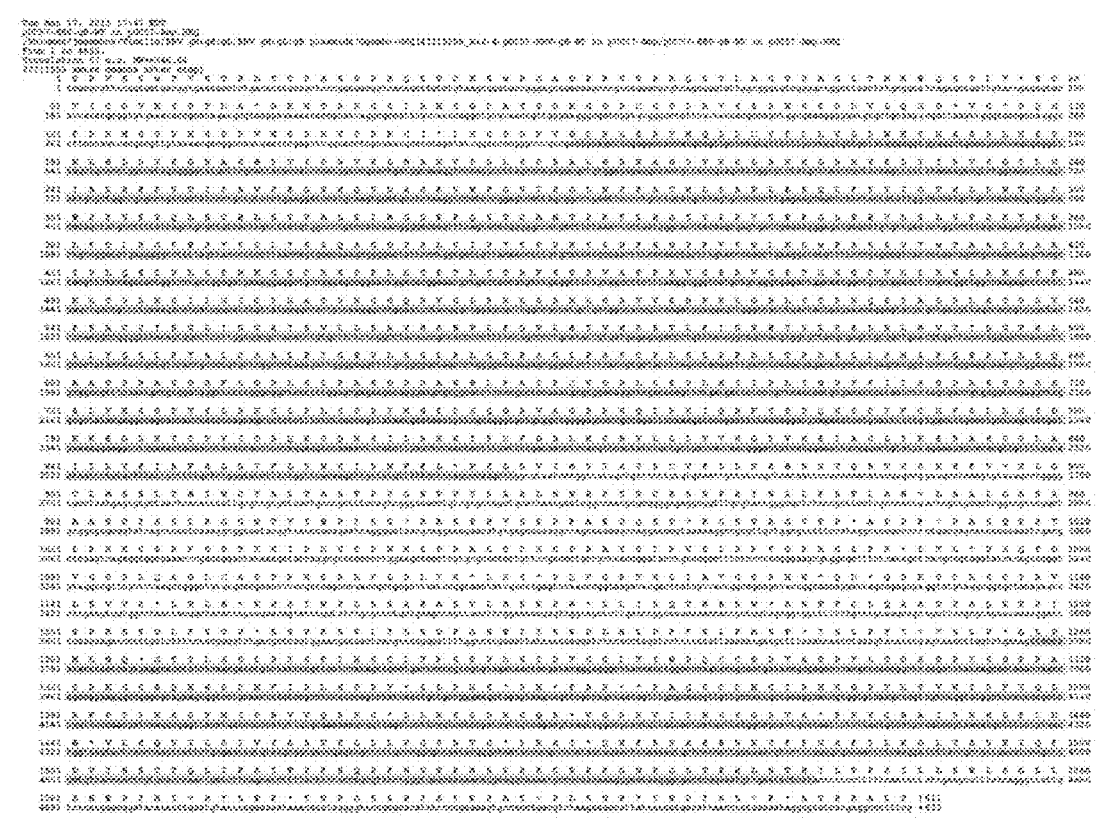

FIG. 69. pUC57-EBV-gH-WT in pUC57-Amp.SEQ Translation

Figure 70:
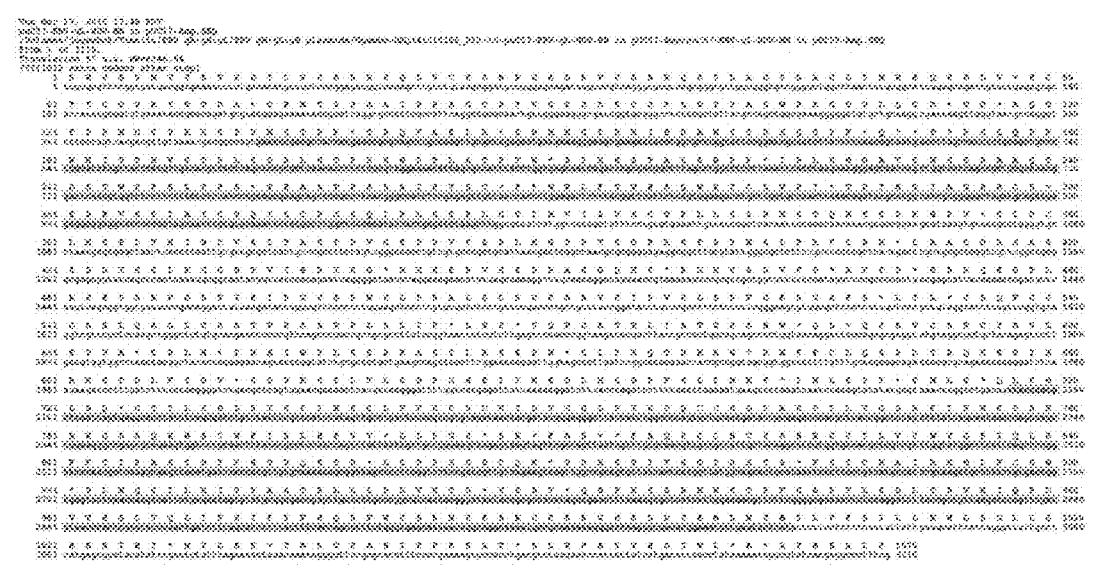

FIG. 70. pUC57-EBV-gL-NDV-HN in pUC57-Amp.SEQ Translation

Figure 71:
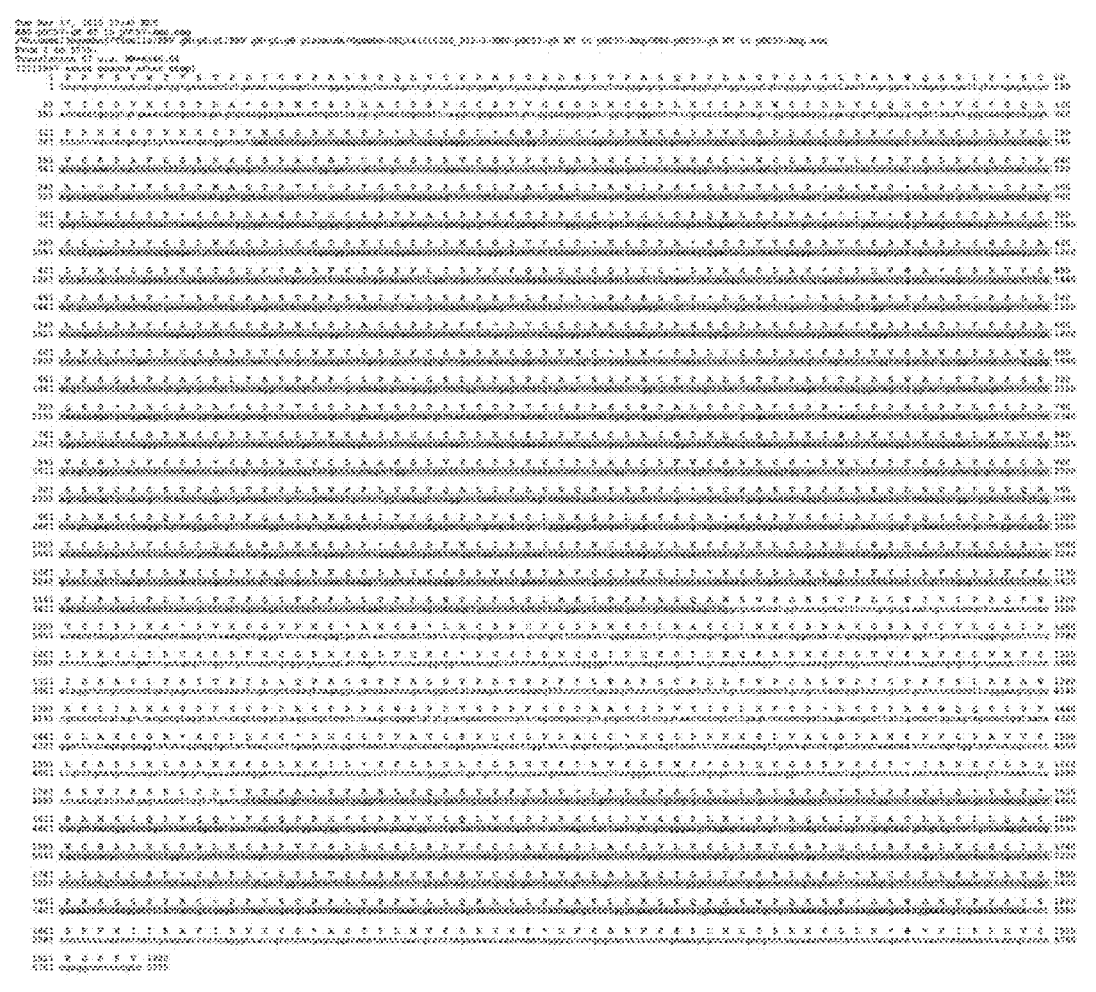

FIG. 71. EBV-pUC57-gB WT in pUC57-Amp.seq Translation

FIG. 79. Schematic of construction and assembly of NDV NP as a carrier of EGFP into gp350/220/HR2 F VLPs. Schematic of (A) NP-EGFP chimera plasmid construction; (B) gp350/220-HR2 F plasmid construction showing full-length NDV-F (top), full-length wild type gp350/220 with splicing sites (middle) and chimeric gp350/220 NDV F HR2 (bottom); and (C) co-transfection of plasmids into CHO cells for assembly and release of VLPs.

FIG. 80. Characterization of EBV gp350/220 VLPs incorporated with NDV-NP-EGFP, (A) Expression of EGFP in CHO cells transfected with pCAGGS-NDV-NP-EGFP detected by microscopy. (B) Immunoblot of VLPs purified from the supernatant of transfected CHO cells using mAb-72A1 (anti-gp350/220) as the detection antibody. Lysates were separated on a 4-12% gel. Purified EBV from B95-8-EGFP cells was used as a positive control.

DEFINITIONS

Figure 1:
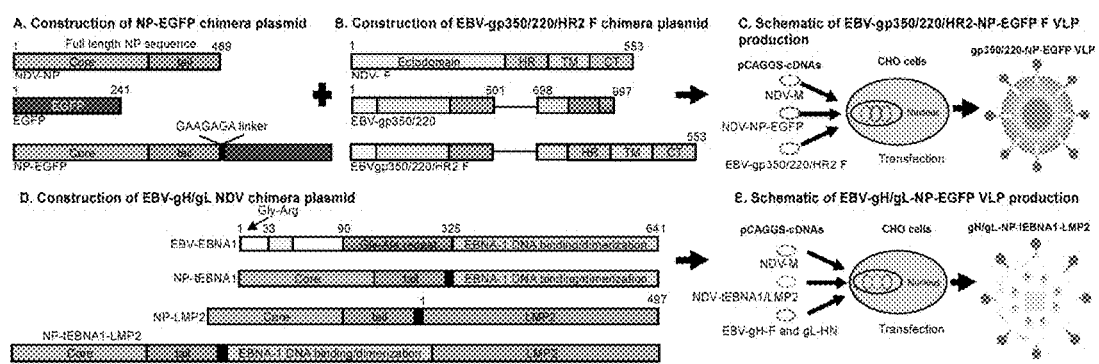
FIG. 1. Schematic diagram showing construction and assembly of NDV NP as a carrier of EGFP, truncated EBNA1, LMP2 (full length) and/or tEBNA1-LMP2 incorporated into either gp350/220 or gH/gL VLPs. (A) Construction of NP-EGFP chimera plasmid. (B) Diagram of full-length NDV-F (top), full-length wild type NDV (middle) and chimeric gp350/220 NDV F (bottom). (C) Schematic illustration of cDNAs pCAGGS-NDV-M, -NP-EGFP and gp350/220-F (chimera) all cotransfected into CHO cells for VLPs assembly and release. (D) Construction of NP-tEBNA1, LMP2 and/or tEBNA1-LMP2. (E) Schematic illustration of cDNAs pCAGGS NDV-M, -NP-tEBNA1, LMP2 and/or tEBNA1-LMP2 and gH-F/gL-HN (chimeras) cotransfected into CHO cells for VLPs assembly and release.

To facilitate understanding of the invention, a number of terms are defined below.

The term "recombinant" molecule refers to a molecule that is produced using molecular biological techniques. Thus, "recombinant DNA molecule" refers to a DNA molecule that is comprised of segments of DNA joined together by means of molecular biological techniques. A "recombinant protein" or "recombinant polypeptide" as used herein refers to a protein molecule that is expressed using a recombinant DNA molecule. A "recombinant" virus-like particle (VLP) refers to a VLP that is expressed using a recombinant DNA molecule.

A "virus-like particle" and "VLP" interchangeably refer to a non-replicating, non-infectious particle shell that contains one or more virus proteins, lacks the viral RNA and/or DNA genome, and that approximately resembles live virus in external conformation. Methods for producing and characterizing recombinant VLPs containing Newcastle Disease Virus (NDV) proteins have been described (Pantua et al. (2006) J. Virol. 80:11062-11073; U.S. Pat. No. 7,951,384 issued to Morrison et al. on May 1, 2011; U.S. Pat. No. 8,974,797, issued to Morrison on Mar. 10, 2015, each of which is incorporated by reference). Further methods for producing NDV VLPs are disclosed herein.

The term "inside" a VLP when made in reference to the location of a polypeptide sequence means that the polypeptide sequence is located on the inner surface of the virus-like particle, and is encapsulated by the virus-like particle such that the polypeptide sequence is not exposed on the outside surface of the virus-like particle. Preferably, though not necessarily, the polypeptide that is inside the VLP is not accessible to binding with antibodies that are present outside the VLP.

"Operable combination" and "operably linked" when in reference to the relationship between nucleic acid sequences and/or amino acid sequences refers to linking (i.e., fusing) the sequences in frame such that they perform their intended function. For example, operably linking a promoter sequence to a nucleotide sequence of interest refers to linking the promoter sequence and the nucleotide sequence of interest in a manner such that the promoter sequence is capable of directing the transcription of the nucleotide sequence of interest and/or the synthesis of a polypeptide encoded by the nucleotide sequence of interest.

The term "matrix protein", "membrane protein", or "M protein" as used herein, means any protein localized between the envelope and the nucleocapsid core and facilitates the organization and maintenance of the virion structure and budding processes. Exemplary NDV M protein sequences include those described in U.S. Pat. No. 7,951,384 issued to Morrison et al. on May 1, 2011; U.S. Pat. No. 8,974,797, issued to Morrison on Mar. 10, 2015, each of which is incorporated by reference.

The term "nucleocapsid protein" or "NP protein" as used herein, means any protein that associated with genomic RNA (i.e., for example, one molecule per hexamer) and protects the RNA from nuclease digestion. Exemplary NP protein sequences from NDV include those described in U.S. Pat. No. 7,951,384 issued to Morrison et al. on May 1, 2011; U.S. Pat. No. 8,974,797, issued to Morrison on Mar. 10, 2015, each of which is incorporated by reference.

The term "fusion protein" or "F protein" as used herein, means any protein that projects from the envelope surface and mediates host cell entry by inducing fusion between the viral envelope and the cell membrane. However, it is not intended that the present invention be limited to functional F proteins. For example, an F protein may be encoded by a mutant F gene such as, but not limited to, F-K115Q. F-K115Q is believed to eliminate the normal cleavage and subsequent activation of the fusion protein. F-K115Q mimics naturally occurring F-protein mutations in avirulent NDV strains, and in cell culture, eliminates any potential side effects of cell-cell fusion on the release of VLPs. Exemplary NDV F protein sequences include those described in U.S. Pat. No. 7,951,384 issued to Morrison et al. on May 1, 2011; U.S. Pat. No. 8,974,797, issued to Morrison on Mar. 10, 2015, each of which is incorporated by reference.

"HR2 domain," "heptad repeat domain 2," "HR-B domain," and "heptad repeat domain B" interchangeably refer to a sequence that is present in the F protein of a Paramyxovirus, and that folds as an amphipathic alpha helix. The HR2 domain of NDV is exemplified by those described in U.S. Pat. No. 8,974,797, issued to Morrison on Mar. 10, 2015, incorporated by reference.

The term "haemagglutinin-neuraminidase protein", "HN protein", or G protein as used herein, means any protein that spans the viral envelope and projects from the surface as spikes to facilitate cell attachment and entry (i.e., for example, by binding to sialic acid on a cell surface). These proteins possess both haemagglutination and neuraminidase activity. Exemplary NDV HN protein sequences include those described in U.S. Pat. No. 7,951,384 issued to Morrison et al. on May 1, 2011; U.S. Pat. No. 8,974,797, issued to Morrison on Mar. 10, 2015, each of which is incorporated by reference.

The term "glycoprotein" as used herein, refers to any protein conjugated to a carbohydrate.

Figure 48:
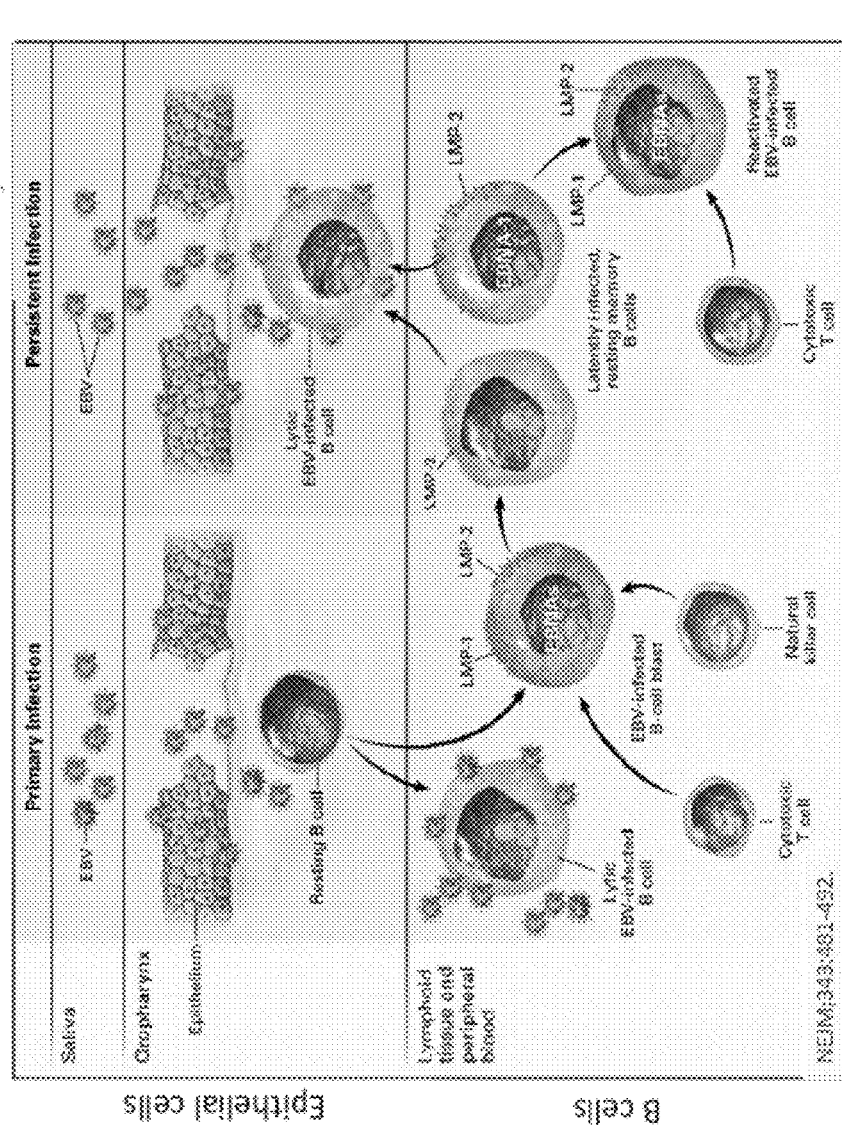
FIG. 48. EBV entry pathways.

"Epstein-Barr Virus," "EBV," "human herpesvirus 4" "HHV-4" interchangeably refer to an oncogenic human herpesvirus. EBV is the cause of acute infectious mononucleosis (AIM, also known as glandular fever). It is also associated with particular forms of cancer, such as Hodgkin's lymphoma, Burkitt's lymphoma, nasopharyngeal carcinoma, and conditions associated with human immunodeficiency virus (HIV), such as hairy leukoplakia and central nervous system lymphomas. EBV infects B cells of the immune system and epithelial cells. Once the virus's initial lytic infection is brought under control, EBV latently persists in the individual's B cells for the rest of the individual's life due to a complex life cycle (FIG. 48) that includes alternate latent and lytic phases.

"Symptom of EBV infection" includes acute infectious mononucleosis (AIM, also known as glandular fever) and/or the presence of EBV-associated cancer. "EBV-associated cancer" refers to cancer that is caused and/or aggravated, at least in part, by infection with EBV, such as Hodgkin's lymphoma, Burkitt's lymphoma, nasopharyngeal carcinoma, cervical cancer, hairy leukoplakia and central nervous system lymphomas.

The terms "antigen," "immunogen," "antigenic," "immunogenic," "antigenically active," and "immunologically active" when made in reference to a molecule, refer to any substance that is capable of inducing a specific humoral and/or cell-medicated immune response. In a particular embodiment, the antigen comprises at least a portion or an ectodomain.

The term "ectodomain" when in reference to a membrane protein refers to the portion of the protein that is exposed on the extracellular side of a lipid bilayer of a cell, virus and the like.

"EBV antigen" refers to an antigen from EBV, such as "gB, gH, gL, and gp350/220" and tumor-associated EBV antigens.

The term "gB" refers to glycoprotein gp110 precursor of Human herpesvirus 4 and is exemplified in FIG. 55 (SEQ ID NO:02), NCBI Reference Sequence: $YP_{13}$ 401713.1.

The term "gH" refers to glycoprotein gp85 precursor of human herpesvirus 4 and is exemplified by in FIG. 56 (SEQ ID NO:03), NCBI Reference Sequence: YP_401700.1.

The term "gL" and "BKRF2" are interchangeably used, and exemplified in FIG. 57 by BKRF2 protein of human herpesvirus 4 type 2 (SEQ ID NO:04), NCBI Reference Sequence: YP_001129472.1.

The term "gp350/220" is the predominant EBV envelope protein. Interactions between EBV gp350/220 and complement receptor type 2 (CR2)/CD21 and/or (CR1)/CD35 on B-cells is required for cellular attachment and initiation of latent infection.

"Tumor-associated EBV antigens" are EBV antigens that are associated with tumors in subjects who are infected with EBV. Exemplary tumor-associated EBV antigens include EBNA1, LMP1, LMP2, and BARF1, those described in Lin et al. "CD4 and CD8 T cell responses to tumour-associated Epstein-Barr virus antigens in nasopharyngeal carcinoma patients," Cancer Immunol Immunother. 2008 July; 57(7); 963-75; Kohrt et al. "Dynamic CD8 T-cell responses to tumor-associated Epstein-Barr virus antigens in patients with Epstein-Barr virus-negative Hodgkin's disease," Oncol Res. 2009; 18(5-6); 287-92; Parmita et al., "Humoral immune responses to Epstein-Barr virus encoded tumor associated proteins and their putative extracellular domains in nasopharyngeal carcinoma patients and regional controls," J Med Virol. 2011 April; 83(4):665-78.

Figure 8:
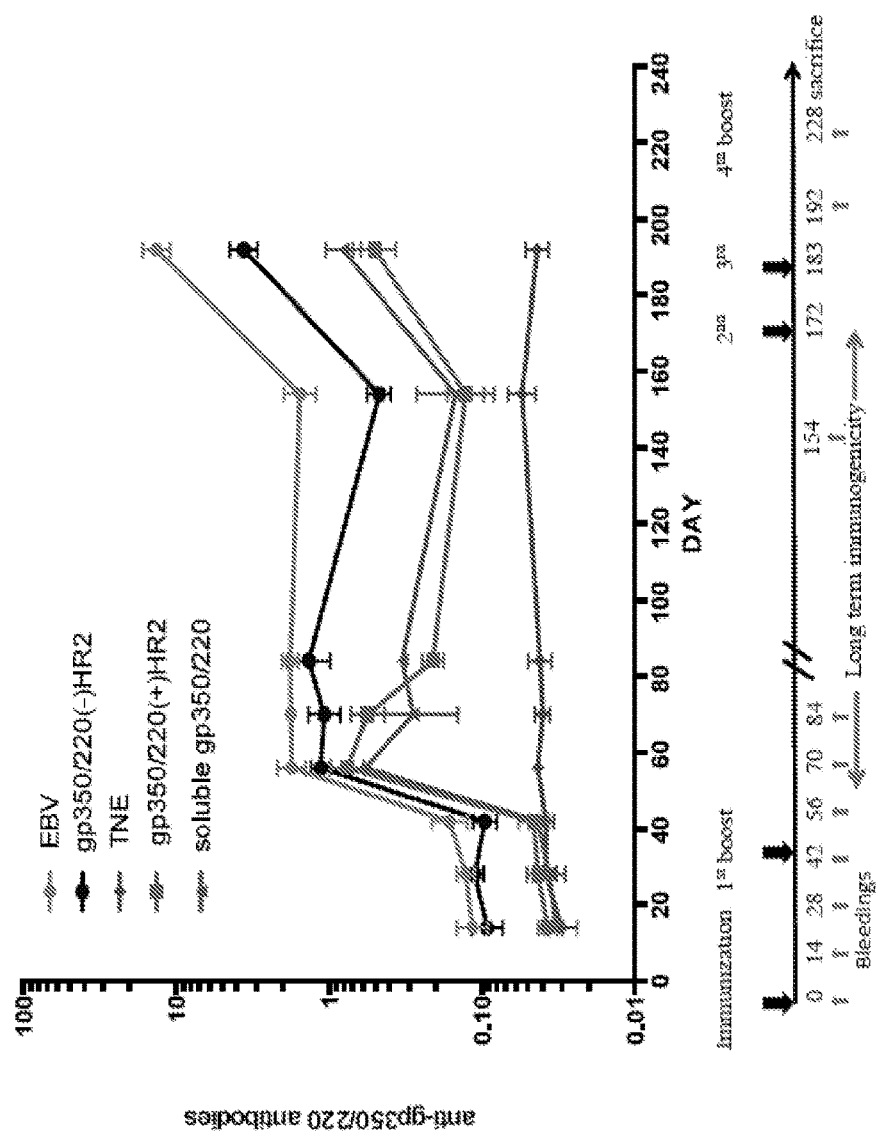
Figure 9:
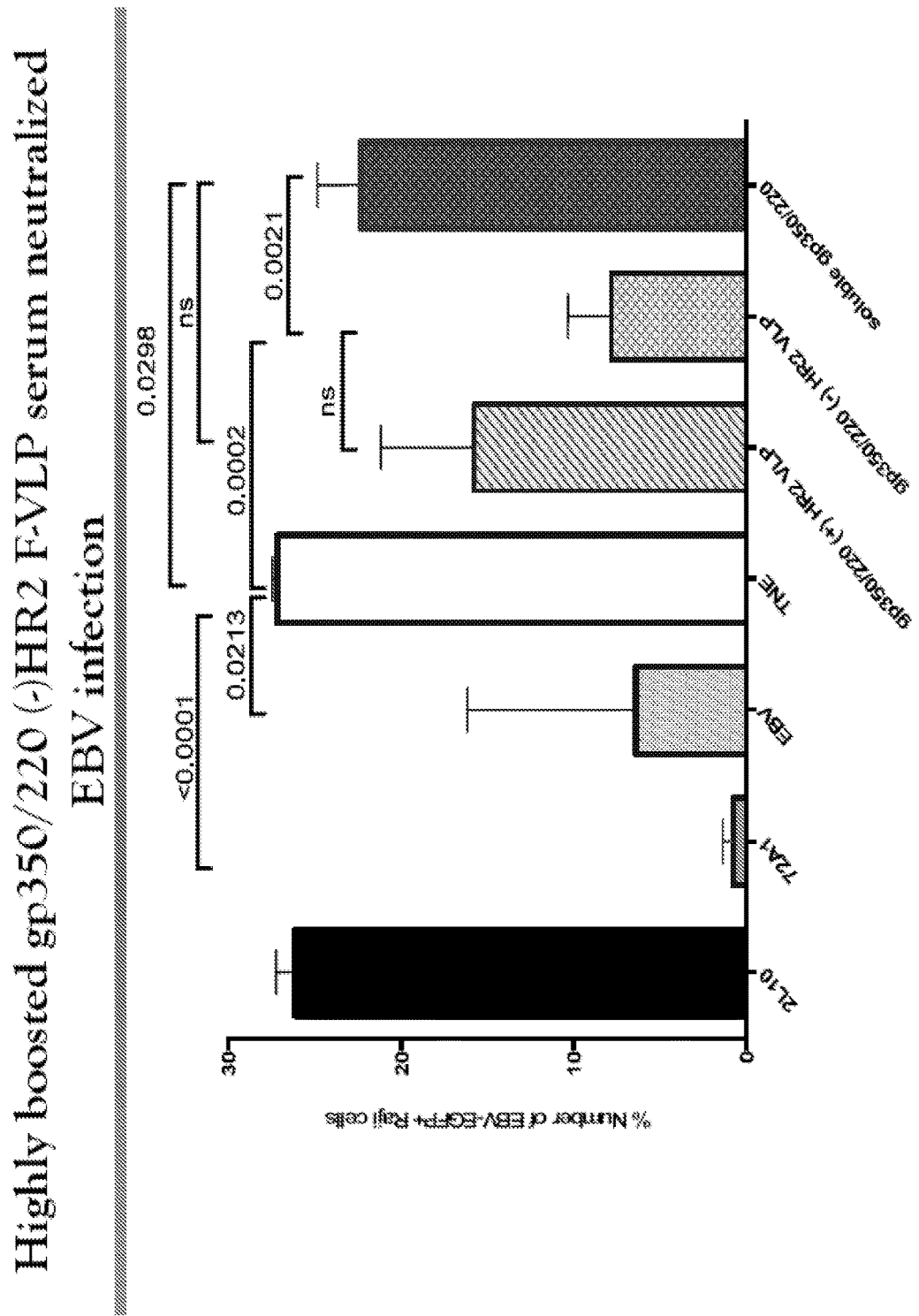
Figure 10:
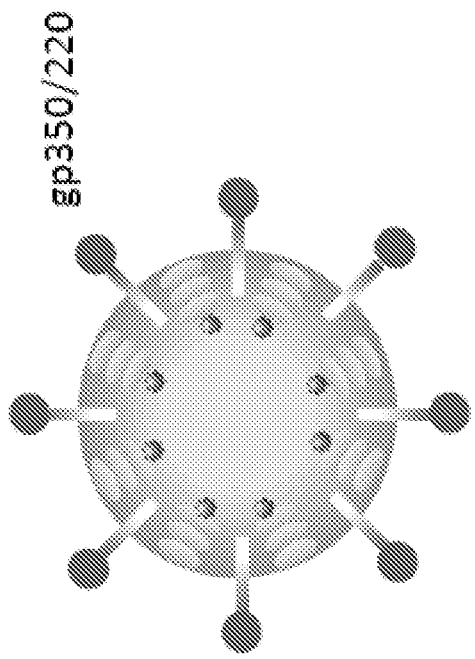
Figure 11:
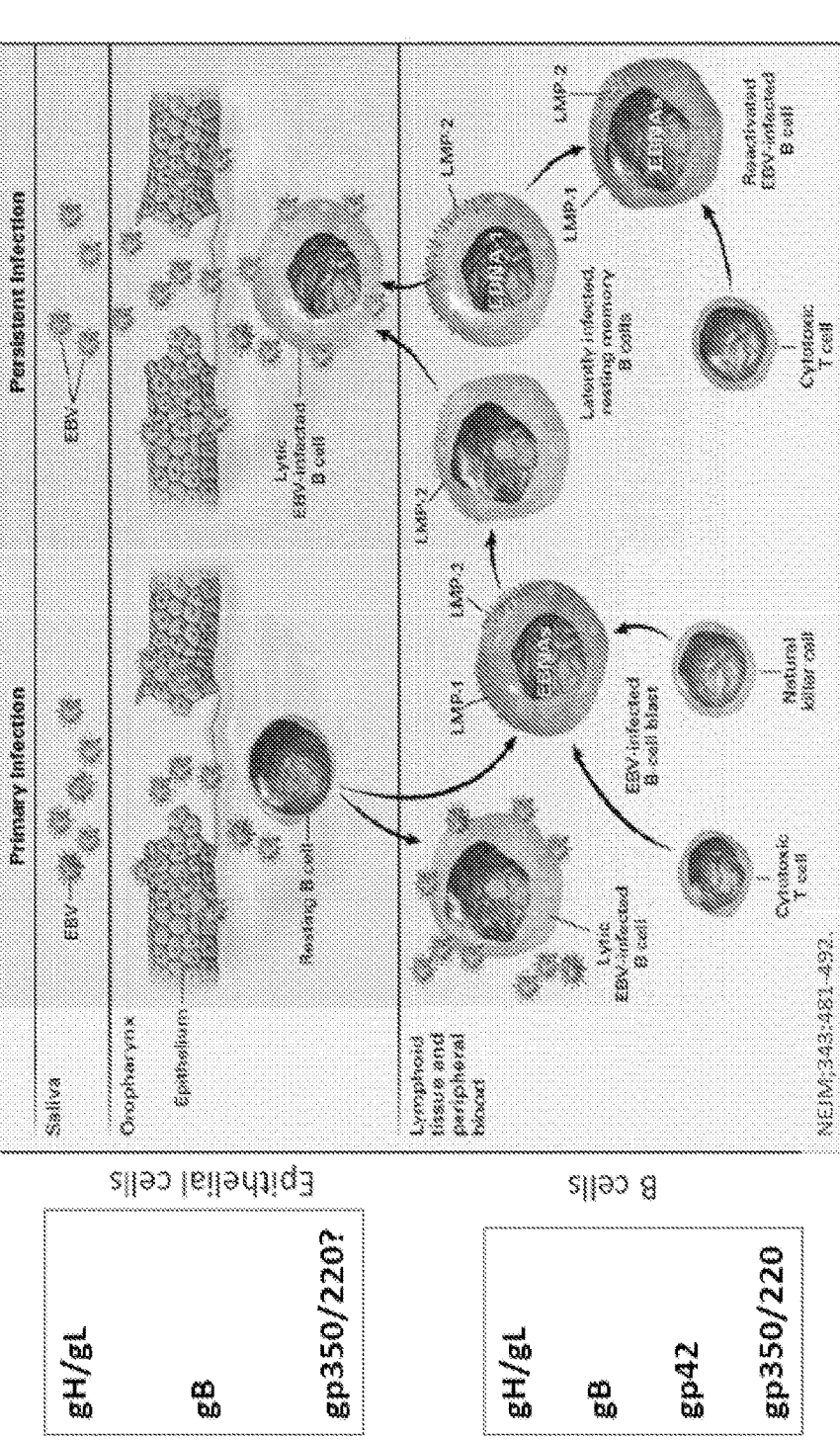
Figure 15:
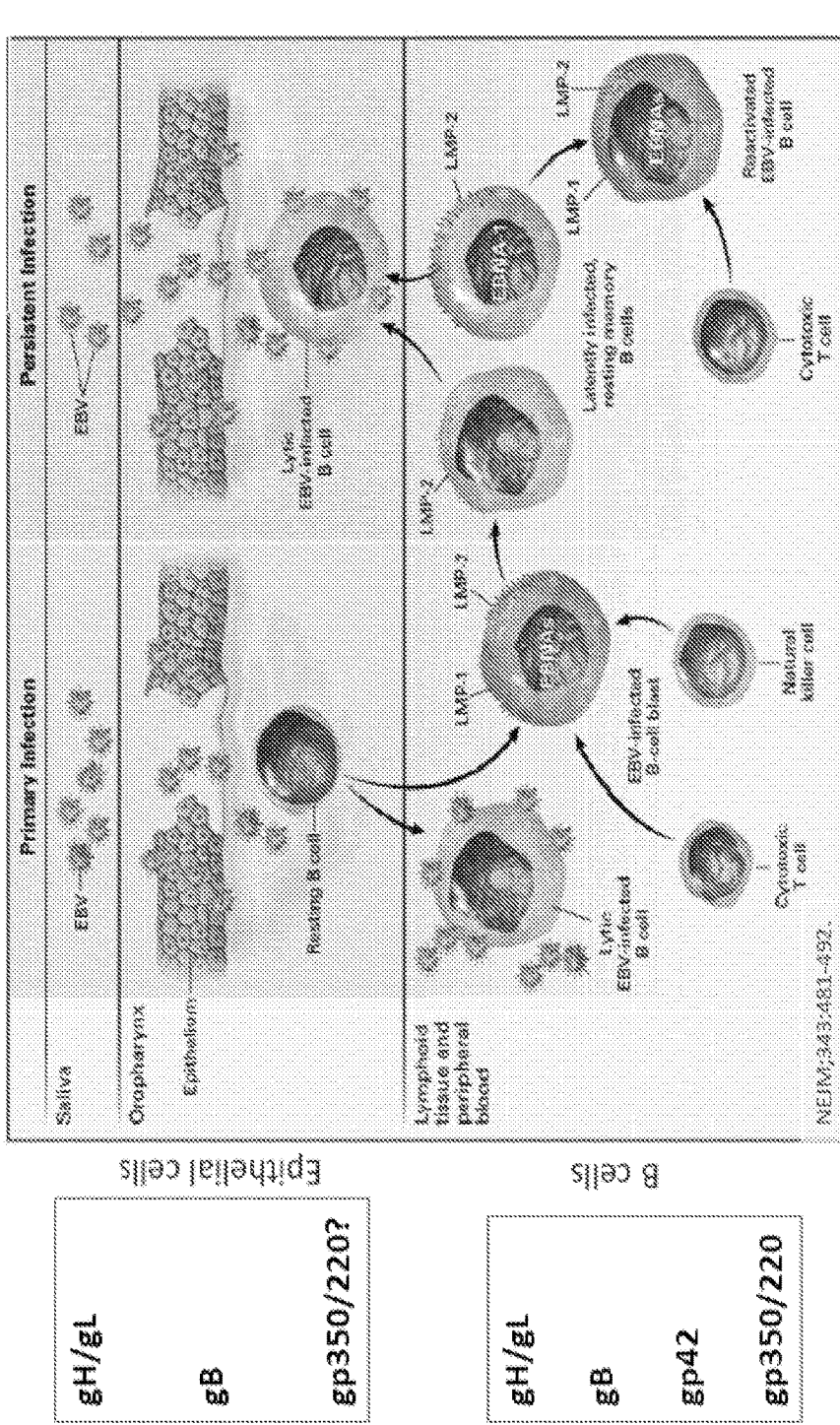
Figure 16:
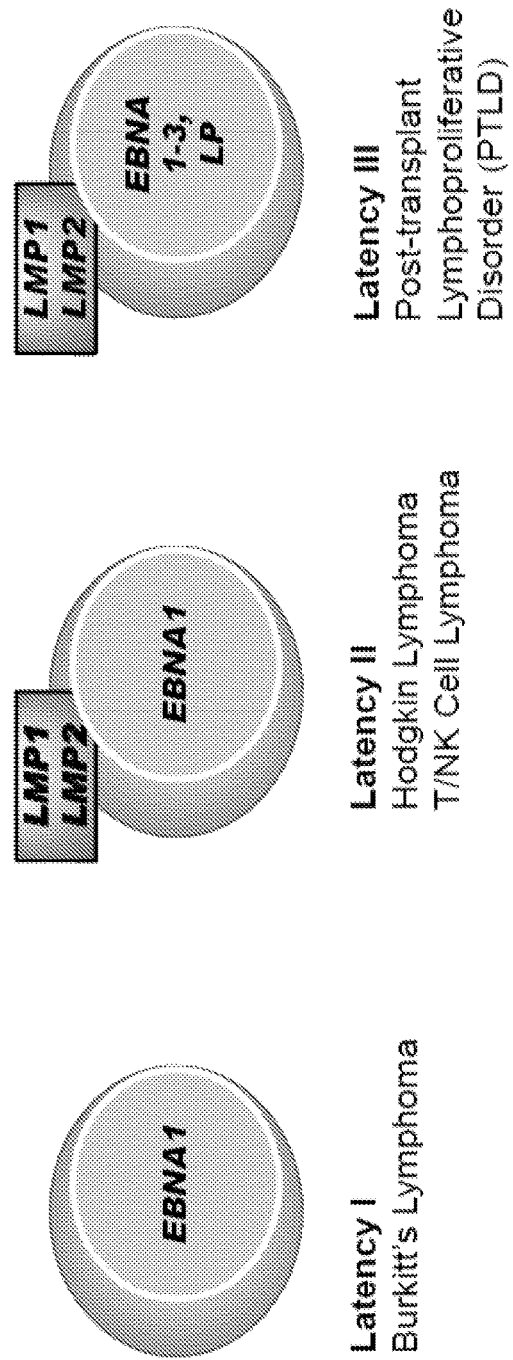
Figure 20:
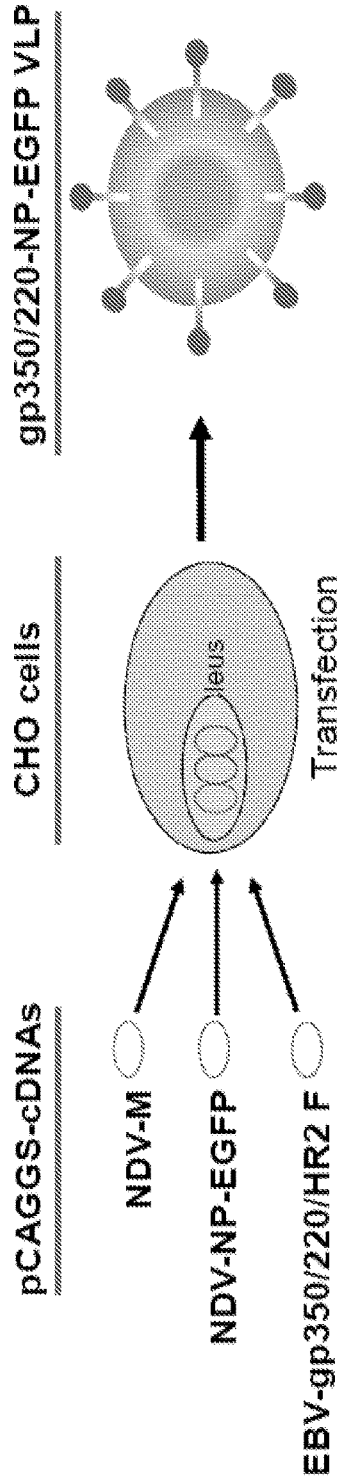
Figure 21:
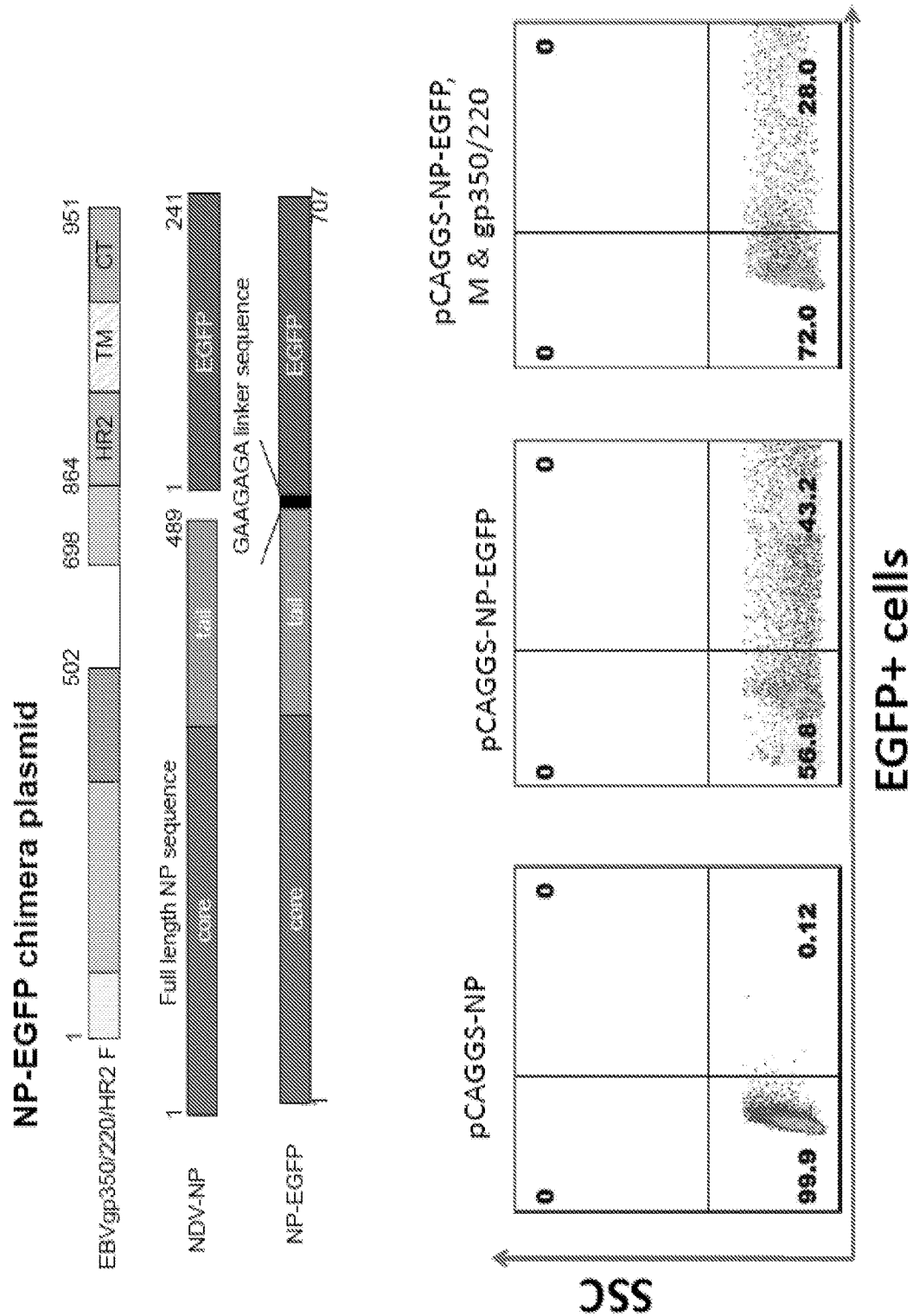
Figure 22:
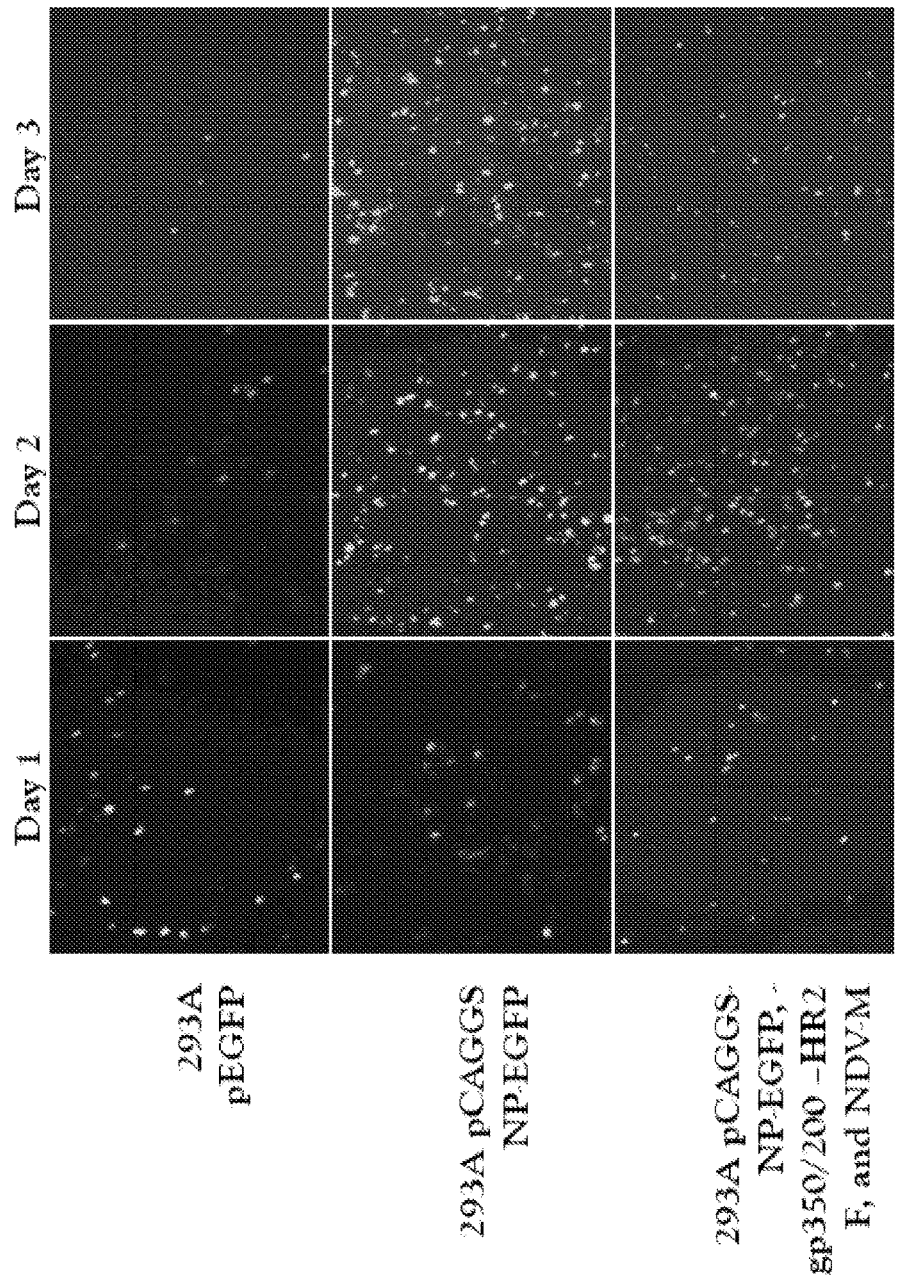
Figure 23:
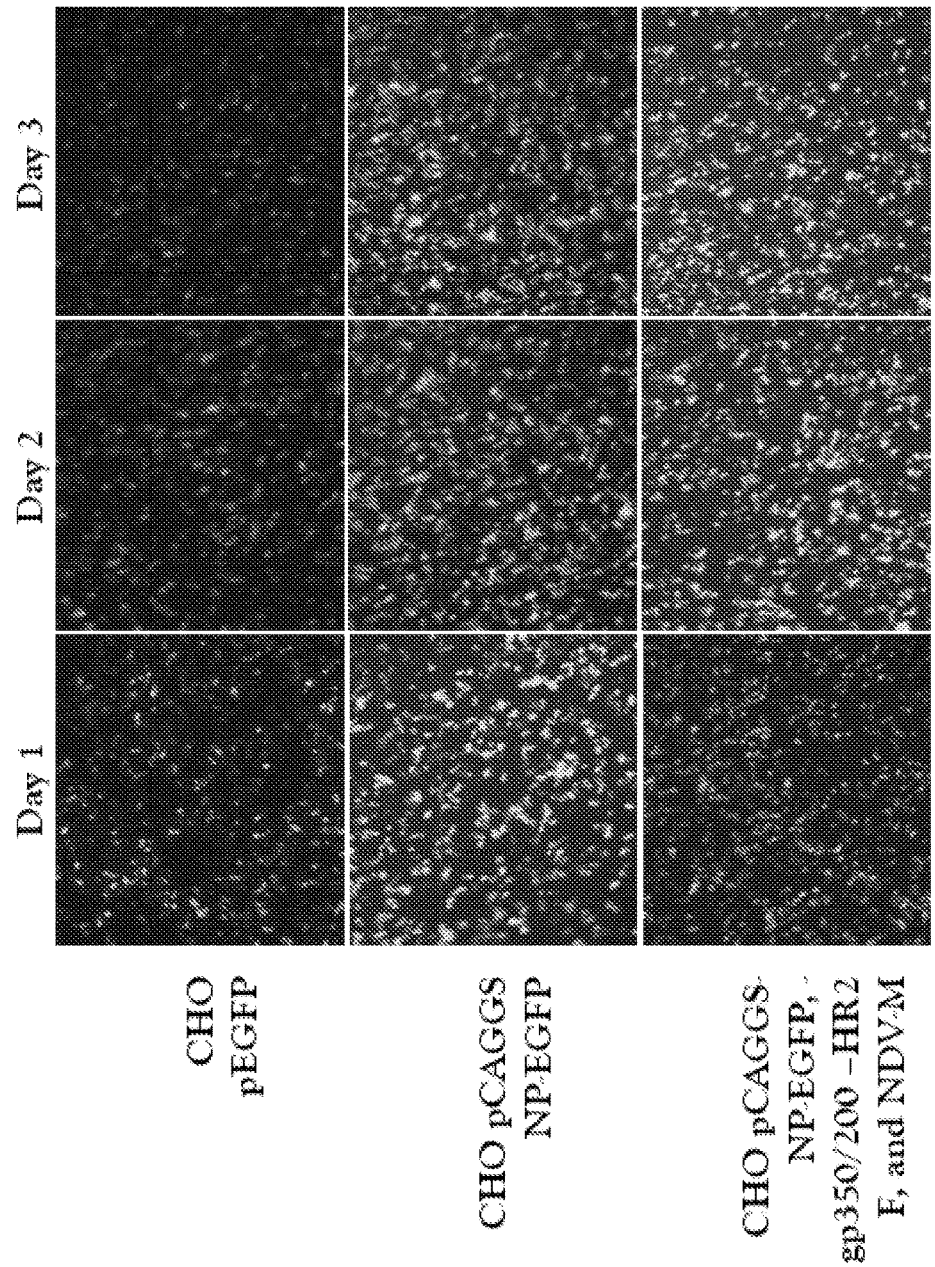
Figure 24:
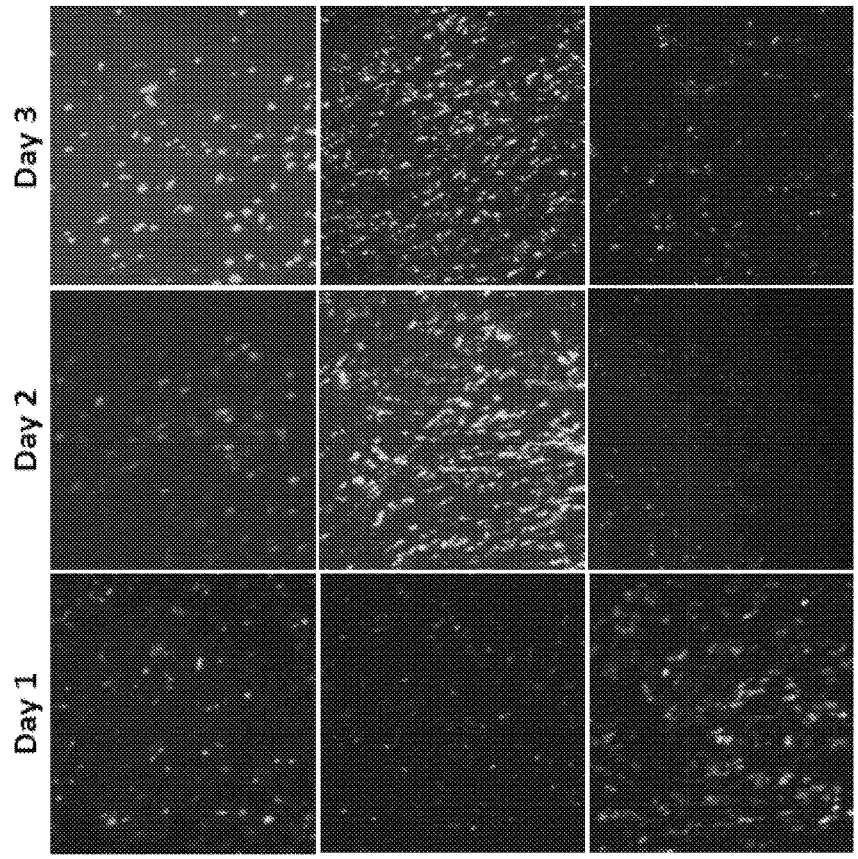
Figure 25:
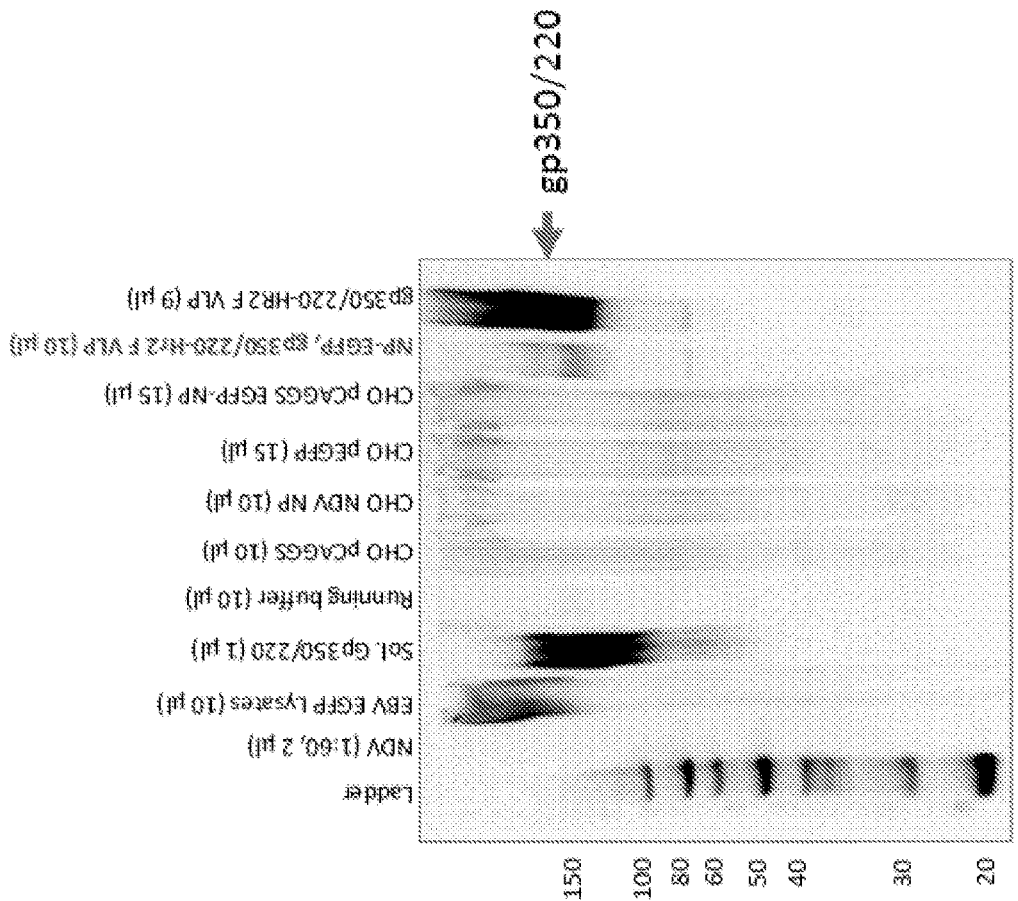
Figure 26:
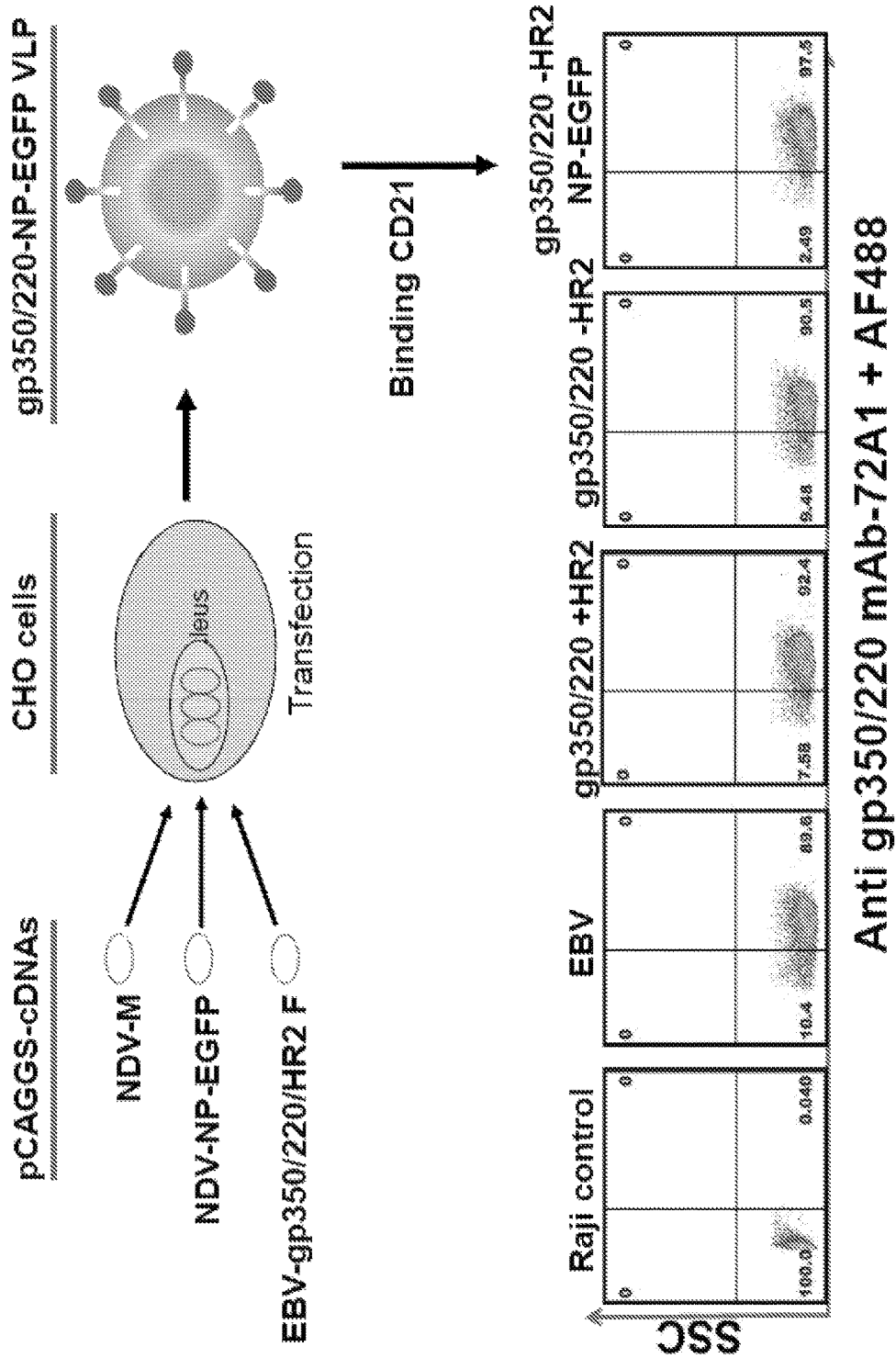
Figure 27:
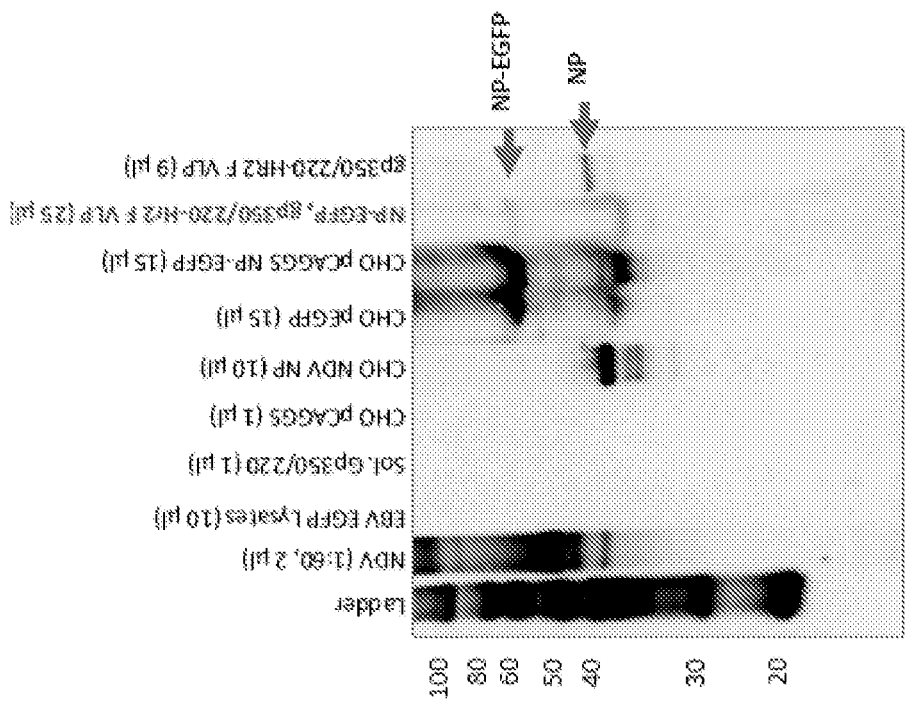
Figure 28:
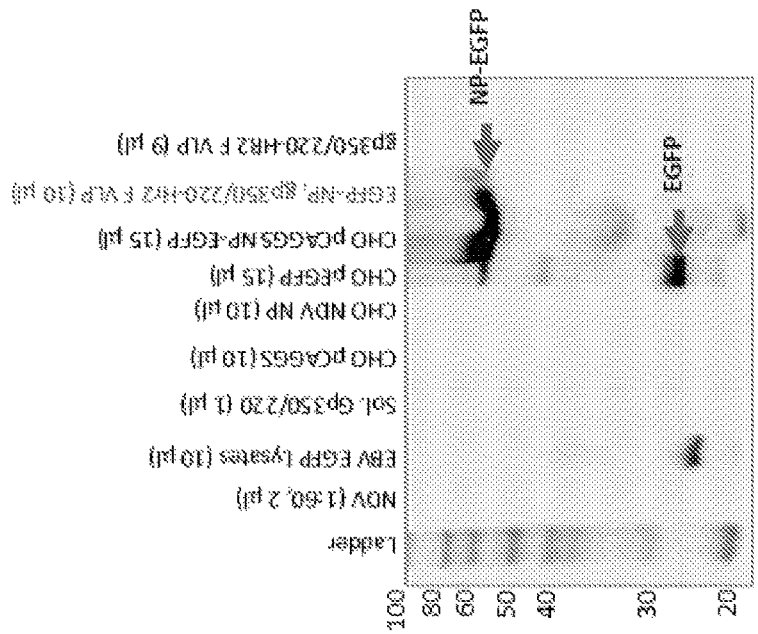
Figure 30:
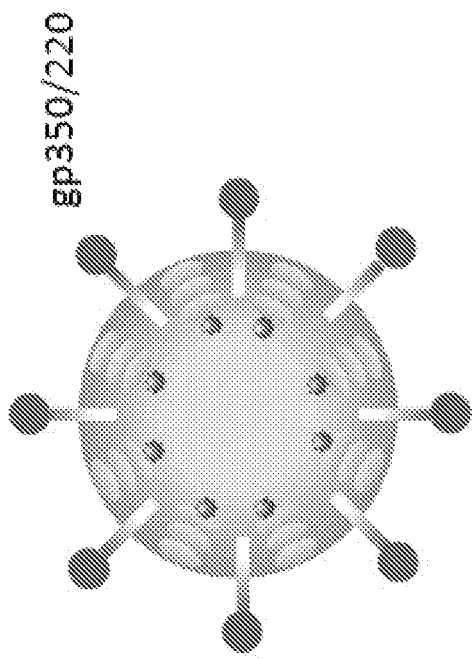
Figure 31:
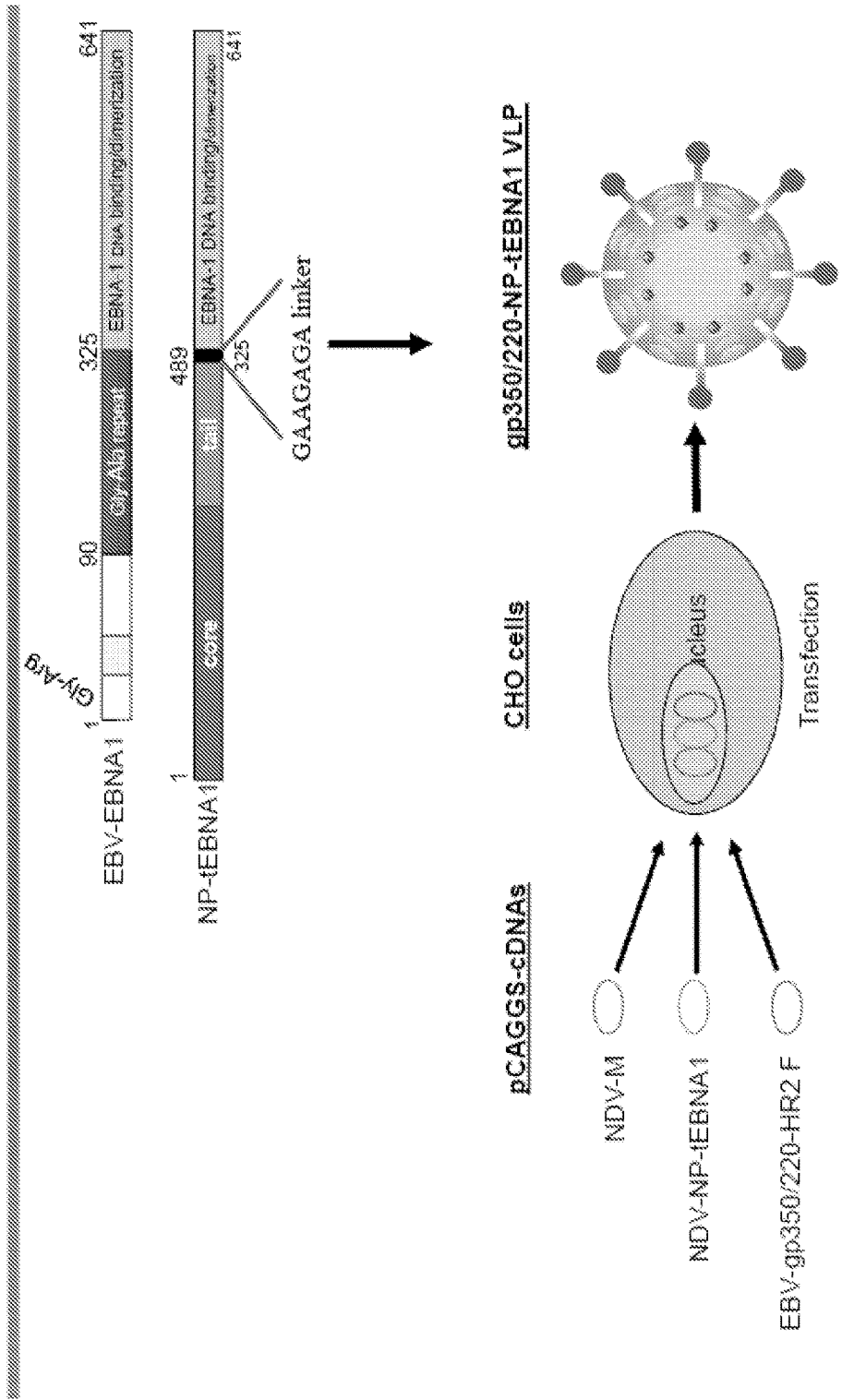
Figure 32:
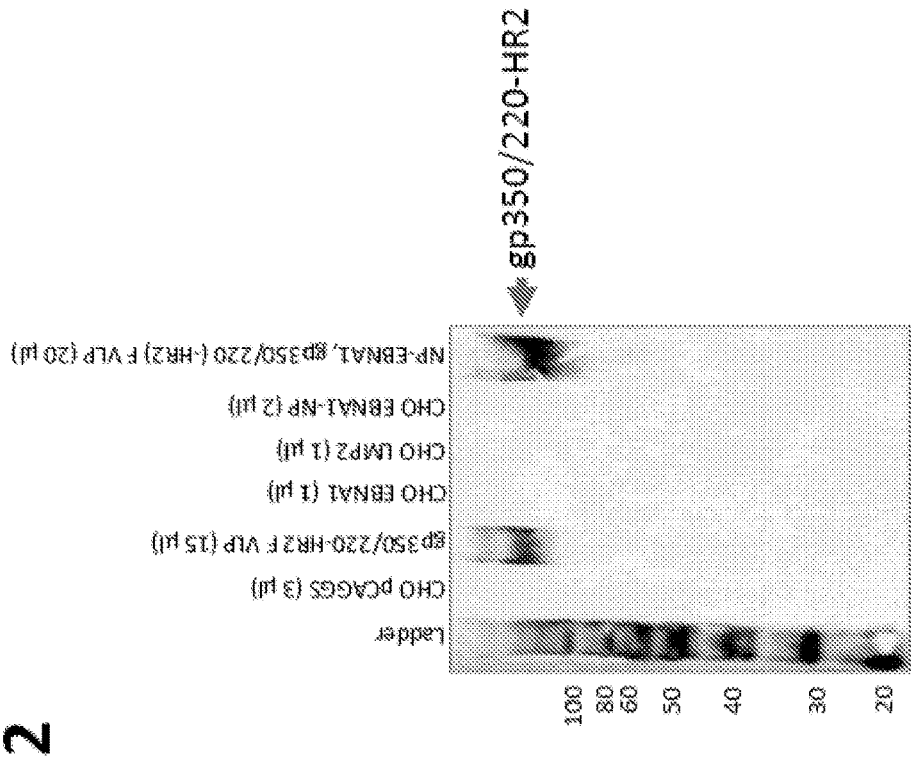
Figure 33:
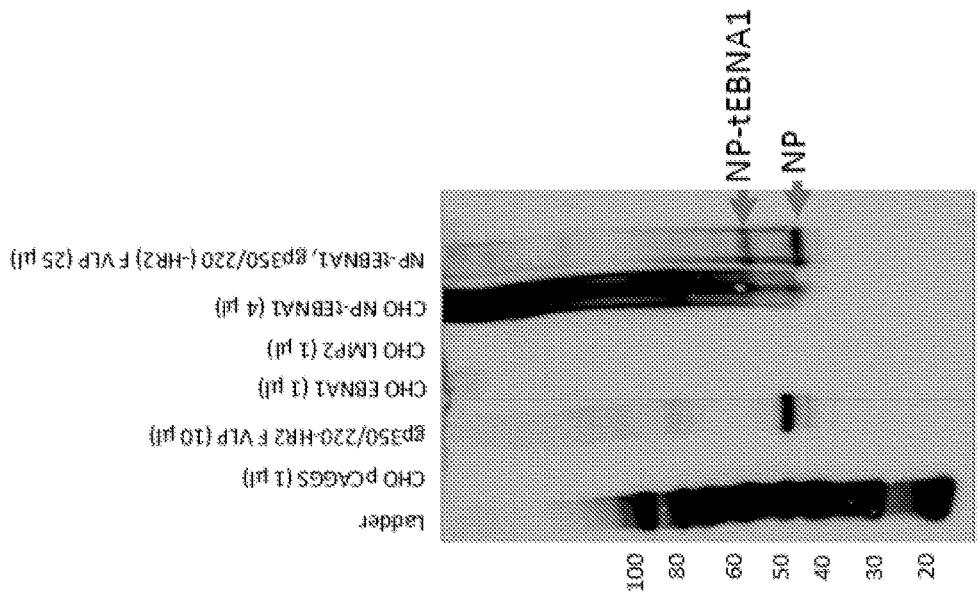
Figure 34:
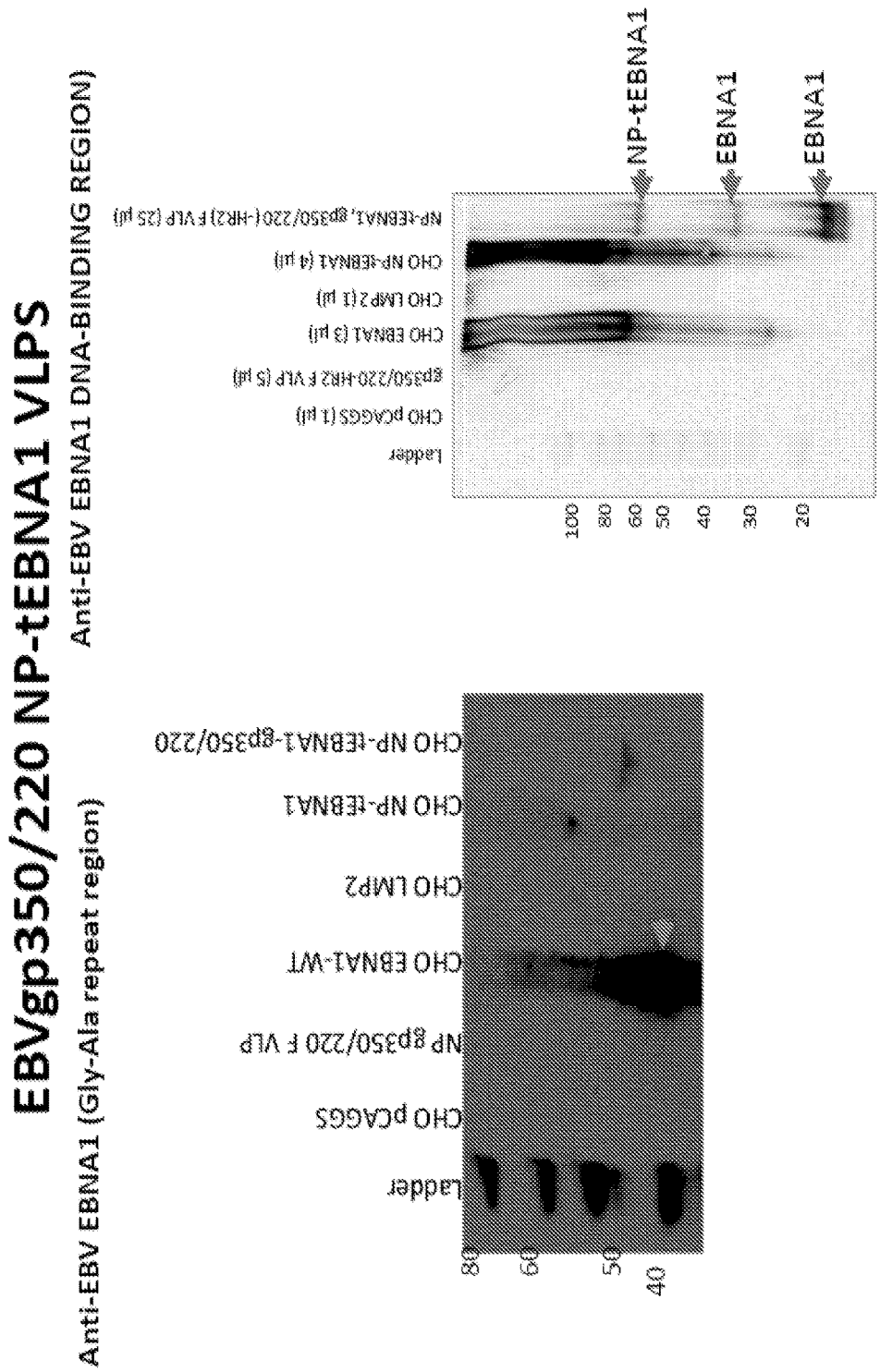

"EBNA1" is exemplified in FIG. 8 by human herpesvirus 4 SEQ ID NO:08, NCBI Reference Sequence: YP_401677.1.

Figure 50:
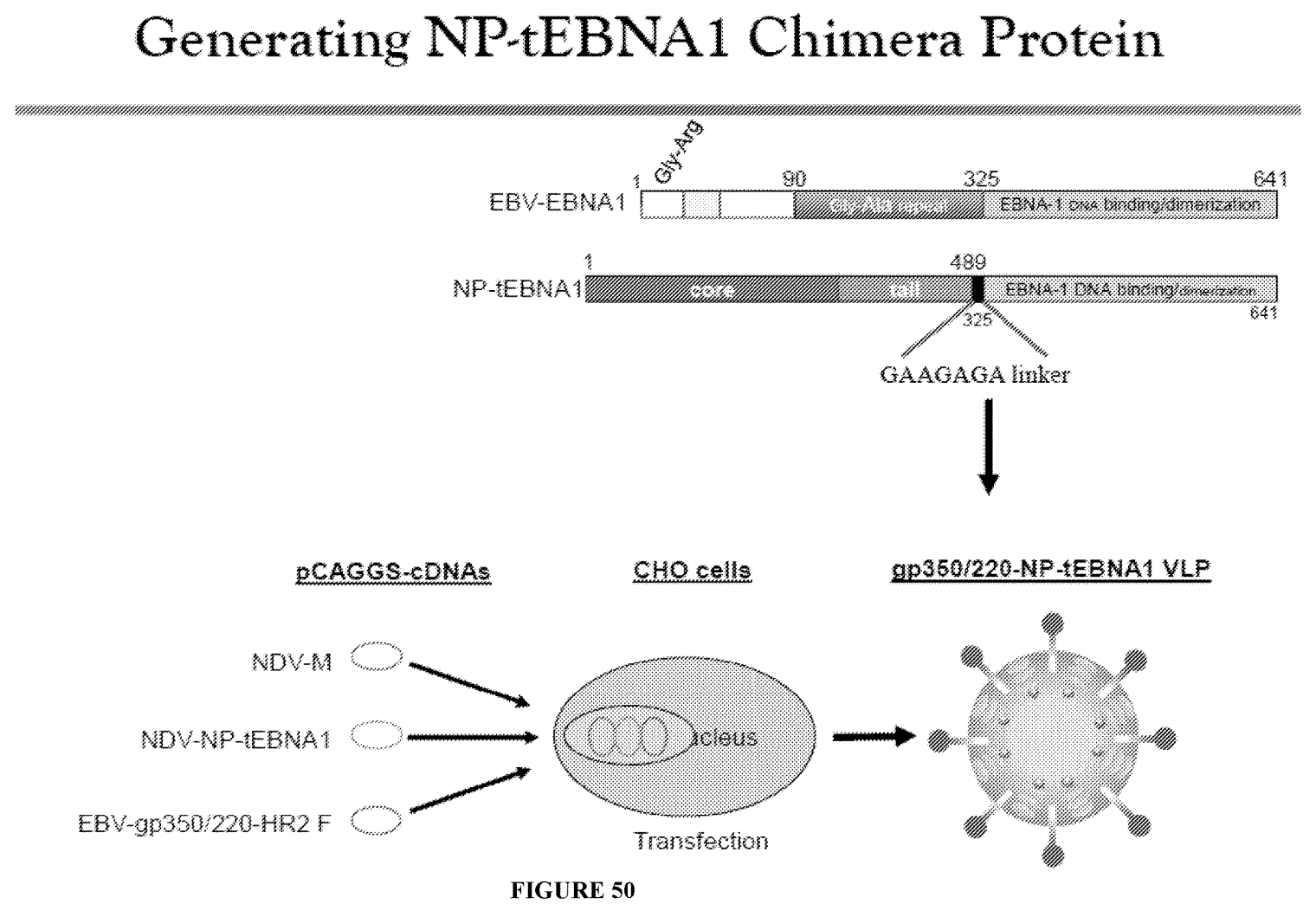
Figure 52:
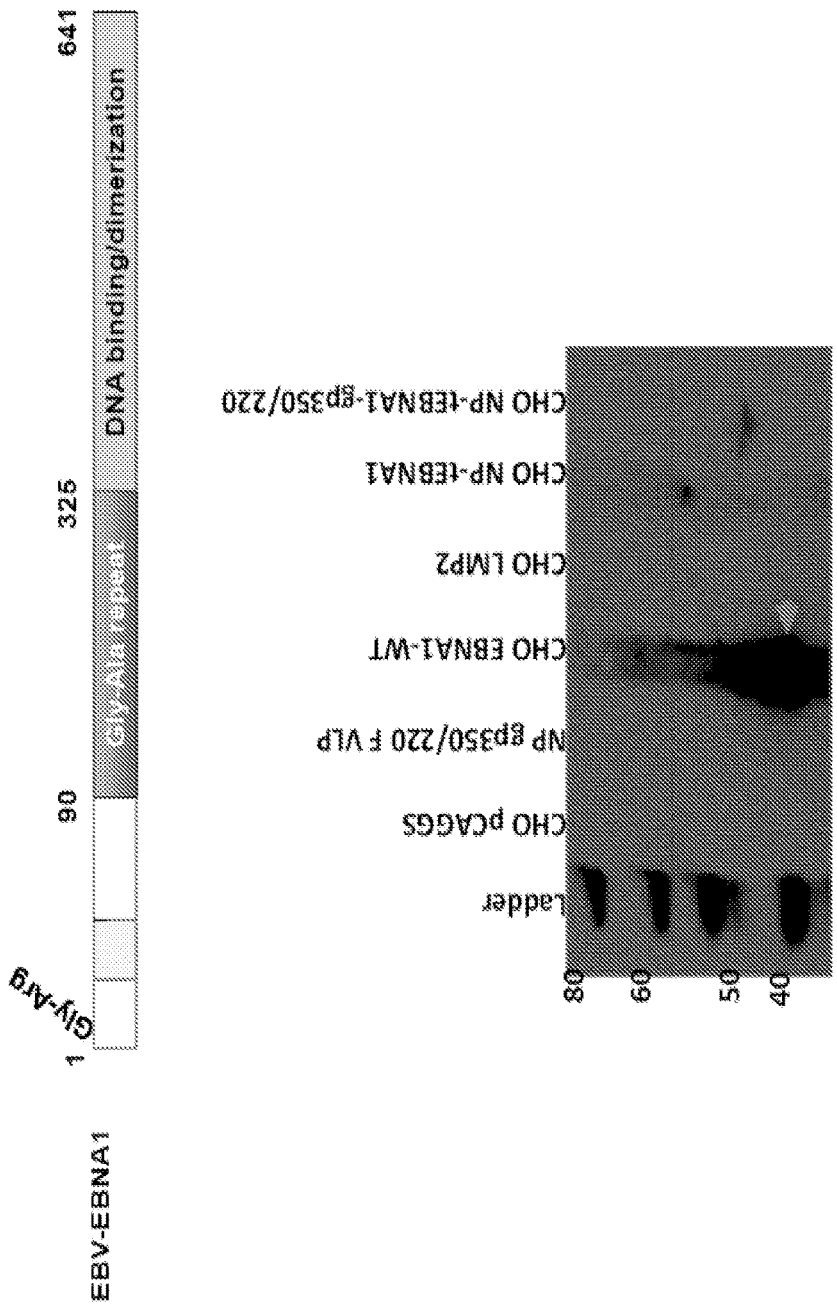
Figure 53:
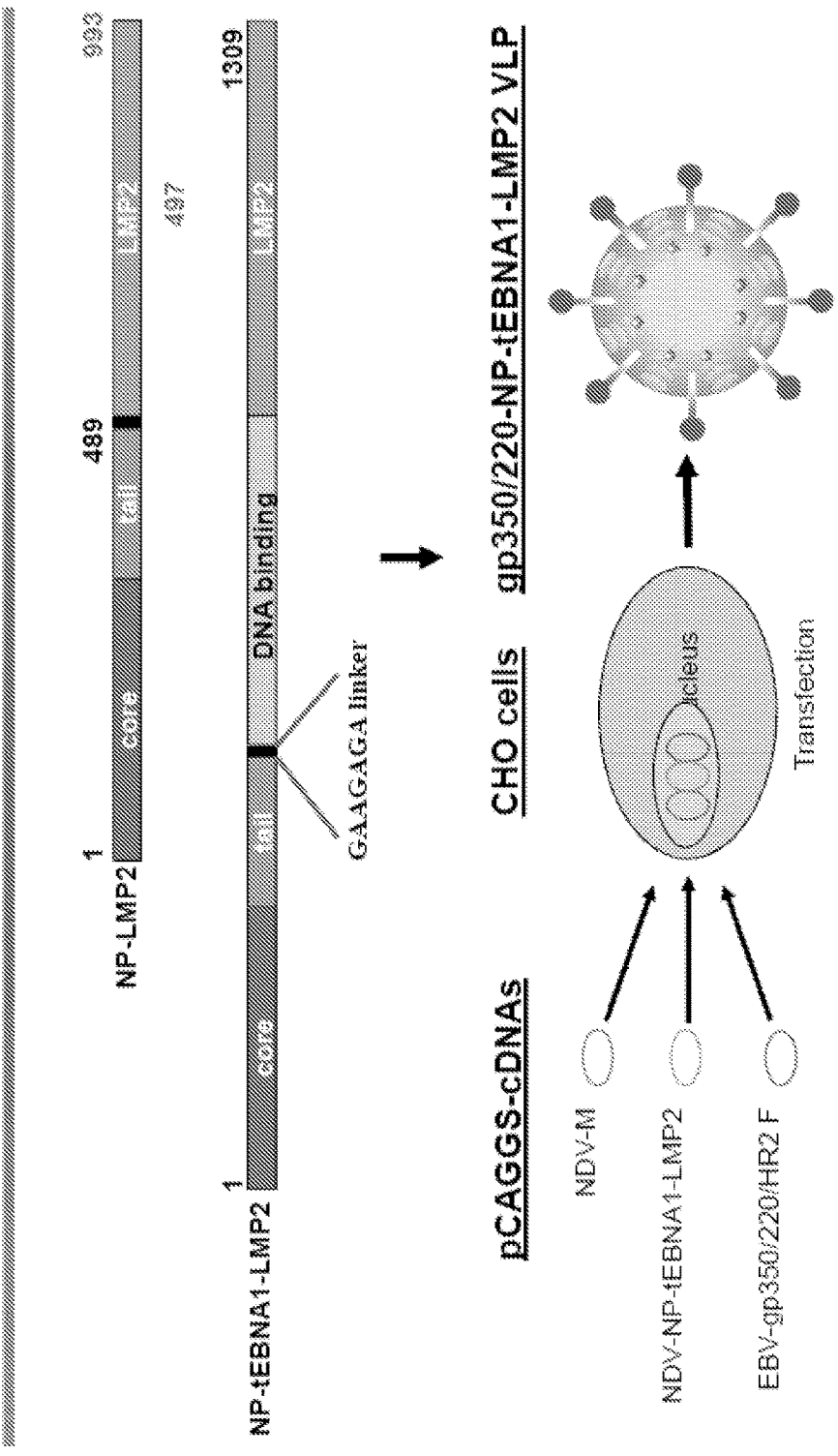
Figure 62:
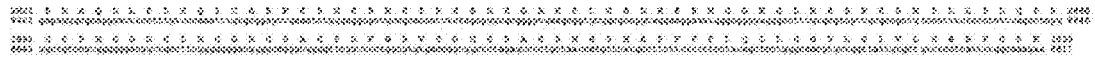
FIG. 62. EBNA-1_326-641 LMP2 NP in NDV NP in pCAGGS.SEQ Translation
Figure 67:
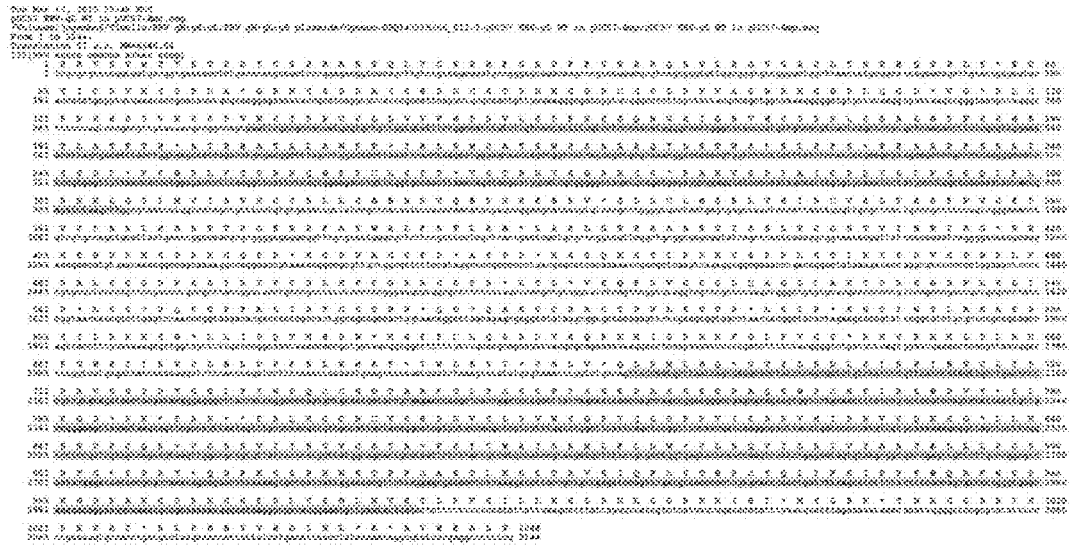
FIG. 67. pUC57 EBV-gL WT in pUC57-Amp.seq Translation
Figure 68:
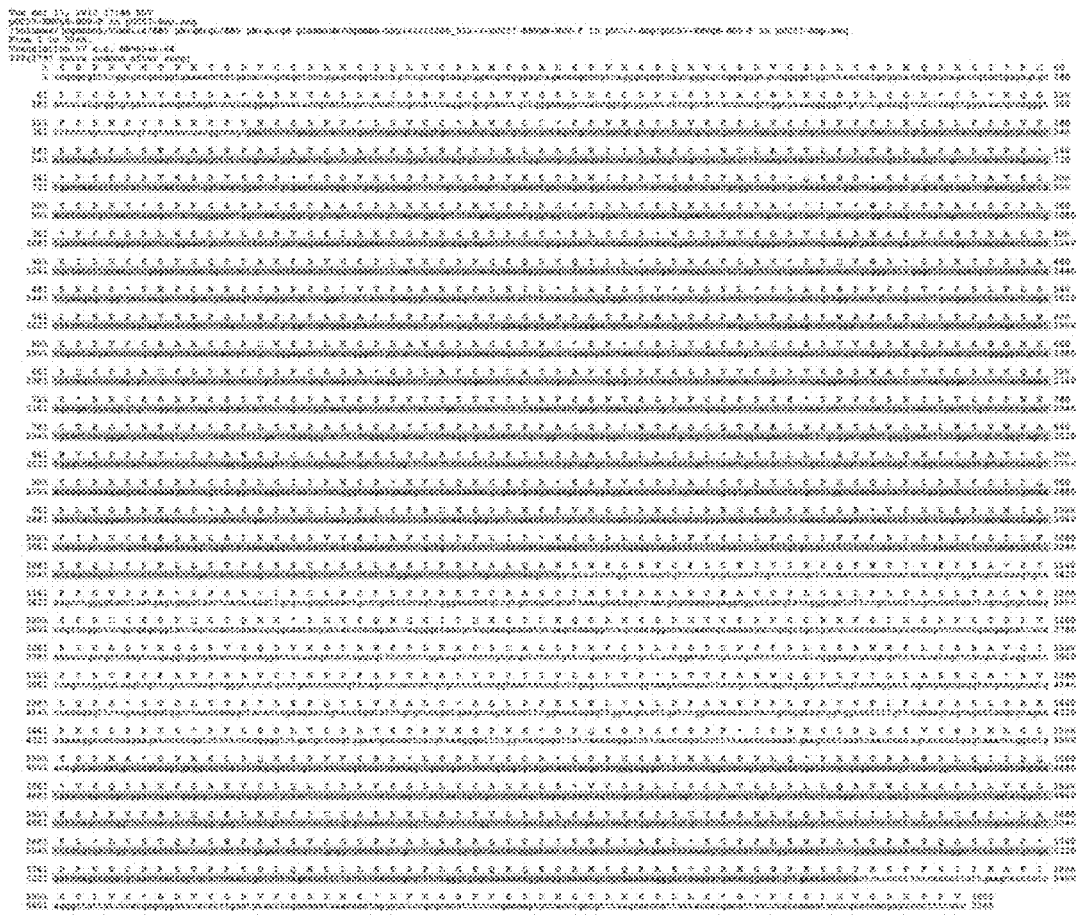
FIG. 68. pUC57-EBVgB-NDV-F in pUC57-Amp.seq Translation

"Truncated EBNA" and "tEBNA1" interchangeably refer to EBNA1 that lacks the Gly-Ala rich domain known to impair presentation of cis-linked sequences, and are exemplified by the sequence from amino acid 325-641 of FIG. 8's EBNA SEQ ID NO:08. Constructs containing tEBNA1 are exemplified in FIGS. 50 and 52.

"LMP2" is exemplified in FIG. 54 by the terminal protein LMP2A of human herpesvirus 4 (SEQ ID NO:01), NCBI Reference Sequence: YP_401631.1.

"L1" is exemplified in FIG. 58 by human papillomavirus type 16 SEQ ID NO:05, GenBank: AAD33259.1.

"L2" is exemplified in FIG. 59 by human papillomavirus type 16 SEQ ID NO:06, GenBank: AAD33258.1, and in FIG. 60 by human papillomavirus type 18 SEQ ID NO:07, GenBank: AGG40790.1.

Physiologically acceptable "carrier" and "diluents" for vaccine preparation include water, saline solution, human serum albumin, oils, polyethylene glycols, aqueous dextrose, glycerin, propylene glycol or other synthetic solvents. Carriers may be liquid carriers (such as water, saline, culture medium, saline, aqueous dextrose, and glycols) or solid carriers (such as carbohydrates exemplified by starch, glucose, lactose, sucrose, and dextrans, anti-oxidants exemplified by ascorbic acid and glutathione, and hydrolyzed proteins).

The term "expression vector" refers to an nucleotide sequence containing a desired coding sequence and appropriate nucleic acid sequences necessary for the expression (i.e., transcription into RNA and/or translation into a polypeptide) of the operably linked coding sequence in a particular host cell. Expression vectors are exemplified by, but not limited to, plasmid, phagemid, shuttle vector, cosmid, virus, chromosome, mitochondrial DNA, plastid DNA, and nucleic acid fragments thereof. Nucleic acid sequences used for expression in prokaryotes include a promoter, optionally an operator sequence, a ribosome binding site and possible other sequences. Eukaryotic cells are known to utilize promoters, enhancers, and termination and polyadenylation signals.

"Mammalian subject" includes human, non-human primate, murine, ovine, bovine, ruminant, lagomorph, porcine, caprine, equine, canine, felines, ave, etc.).

A subject "in need" of reducing one or more symptoms of a disease, and/or "in need" for a particular treatment (such as immunization) against a disease includes a subject that exhibits and/or is at risk of exhibiting one or more symptoms of the disease. For Example, subjects may be at risk based on family history, genetic factors, environmental factors, etc. This term includes animal models of the disease. Thus, administering a composition (which reduces a disease and/or which reduces one or more symptoms of a disease) to a subject in need of reducing the disease and/or of reducing one or more symptoms of the disease includes prophylactic administration of the composition (i.e., before the disease and/or one or more symptoms of the disease are detectable) and/or therapeutic administration of the composition (i.e., after the disease and/or one or more symptoms of the disease are detectable). The invention's compositions and methods are also useful for a subject "at risk" for disease refers to a subject that is predisposed to contracting and/or expressing one or more symptoms of the disease. This predisposition may be genetic (e.g., a particular genetic tendency to expressing one or more symptoms of the disease, such as heritable disorders, etc.), or due to other factors (e.g., environmental conditions, exposures to detrimental compounds, including carcinogens, present in the environment, etc.). The term subject "at risk" includes subjects "suffering from disease," i.e., a subject that is experiencing one or more symptoms of the disease. It is not intended that the present invention be limited to any particular signs or symptoms. Thus, it is intended that the present invention encompass subject that are experiencing any range of disease, from sub-clinical symptoms to full-blown disease, wherein the subject exhibits at least one of the indicia (e.g., signs and symptoms) associated with the disease.

"Immunogenically effective amount" refers to that amount of a molecule that elicits and/or increases production of an "immune response" (i.e., production of specific antibodies and/or induction of a cytotoxic T lymphocyte (CTL) response) in a host upon vaccination with the molecule.

"Antibody" refers to an immunoglobulin (e.g., IgG, IgM, IgA, IgE, IgD, etc.) and/or portion thereof that contains a "variable domain" (also referred to as the "$F_v$ region") that specifically binding to an antigen.

The term "specifically binds" and "specific binding" when made in reference to the binding of antibody to a molecule (e.g., peptide) or binding of a cell (e.g., T-cell) to a peptide, refer to an interaction of the antibody or cell with one or more epitopes on the molecule where the interaction is dependent upon the presence of a particular structure on the molecule. For example, if an antibody is specific for epitope "A" on the molecule, then the presence of a protein containing epitope A (or free, unlabeled A) in a reaction containing labeled "A" and the antibody will reduce the amount of labeled A bound to the antibody. In one embodiment, the level of binding of an antibody to a molecule is determined using the "IC50" i.e., "half maximal inhibitory concentration" that refer to the concentration of a substance (e.g., inhibitor, antagonist, etc.) that produces a 50% inhibition of a given biological process, or a component of a process (e.g., an enzyme, antibody, cell, cell receptor, microorganism, etc.). It is commonly used as a measure of an antagonist substance's potency.

SUMMARY OF THE INVENTION the invention provides a recombinant virus-like particle (VLP) comprising, in operable combination, a) Newcastle disease virus (NDV) matrix (M) protein, b) NDV nucleocapsid (NP) protein, and c) one or more tumor-associated EBV antigen, wherein said one or more tumor-associated EBV antigen is inside said VLP. In one embodiment, said tumor-associated EBV antigen is selected from the group consisting of EBNA1, tEBNA1 and LMP2. In a further embodiment, said tumor-associated EBV antigen comprises tEBNA1 and LMP2. In another embodiment, the VLP further comprises, in operable combination, one or more Epstein-Barr Virus (EBV) antigens, wherein at least one of said one or more antigens is selected from the group consisting of gB, gH, and gL. In yet another embodiment, said VLP further comprises, in operable combination, EBV gp350/220. In one embodiment, said VLP further comprises, in operable combination, one or more NDV proteins. In a further embodiment, said one or more NDV proteins comprise NDV heptad repeat domain 2 (HR2) protein. In one embodiment, said one or more NDV proteins comprise NDV fusion (F) protein. In another embodiment, said one or more NDV proteins comprise NDV heamagglutinin-neuraminidase (HN) protein. In yet another embodiment, the VLP further comprises, in operable combination, one or more human papillomavirus antigens. In yet another embodiment, said one or more human papillomavirus antigens comprises one or more of L1 and L2.

The invention also provides a vaccine comprising any one or more of the VLPs described herein, and a physiologically acceptable carrier.

Also provided by the invention is an expression vector encoding any one or more of the recombinant VLPs described herein.

The invention additionally provides a method for immunizing a mammalian subject against cancer, comprising administering an immunologically effective amount of one or more vaccine of Claim 12 to a mammalian subject in need thereof to produce a treated subject, wherein said administering is under conditions to produce an immune response to one or more tumor-associated EBV antigen. In one embodiment, said cancer comprises an Epstein-Barr Virus (EBV)-associated cancer. In another embodiment, said EBV-associated cancer comprises cervical cancer. In one embodiment, said immune response comprises T lymphocytes that specifically bind to said one or more tumor-associated EBV antigen. In a further embodiment, said immune response lacks antibody that specifically binds to said one or more tumor-associated EBV antigen. In yet another embodiment, said T lymphocytes are selected from CD4$^+$ lymphocytes and CD8$^+$ lymphocytes. In a further embodiment, said method further comprises administering a recombinant VLP that contains, in operable combination, a) Newcastle disease virus (NDV) matrix (M) protein, and b) EBV gp350/220. In another embodiment, said method further comprises one or more of a) detecting said immune response to said one or more tumor-associated EBV antigen, and b) detecting a reduction in one or more symptoms of said cancer in said treated subject. In one particular embodiment, said administering is before manifestation of one or more symptoms of said cancer. In another embodiment, said administering is after manifestation of one or more symptoms of said cancer.

DESCRIPTION OF THE INVENTION

The present invention provides prophylactic and/or therapeutic vaccines that contain Newcastle disease virus (NDV) virus-like particles (VLPs) comprising one or more Epstein-Barr Virus (EBV) antigens. The invention's prophylactic and/or therapeutic vaccines are useful for preventing and/or treating infection with EBV and/or disease associated Epstein-Barr Virus, such as cancer.

In one embodiment, the invention relates to the use of virus-like particles (VLPs) as a multivalent vaccine for EBV, as well as the method of designing a producing these VLPs for this purpose. The VLPs stimulate both the production of nAbs (neutralizing antibodies) and EBV specific T-cells.

In one embodiment, the present invention involves the development of a safe and feasible method for generating VLPs to be used as a vaccine that targets both nAbs and to stimulate a T-cell response to viral antigens. Specifically, this invention uses the NDV platform to produce a multivalent vaccine to EBV, a worldwide virus associated with AIM and several cancers. In one embodiment, this process utilizes FDA-approved CHO cells to generate VLPs, mimic EBV on the surface, but do not contain viral DNA, avoiding safety concerns about the oncogenetic properties of the virus. Whereas past attempts have focused on inducing nAbs to gp350/220, which is required but not necessary for viral entry into the cell, in one embodiment, the invention's multivalent vaccine includes gH/gL and gB, both of which are necessary for the fusion and subsequent entry of EBV into both epithelial and B-cells (19, 22). In addition to these surface proteins, the VLPs can be used as a vehicle for latent EBV antigens, EBNA1 and LMP2, which an be used to generate CD4+ T-cells that are specific for these antigens.

A) Epstein-Barr Virus (EBV) and Current Approaches

Epstein-Barr virus (EBV) is an oncogenic herpesvirus infecting over 95% of the adult population globally. It is implicated in the development of various types of lymphoproliferative diseases (LPDs) and carcinomas (1). Every year, EBV infection is estimated to be responsible for ~200,000 cancers globally (2). In low-income settings, primary EBV infection typically occurs during early childhood and is thought to be largely asymptomatic. However, in malaria endemic regions, childhood acquisition poses an increased risk of EBV positive Burkitt lymphoma (BL) (1, 3, 4). In high-income settings, primary EBV infection is often delayed until adolescence (4); and causes acute infectious mononucleosis (AIM) in 50-70% of adolescents (3). Although the disease is self-limiting, prolonged forms of AIM or chronic active EBV infection, may leas to fatal outcomes (5) or significantly increase the risk of developing EBV positive Hodgkin lymphoma (1). EBV is also highly associated with nasopharyngeal and gastric carcinomas, reflecting the epithelial tropism of the virus (3). Among infected individuals, EBV is controlled by T-cells and normally remains quiescent in memory B-cells (6). However, under conditions of immune suppression, the virus can reactivate, leading to an expansion of EBV-infected cells and increasing the likelihood of de novo infection, and transformation of infected B-cells as seen in BL, EBV positive post-transplant lymphoproliferative disorders (PTLDs), and AIDS-associated B-cell lymphomas (7-9). Management of EBV-associated diseases is problematic due to difficulties with diagnosis, surveillance, and treatment. In a meeting convened at the National Institute of Health (NIH) in 2011, participants agreed that the need for a safe and effective vaccine to prevent and/or treat EBV-associated diseases in urgent (2). Several strategies to generate an EBV vaccine based on viral glycoprotein 350/220 (gp350/220), latent membrane proteins (LMP1-2), and EBV nuclear antigen 1 (EBNA-1) are currently in experimental stages and/or clinical trials (10, 11). However, most of these strategies have low safety profiles, and are designed to elicit the production of neutralizing antibodies (nAbs) to EBV envelope proteins (prophylactic), or a T-cell response to latent EBV antigens (therapeutic). None of the current proposed vaccines address both arms of immunity in a single candidate vaccine. Our vaccine utilizes a VLP platform which incorporate select multiple viral surface glycoproteins in addition to intracellular T-cell antigens to generate a polyvalent vaccine. These VLPs have high safety profiles and are efficiently produced in the FDA-approved Chinese hamster ovary (CHO) cell line.

Antibodies (Abs) provide the first line of defense against virus infection. Neutralizing Abs directed to EBV envelope glycoproteins are present in humans, maternal nAbs prevent neonatal infection, and it has been shown that they are induced in response to immunization both in humans and in other animals (12-14). However, persistent EBV infection and the limited evidence of immune selection of viral antigenic variants indicate that in vivo neutralization of EBV infection is suboptimal. This was observed in four independent phase I/II clinical trials, in which vaccination with either vector constructs expressing gp350/220, or with purified recombinant non-splicing variant gp350 soluble protein, did not prevent infection although incidence of AIM was reduced in young adults by more than 70% (14-17). Importantly, primary B-cells can be infected with recombinant EBV lacking gp350/220; suggesting that additional viral ligands may be mediating EBV infection in the absence of gp350/220 (18-22). These observations indicate that using gp350/220 as the only immunogen (monovalent vaccine) to target viral neutralization is too simplistic and may account for the variable success in using this protein in EBV vaccine development.

In EBV infection, EBV gp350/220, the attachment protein, binds to B-cell receptors (CD21 and CD35, initiating the first contact of the virus and the host cells (23-26), and subsequently triggering endocytosis of the virions (27). This interaction enhances infection, but is not essential (18). Fusion between the viral envelope and the cellular membrane is a required step in the entry of all human herpesviruses (28). For EBV, the viral glycoproteins necessary for fusion of the viral envelope with the host cell receptors are glycoprotein B (gB) (22), the complex of gH and gL (gH/gL), and gp42 (19). These complexes mediate infection and confer host cell specificity. EBV entry into B-cells is mediated by gB, GH/gL, and gp42; whereas entry into epithelial cells is facilitated by interaction between gB and gH/gL (22, 29, 30). It is important to note that co-expression of EBVgH and gL is required for transport of gH to the cell surface which results in the formation of a stable complex of gH/gL (29). Recently, integrins have been identified as the epithelial receptors for EBVgH/gL and this interaction initiates fusion in a two-step cascade (20). Recombinant EBV lacking gH does not infect either epithelial or primary B-cells (31).

Although Abs to EBVgh/gL are not robustly produced in vivo during natural infection (perhaps due to masking by the immunodominant gp350/220), immunization of mice with recombinant gH can boost immunogenicity and generate Abs capable of blocking EBV infection (20, 21, 32). The ability of gH/gL Abs to neutralize infection is also well-conserved in herpes simplex virus-1 (33, 34), cytomegalovirus (35, 36) and Kaposi sarcoma herpesvirus (KSHV) (37). Monoclonal Abs to the gH protein or the gH/gL complex block EBV infection, indicating a critical role for gH/gL in EBV infection (38, 39). No specific nAbs to EBVgL or -gB have been reported so far (10). NAbs directed to EBVgp42, have been identified (40).

T-cell-mediated responses are effective in controlling persistent EBV infection, as evidenced by some form of immunosuppression usually preceding EBV-associated lymphomas and PTLDs (1, 41). Furthermore, adoptive transfer of EBV-specific T-cells can induce remission in transplant patients (42, 43).

The current hypothesis is that protection against EBV relies on inducing $CD4^+$ and $CD8^+$ T-cell immune responses, and the development of EBV therapeutic vaccine candidates have focused on enhancing such responses (44). EBNA1-specific $CD4^+$ and $CD8^+$ T-cells are frequently detected in EBV-infected individuals (45, 46), and both T-cell subsets can be effective in controlling growth of EBV-immortalized B-cells (47). Notably, EBNA1, LMP2, and EBVgp350/220 antigens have been developed and independently tested in various clinical trials as vaccine candidates against EBV infection and $EBV^+$ cells with promising results (17, 48, 49). Recent phase I clinical trials of recombinant modified vaccinia Ankara vector encoding deletion of Gly-Ala regions from the EBNA1 sequence (known to impair presentation of cis-linked sequences) fused to LMP2 as a vaccine candidate elicited a robust EBV-specific $CD4^+$ and $CD8^+$ T-cell response in humans (44, 48, 50). However, the strategy used to deliver these two important EBV antigens (a DNA vaccine), known for their oncogenic potential, may pose major health risks, such as inducing an antibody response to DNA or integration of DNA in an undesired location in the host genome causing unchecked cell growth, particularly in immunosuppressed individuals. Furthermore, these vaccine candidates cannot elicit nAbs to eliminate reactivated or new EBV infections. There is also a risk of vaccine tolerance since the quantity of proteins produced and secreted in vivo is unregulated. EBV DNA packaging mutants (51), and disabled virions that lack the major oncoproteins have also been proposed as an alternative strategy (52).

However, incomplete knowledge of all the virion proteins functions, concerns about inadvertent association of oncogenic DNA/RNA fragments with the assembled VLPs, limited production and release of the virus, as well as current requirements for their propagation in transformed human cell lines suggest that such strategies may not meet the stringent FDA safety guidelines. Our strategy will address all these limitations by combining select multiple EBV antigens in a VLP platform which is efficiently produced in CHO cells, immunogenic, and safe to use in all populations, irrespective of immune status.

B) Compositions and Methods for Treating Cancer

The invention provides prophylactic and/or therapeutic vaccines that contain Newcastle disease virus (NDV) virus-like particles (VLPs) comprising one or more tumor-associated Epstein-Barr Virus (EBV) antigens.

In one embodiment, the invention's VLPs induce both nAbs and protective human T-cell responses will not only be an invaluable candidate vaccine in preventing EBV infection, but also of utmost importance in preventing BL in African children, acute infectious mononucleosis in 50-70% of US adolescents, nasopharyngeal carcinoma (endemic in Southeast Asia), post-transplant lymphoproliferative disorders, and non-Hodgkin lymphoma (in iatrogenic and AIDS-immunodeficient patients). The Newcastle virus disease vaccine platform is also invaluable for the development of candidate prophylactic and therapeutic vaccines against other human viruses, as it provides a safe and effective method of targeting both arms of the immune system.

In one embodiment the invention provides a recombinant virus-like particle (VLP) comprising, in operable combination, a) Newcastle disease virus (NDV) matrix (M) protein, b) NDV nucleocapsid (NP) protein, and c) one or more tumor-associated EBV antigen, wherein the one or more tumor-associated EBV antigen is inside the VLP. In one embodiment, the tumor-associated EBV antigen is selected from the group consisting of EBNA1, tEBNA1 and LMP2. In one embodiment, the tumor-associated EBV antigen comprises tEBNA1 and LMP2. In one embodiment, the VLP further comprises, in operable combination, one or more Epstein-Barr Virus (EBV) antigens, wherein at least one of the one or more antigens is selected from the group consisting of gB, gH, and gL. In one embodiment, the VLP further comprises, in operable combination, EBV gp350/

220. In one embodiment, the VLP further comprises, in operable combination, one or more NDV proteins, exemplified by, NDV HR2 protein, NDV F protein, and NDV HN protein. In one embodiment, the VLP, further comprises, in operable combination, one or more human papillomavirus antigens. In one embodiment, the one or more human papillomavirus antigens comprises one or more of L1 and L2.

The invention also provides a vaccine comprising one or more of any of the VLPs described herein, and a physiologically acceptable carrier.

The invention also provides an expression vector encoding any one or more of the recombinant VLPs described herein.

The invention also provides a method for immunizing a mammalian subject against cancer, comprising administering an immunologically effect amount of any one or more of the vaccines described herein to a mammalian subject in need thereof to produce a treated subject, wherein the administering is under conditions to produce an immune response to one or more tumor-associated EBV antigen. In one embodiment, the cancer comprises an Epstein-Barr Virus (EBV)-associated cancer. In one embodiment, the EBV-associated cancer comprises cervical cancer. In one embodiment, the immune response comprises T lymphocytes that specifically bind to the one or more tumor-associated EBV antigen. In one embodiment, the immune response lacks antibody that specifically binds to the one or more tumor-associated EBV antigen. In one embodiment, the T lymphocytes are selected from $CD4^+$ lymphocytes and $CD8^+$ lymphocytes. In one embodiment, the method further comprises administering a recombinant VLP that contains, in operable combination, a) Newcastle disease virus (NDV) matrix (M) protein, and b) EBV gp350/220. In one embodiment, the method further comprises one or more of a) detecting the immune response to the one or more tumor-associated EBV antigen, and b) detecting a reduction in one or more symptoms of the cancer in the treated subject. In one embodiment, administering the vaccine is prophylactic before manifestation of one or more symptoms of the cancer. In one embodiment, administering the vaccine is therapeutic after manifestation of one or more symptoms of the cancer. In one embodiment, the vaccine prevents cancer and/or the spread of cancer.

C) Compositions and Methods for Immunizing Against Epstein-Barr Virus (EBV)

The invention provides prophylactic and/or therapeutic vaccines that contain Newcastle disease virus (NDV) virus-like particles (VLPs) comprising one or more Epstein-Barr Virus (EBV) antigens. The invention provides evidence that viral antigens capable of eliciting T cells response can be incorporated into the virus-like particle by fusing NDV-nucleoprotein.

Approaches to EBV vaccine development are limited due in part to the oncogenic potential of the EBV genome and a lack of animal models for testing vaccine candidates. VLPs are safe, immunogenic and have been successfully used to prevent infections against other oncogenic viruses such as human papillomavirus and hepatitis B virus. The EBV envelope glycoprotein gp350/220 (EBV gp350/220) has been proposed as a potential vaccine antigen. However, in four independent phase I/II clinical trials, vaccination with EBV gp350/220 did not prevent EBV infection. Importantly, recombinant EBV lacking gp350/220 can infect both epithelial and primary B cells in vitro. These preliminary studies demonstrate that using pooled sera from mice immunized four times with EBV gp350/220 VLPs without adjuvants neutralized EBV infection in vitro, resulting in 46% inhibition. Whereas neutralization with sera from mice immunized with UV-inactivated EBV resulted in ~88% inhibition. This suggests that other envelope glycoproteins may have a role in virus entry, independent of gp350/220. The EBVgH/gL envelope glycoprotein complex is definitively required for EBV fusion and entry, and thus is a potential target for developing a prophylactic vaccine. Antibodies to the EBV gH/gL complex can neutralize virus infection, and recombinant EBV lacking gH cannot infect both epithelial and primary B cells. To our knowledge, these proteins have not yet been tested as part of candidate vaccines in any animal model or clinical trial.

Data herein provides evidence that generation of VLPs containing both EBV gH/gL and EBV EBNA1 and/or LMP2 consistently expressed in most EBV positive tumors is feasible. Recent phase I clinical trials of recombinant modified vaccinia Ankara vector encoding deletion of Gly-Ala regions from the EBNA1 sequence fused to LMP2 as a vaccine candidate elicited a robust EBV-specific $CD4^+$ and $CD8^+$ T-cell response. Because EBV is a human pathogen, the process described takes advantage of both human peripheral blood mononuclear cells (PBMCs) and immunodeficient mice (NOD-scid $IL2r\gamma^{inull}$ mice, NSG) reconstituted with human immune system components (humanized BLT model, bone marrow/liver/thymus) as models to test EBNA1-specific $CD4^+$ and $CD8^+$ T-cell responses.

Figure 2:
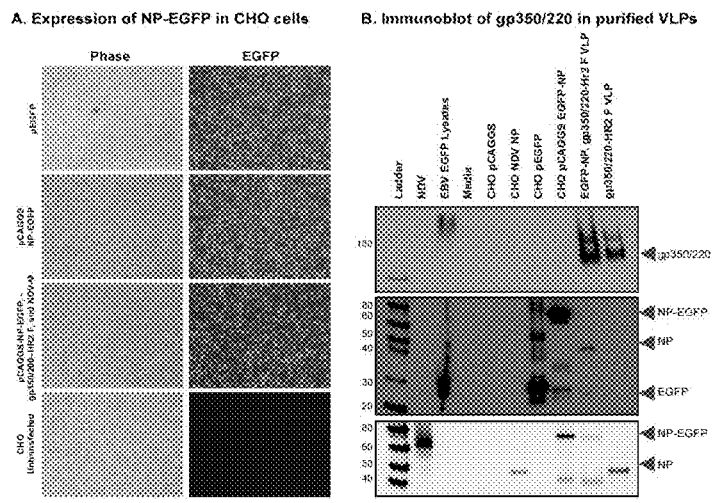
FIG. 2. Assembly and characterization of EBV gp350/220 VLPs incorporated with NDV-NP-EGFP. (A) Expression of EGFP in CHO cells transfected with pCAGGS-NDV-NP-EGFP detected by microscopy. (B) Immunoblot detection of gp350/220 in VLPs purified from supernatant of transfected CHO cells mAb-72A1 (anti gp350/220). Lysates were separated in 4-12% gel. Purified EBV from B95-8 cells was used as positive control.
Figure 3:
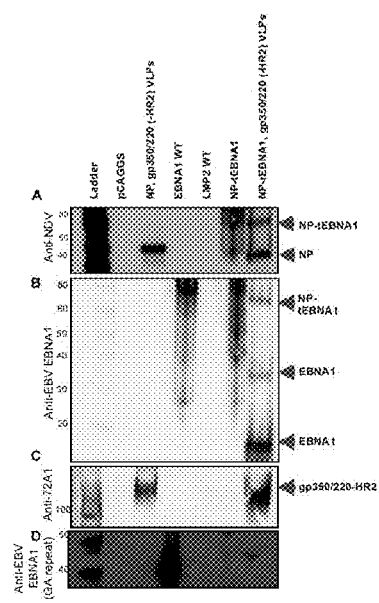
FIG. 3. Immunoblot analysis of EBV-EBNA1, NDV-NP and gp350/220 incorporated into VLPs. (A) Detection of NDV NP-EBNA1 from purified VLPs from supernatant of CHO transfected cells using polyclonal anti-NDV Ab. (B) Detection of EBNA1 in gp350/220 VLPs using specific Ab to EBNA1 DNA binding domain. (C) Detection of gp350/220 incorporated into VLPs (D) anti-EBNA1 Gly-Arg rich repeat domain. 4-12% gel was used.
Figure 4:
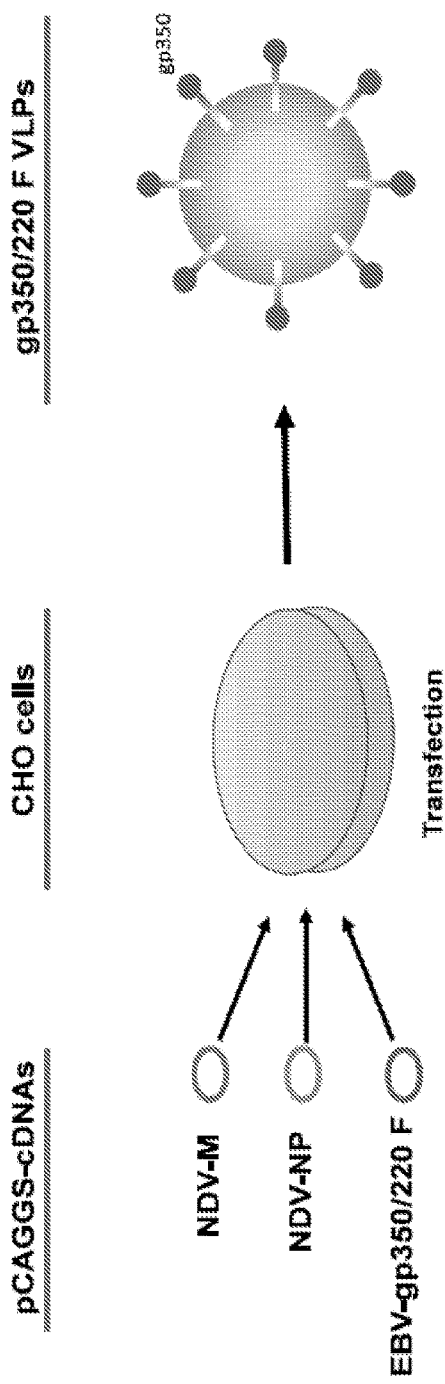
Figure 5:
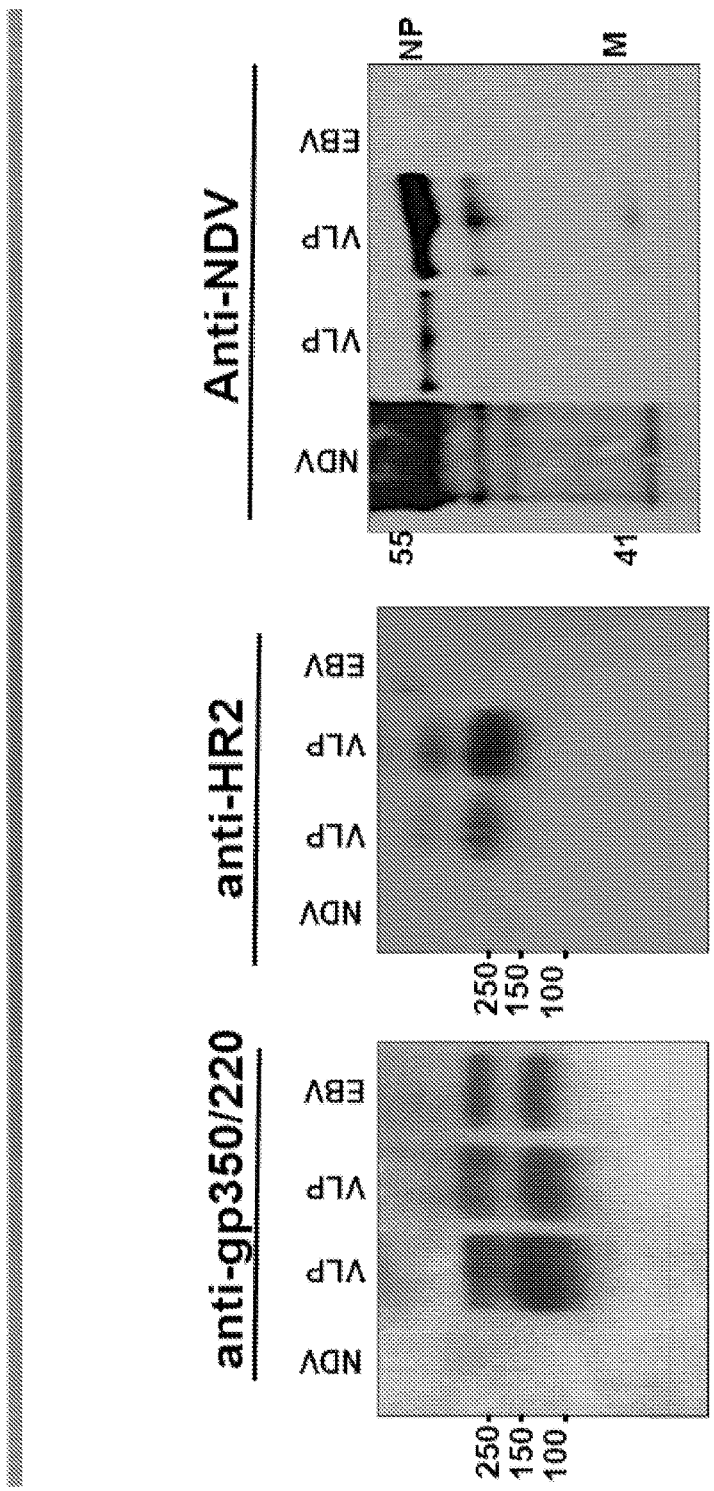
Figure 6:
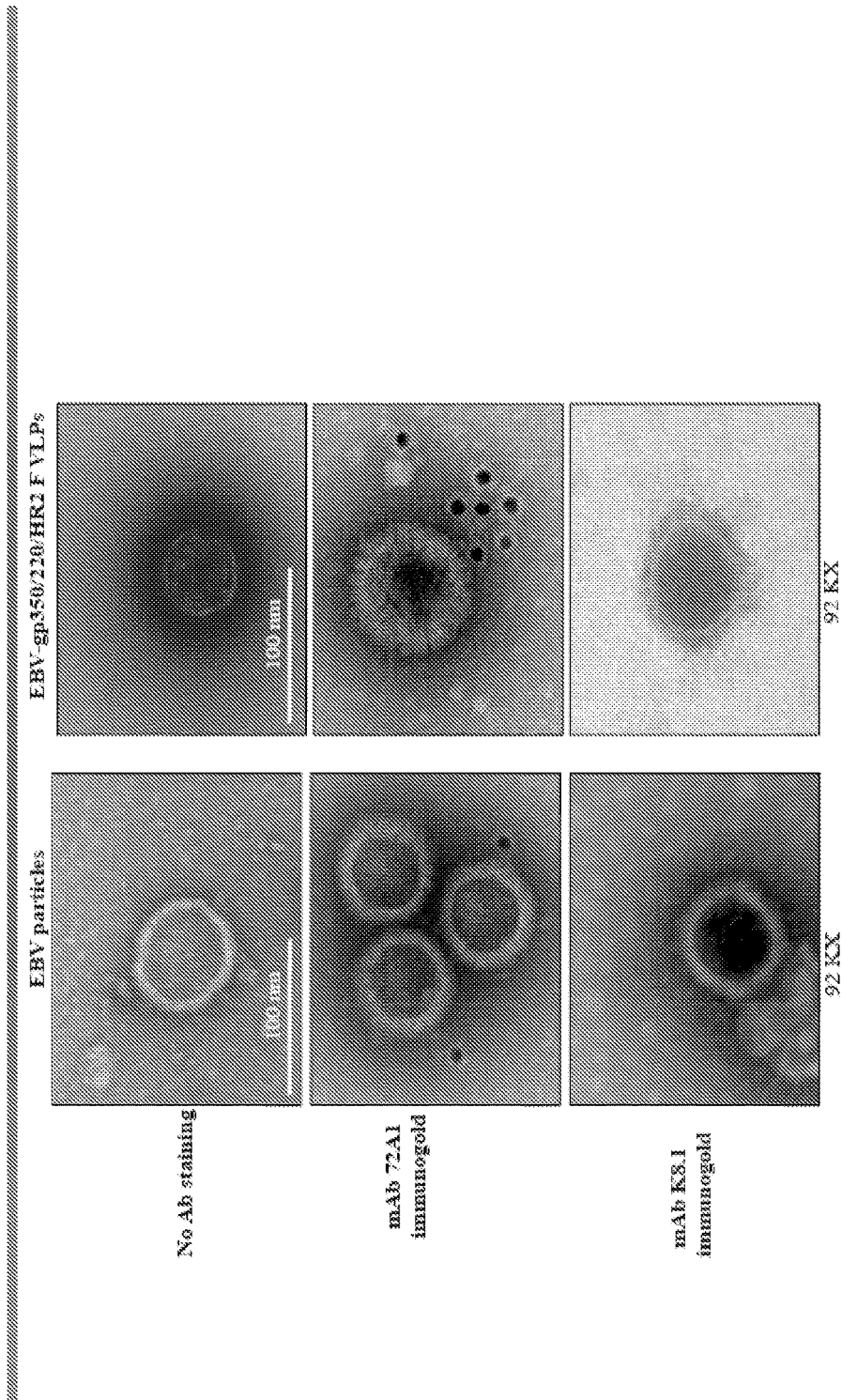
Figure 49:
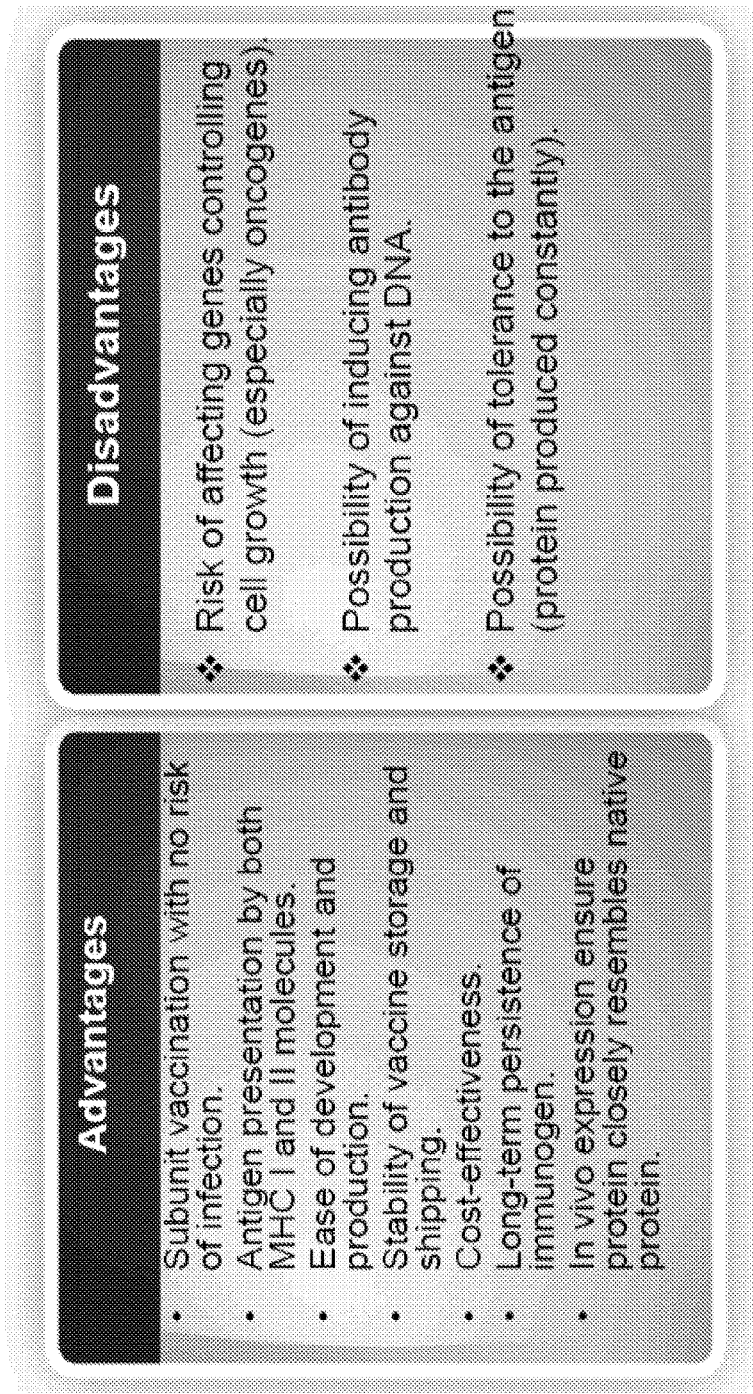
FIG. 49. Challenges of DNA based vaccines.

Current approaches to EBV vaccine development are limited due in part to the oncogenic potential of the EBV genome (FIG. 49). To generate a potent EBV vaccine candidate we included multiple vaccine antigens including tumor-associated antigens in our VLPs (exemplified in FIGS. 1-3).

Despite strong evidence that antibodies (Abs) to gH/gL can neutralize EBV infection, these proteins have not been used to generate an EBV vaccine. In one embodiment, the invention's VLP vaccines contain two tumor-associated antigens (EBNA1 and LMP2); EBNA1 is consistently expressed in B cells of all BL patients and recognized by CD4+ T cells and LMP2 is primarily targeted by CD8+ T cells.

Data herein demonstrate that VLPs containing a functionally inactive truncated EBNA1 (tEBNA1, lacking the Gly-Ala rich domain known to impair presentation of cis-linked sequences), LMP2, and gH/gL, stimulate robust humoral and cellular responses against EBV. Thus, in one embodiment, the invention provides NDV VLPs containing tEBNA1, LMP2, gB and gH/gL for use as a vaccine to induce neutralizing antibodies (nAbs) and/or EBV specific $CD4^+$ and $CD8^+$ T cells responses. In a particular, embodiment, the invention provides EBV gH/gL: tEBNA1-LMP2 VLPs that can be used alone or together with EBV gp350/220 VLPs to prevent EBV infection and its associated diseases. In another embodiment, the invention's vaccines are therapeutic and/or prophylactic vaccines against infectious diseases and cancers, such as cervical cancer.

In one embodiment, the invention provides a recombinant virus-like particle (VLP) comprising, in operable combination, a) Newcastle disease virus (NDV) matrix (M) protein, and b) two or more Epstein-Barr Virus (EBV) antigens, wherein at least one of the two or more antigens is selected from the group consisting of gB, GH, and gL. In one embodiment, the two or more EBV antigens comprise a tumor-associated EBV antigen, wherein the tumor-associated EBV antigen is exemplified by, but not limited to, EBNA1 and LMP2. In a particular embodiment, EBNA1 is truncated (tEBNA1, i.e., EBNA1 that lacks the Gly-Ala rich domain). In a further embodiment the VLP comprises EBV gp350/220. In a particular embodiment, the VLP further comprises, in operable combination, one or more NDV proteins, exemplified by, but not limited to NDV nucleocapsid (NP) protein. NDV heptad repeat domain 2 (HR2) protein, NDV fusion (F) protein, and NDV heamagglutinin-neuraminidase (HN) protein.

The invention further provides a VLP that contains, in operable combination, a) Newcastle disease virus (NDV) matrix (M) protein, and b) EBV gp350/220 (Ogembo et al., "5A chimeric EBV gp350/220-based VLP replicates the virion B-cell attachment mechanism and elicits long-lasting neutralizing antibodies in mice," Journal of Translational Medicine (2015) 13:50). In a particular embodiment, the VLP further comprises, in operable combination, one or more NDV proteins, exemplified by, but not limited to NDV nucleocapsid (NP) protein, NDV heptad repeat domain 2 (HR2) protein, NDV fusion (F) protein, and NDV heamagglutinin-neuraminidase (HN) protein.

The invention further provides a vaccine comprising any one or more of the VLPs described herein, and a physiologically acceptable carrier.

Also provided is an expression vector encoding any one or more of the recombinant VLPs described herein.

The invention also provides a method for immunizing a mammalian subject against Epstein-Barr Virus (EBV), comprising administering an immunologically effective amount of one or more of the VLP vaccines described herein to a mammalian subject in need thereof to produce a treated subject, wherein the administering step is under conditions to produce an immune response to one or more EBV antigen. In one embodiment, the method comprises administering (A) a first recombinant VLP comprising, in operable combination, a) Newcastle disease virus (NDV) matrix (M) protein, and b) two or more Epstein-Barr Virus (EBV) antigens, wherein at least one of the two or more antigens is selected from the group consisting of gB, gH, and gL, and (B) a second recombinant VLP that contains, in operable combination, a) Newcastle disease virus (NDV) matrix (M) protein, and b) EBV gp350/220. In one preferred embodiment, administering the vaccine does not produce EBV-associated cancer. In another embodiment, the method further comprises one or more of a) detecting the immune response to the one or more EBV antigen, b) detecting a reduction in one or more symptoms of EBV infection in the treated subject, and c) determining the presence and/or absence of EBV-associated cancer in the treated subject. In one embodiment, the invention's vaccination method is used prophylactically by administering the vaccine before manifestation of one or more symptoms of infection of the subject with the EBV. In a further embodiment, the invention's vaccination method is used therapeutically by administering the vaccine after manifestation of one or more symptoms of infection of the subject with the EBV. In a particular embodiment, the immune response by the treated subject comprises antibody that specifically binds to the one or more EBV antigen. In a particular embodiment, immune response comprises T lymphocytes that specifically bind to the one or more EBV antigen. In a further embodiment, the T lymphocytes are selected from CD4$^+$ lymphocytes and CD8$^+$ lymphocytes.

EXPERIMENTAL

The following examples serve to illustrate certain preferred embodiments and aspects of the present invention and are not to be construed as limiting the scope thereof.

Example 1

Materials and Methods.

The following is a brief description of the exemplary materials and methods used in the subsequent Examples.
Virus and Cell Lines B95-8 strain harboring EBfaV-GFP was obtained from Dr. Richard Longnecker (Northwestern University, Chicago). EGFP-EBV was prepared as described (53). Purified Kaposi's sarcoma herpesvirus (KSHV) and EBV-EGFP from the AGS cell line were generous gifts from Dr. Christine King (SUNY Upstate Medical School) and Dr. Liisa Selin (University of Massachusetts Medical School), respectively.

Human embryonic kidney HEK-293A cell line, a cloned derivate of 293 was purchased from Life Science Technologies. HEK-293T, a 293 derivative expressing SV-40 T antigen, CHO, Vero (African green monkey kidney), ELL-0 (chicken embryo), K562 (human erythroleukemia), Raji (EBV+ Burkitt's lymphoma), HB168 (72A1 murine hybridoma) were all purchased from the American Type Culture Collection. Cell lines 293A, CHO, and ELL-0 were cultured in Dulbecco's Modified Eagle's medium (DMEM), B95-8, K562, HB168 and Raji cell line were grown in RMPI media. All media contained 1% L-glutamine, 10% heat-inactivated fetal bovine serum (FBS) and 2% penicillin-streptomycin unless otherwise specified.
Antibodies Primary monoclonal antibodies (mAb)-72A1 and -2L10 anti-gp350/220 were purchased from EMD Millipore. Polyclonal rabbit and anti-Newcastle disease virus (NDV) and anti-HR2 have been previously described (54). MAb anti-CD35 (clone E11) and anti-CD21 (clone LT21) were purchased from BioLegend. mAb EBNA1 (clone IH4-1) was a gift of Dr. F. Grässer, Institut für Virologie, Germany. Both goat polyclonal anti-EBNA1 Gly-Arg regions and rat monoclonal anti-EBV LMP2A (clone 14B7) were purchased from Abcam. Monoclonal anti-EGFP (clone GSN149) was purchased from Sigma. All the antibodies to EBVgH, EBVgH/gL and EBVgB were gifts of Dr. Lindsey Hutt-Fletcher (Louisiana State University Health Sciences Center, Shreveport, La.). mAb anti EBVgH/gL (clone CL59) recognizes gH alone and binds to an epitope between residues 501-628 which is part of the C-terminal flap structure in domain IV; EID1 recognizes only gH/gL complex and partially blocks binding to an integrin so probably binds somewhere on the domain I/domain II interface. CL40 recognizes gH/gL complex. mAb anti-gB (clone CL55) recognizes the ectodomain of the glycoprotein, while rabbit polyclonal anti-gB (clone BA23) recognizes C-terminal domain.

Secondary: Horseradish peroxidase (HRP)-conjugated goat anti-mouse IgG (total and isotype specific) antibodies, goat anti-rabbit or goat anti-rat antibodies for immunoblot or ELISA were purchased from Sigma. Goat F(ab')2 anti-mouse IgG (H+L) AF488 or AF594 was used for cytometric and confocal analyses (Invitrogen). Goat anti-mouse IgG (H+L) immunogold was used for electron microscopy (EM) (Aurion).
Plasmid Vectors
PCAGGS-EBV gp350/220-F or pCAGGS-EBV gp350/220-HR2 F Full length EBV gp350/220 (BLLF1) from the BamHI L fragment of EBV genome strain B95-8 (55) was amplified by PCR and cloned into pCAGGS as described (56). A chimeric fragment consisting of amino acids 1-864 encoding the gp350/220 ectodomain (ED) fused to the amino acids 466-553 of the NDV-F heptad repeat 2 (HR2), transmembrane (TM) and cytoplasmic (CT) domains was constructed by three-way ligation to obtain EBVgp350/220-F as described (56). Full length chimeric EBVgp350/220-F lacking the heptad region of the NDV TM region was synthesized by Geneweiz, cloned into pCAGGS vector (pCAGGS-EBVgp350/220-HR2 F) and sequence fidelity verified. A full-length gp350/220 wild type (WT) were also synthesized and cloned into pCAGGS vector to be used as a control in various experiments. pCAGGS-F, pCAGGS-M and pCAGGS-NP derived from NDV (Avulavirus) have been described (57).

pCAGGS EBVgH/gL (gp85/gp25)

To construct chimeric EBVgH-F and EBVgL-HN proteins, sequences encoding the TM domain lacking the heptad region and the cytoplasmic tail of the NDV F protein (amino acids 499-553) or hemagglutinin-neuraminidase (HN) protein (amino acids 1-46) were fused to the sequence encoding the ectodomain of gH, amino acids 1-679 and to amino acids 25-137 of gL, respectively. These chimera proteins were synthesized and cloned individually into the pCAGGS vector. cDNAs of full length gH WT (amino acids 1-707) and gL WT (amino acids 1-137) were also synthesized and individually cloned into pCAGGS vector as controls.

pCAGGS-EBV gB-F (gp110)

A chimeric fragment consisting of amino acids 1-736 encoding the EBV gB ectodomain fused to the NDV-F tacking HR2 region of the TM and CT domains (amino acids 466-553) was synthesized. The synthesized sequence was cloned into pCAGGS vector and sequence fidelity verified. A full-length EBVgB WT (amino acids 1-790) was also synthesized and cloned into pCAGGS vector as a length EBVgB WT (amino acids 1-790) was also synthesized and cloned into pCAGGS vector as a control.

Generation of Fusion Protein Between NP and EGFP, Truncated EBNA1 or LMP2.

Fusion proteins between NP (amino acids 1-489) and EGFP (amino acids 1-241), truncated EBNA1 encoding deletion of Gly-Ala regions from the EBNA1 sequence known to impair presentation of cis-linked sequences (amino acids 326-641), or full length LMP2 (amino acids 1-497) were synthesized by Geneweiz and fidelity of the sequences verified. The specific fusion sequences were individually cloned into pCAGGS vector. Full length EGFP, EBNA1 and LMP2 were also synthesized and cloned into pCAGGS vector as controls.

Transfection, Generation and Purification of EBV gp350/220-F, EBV gp350/220-EGFP, gp350/220-EBNA1, EBVgH/gL, EBVgH/gL-EBNA1 and EBVgB-LMP2 VLPs.

To determine surface expression of the EBV glycoproteins, 1.0 µg/well of pCAGGS, pCAGGS-gp350/220 WT, pCAGGS-EBVgp350/220-F, pCAGGS-EBV gp350/220-HR2 F, pCAGGS-EBVgH WT, pCAGGS-EBVgH-F, pCAGGS-EBVgL WT, pCAGGS-EBVgL-HN or pCAGGS-EGFP were individually transfected into 80% subconfluent CHO cells seeded in six-well tissue culture plates using Lipofectamine and Reagent Plus (Life Sciences Technologies) according to the manufacturer's direction. Both gH-F/gL-HN or gH WT/gL WT plasmids were also transfected into CHO cells to assess the formation of the gH/gL complex. Cells were harvested at 48 h post-transfection to assess surface expression of individual protein by cytometry after staining with specific primary antibody followed by secondary antibody. In certain cases, surface expression of individual proteins were also assessed transfected 293A, Vero or ELL-0 cell lines. Cytometric analysis was performed on a LSRII benchtop FC (Becton-Dickinson, B-D) and data analyzed using CellQuest Pro Version 4.0.1 (B-D) and/or FlowJo Cytometry Analysis software (Tree Star Inc) as described (56).

For VLP preparation, equal amounts (8 µg/plasmid) of pCAGGS-NDV M, NP and pCAGGS-EBV gp350/220-F plasmids were co-transfected into cells seeded in T-175 cm$^2$ flasks. DNA-Lipofectamine complexes were incubated at 37° C. for 5 h with 293T and ELL-0 or overnight with CHO cells. Complexes were removed by washing and 20 ml of complete media with or without 4 mM of sodium butyrate (Millipore ED) and 20 ng/ml of TPA (12-O-tetradecanonylphorbol 13-acetate) (Sigma) were added. VLPs were isolated by sucrose gradient purification as described (58). Similar strategy was used to generate EBV gp350/220-HR2 F, EBV gp350/220-HR2 F-EGFP, EBV gp350/220-HR2 F-EBNA1, EBV gH/gL-EBNA1 and EBVgB-LMP2 VLPs in CHO cells.

Silver Stain, Immunoblot Analysis, Electron Microscopy and Immunogold Staining

Purified EBV, VLPs or cells were lysed in RIPA buffer (Boston Bioproducts) containing complete protease inhibitor cocktail (Roche Applied Science). Cell lysates were incubated on ice for 15 min, and then centrifuged for 5 min at 14,000×rpm in microcentrifuge. The protein content of lysates was determined by Bradford assay using Coomasie Brilliant Blue (Sigma). Lysates were boiled for 5 min in Laemmli SDS-sample buffer (Boston Bioproducts) under non-reducing or reducing conditions. A known quantity of protein lysate was loaded onto a 4-12% polyacrylamide gel for protein separation. Protein was detected by Pierce's silver stain kit following manufacturer's recommendation. For immunoblot analyses, separated proteins were transferred to a PVDF membrane (Life Sciences Tech.) using iblot (Life Sciences Tech.). Membranes were pre-incubated with 5% non-fat dry milk (LabScientific) for 30 min and detected with specific antibodies as previously outlined (26, 59).

Purified VLPs and viruses were analyzed by EM as described (50). Briefly, particles were dialyzed against 2 L of 1×TNE (100 mM Tris; 2.0M NaCl; 20 mM EDTA; pH 7.4) to remove residual sucrose. Purified KSHV, EBV and VLP gp350/220/HR2 F were incubated with 3% BSA in TNE for 45 min and embedded on the grid. Primary antibody (10 µg/ml) was diluted in 1% BSA/TNE and adsorbed to the grid for 1 hour at room temperature. Following three washes with 1×TNE, secondary gold-conjugated antibody was added for 1 hour at room temperature (RT). The grids were washed twice with TNE, and negatively stained with 12% phosphotungstic acid (pH7) for 14 sec; air dried for 30 min and examined using a Tecnai transmission electron microscope.

Confocal Microscopy, Cell Binding Assays

Cells were washed three times with 1× phosphate buffer saline (PBS) and confocal microscopy performed as previously outlined (26). Briefly, 1×10$^6$ cells were seeded onto Labtek slides and incubated at RT for 1 hour with standard amounts of VLP predetermined based on silver stain and/or Bradford assay quantification of total protein. Mixture of cells and VLPs were stained with mAb Alexa-fluor (AF) 594 anti-CD21 and mAb AF488 anti-CD35 for 30 min on ice. Nuclei were stained with DAPI 33342 (Sigma) for 5 min at RT. Stained cells were washed three times, mounted (Mounting Medium, DakoCytomation) and imaged using an UPlanApo 60×1.42 NA objective on an Olympus BX62 microscope fitted with a cooled Hamamatsu Orca AG CCD camera. The microscope, filters, and camera were controlled as outlined (61). The deconvolution process is described (26).

Immunization, Enzyme-Linked Immunosorbent Assay (ELISA) for Antibodies and IFN-γ

Sera from terminal bleed of mice immunized with EBV gB-LMP2 VLP, EBV gH/gL VLP, EBV gp350/220-HR2 F VLP, EBV gp350/220-HR2 F VLP, or UV-inactivated EBV were used to determine IgG titers measured by ELISA (62). Soluble gp350/220 ED or lysates from ELL-0 cells transfected with gB or gH/gL were used as target antigens. Briefly 96-well microtiter plates (Nunc-Immuno Plate Maxisorp) were coated with 50 ng/well of recombinant gp350/220 ED, gB or gH/gL in a carbonate buffer (pH 6.2) at 4° C. overnight and blocked with 1% BSA. Serially diluted sera in PBS was added for 2 h at RT and washed. Antibody binding was detected with HRP-labeled goat anti-mouse IgG, secondary antibodies at RT for 1 h. Plates were washed 5× and the substrate tetramethylbenzidine (Life Science Technologies) was added. Reactions were stopped with 2M sulfuric acid. To determine antibody titer, optical density was read at 450 nm with an ELISA reader (Spectramax® Plus 384, Molecular Devices). The highest antibody dilution yielding an $OD_{450}$ 2× higher than that of TNE-treated mice was designated the endpoint titer. Anti-gp350/220 mAbs served as positive control for gp350/220.

Peptides corresponding to the immunization components, as well as control peptides were used to stimulate $5\times10^5$ splenocyte in. Synthetic peptides derived from EBNA1 $_{(HPVGEADYFEY)}$, LMP2$_{(CLGGLLTMV)}$ or Promix EBV peptide pool consisting of 26 peptides, each corresponding to a defined HLA class I-restricted T cell epitope from EBV were used at concentration of 1 μg/mL in the assay. After overnight culturing, the supernatants were tested for IFN-γ release by ELISA. SINFEKL ovalbumin was used as a negative control and concavalin A and IL1B were used as model antigens.

Serum EBV-Neutralization Studies and Statistical Analysis

Terminal bleed sera from mice serially immunized with UV-EBV, soluble gp350/220 ED, TNE, EBV gp350/220-F and EBV gp350/220-HR2 VLPs were heat-inactivated at 56° C. to remove complement. Sera were pre-incubated 1:1 with purified EGFP-EBV at different concentrations (typically a 1:5 virus dilution from a frozen stock) for 1 h at RT before infection $10^5$ Raji or 293 cell lines seeded in 24-well tissue culture plates as previously outlined (53, 56, 63). Anti-gp350/220 mAb-72A1 (neutralizing), mAb-2L10 (non-neutralizing) and sera from TNE-treated mice (vehicle) served as controls. Experiments were repeated at least 3 times. Plates were incubated at 37° C. for 3 days and visualized daily to enumerate GFP⁺ cells. Cytometry was performed on day 3 for end-point analysis. Neutralization data were analyzed using Graph Pad Prism 6 Software (GraphPad Software, Inc., San Diego) as describer (56).

Example 2

Construction and Purification of Epstein-Barr Virus-Like Particle (EBV-VLP) Gp350/220 Using Newcastle Disease Virus Platform as a Prophylactic Vaccine Candidate Against EBV Infection.
See FIGS. 4-11.

Example 3

Development of Novel gH/gL VLPs.
See FIGS. 12-16.

Example 4

Development of a Novel gH/gL-EBNA1-LMP2 VLPs.
See FIGS. 17-29.

Example 5

NDV NP as a Carrier for EBNA1-LMP2 in EBVgp350/220 or gH/gL VLPs.
See FIGS. 30-34.

Example 6

Figure 36:
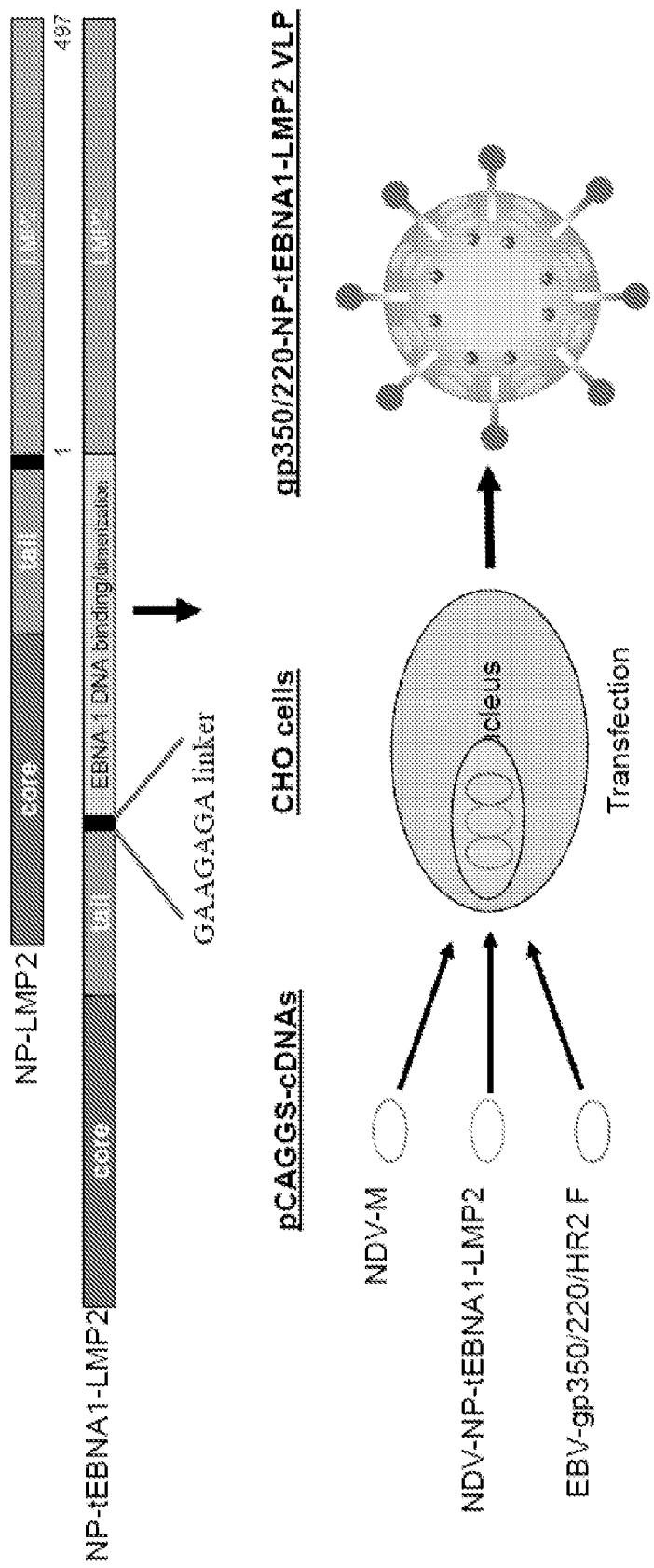
Figure 38:
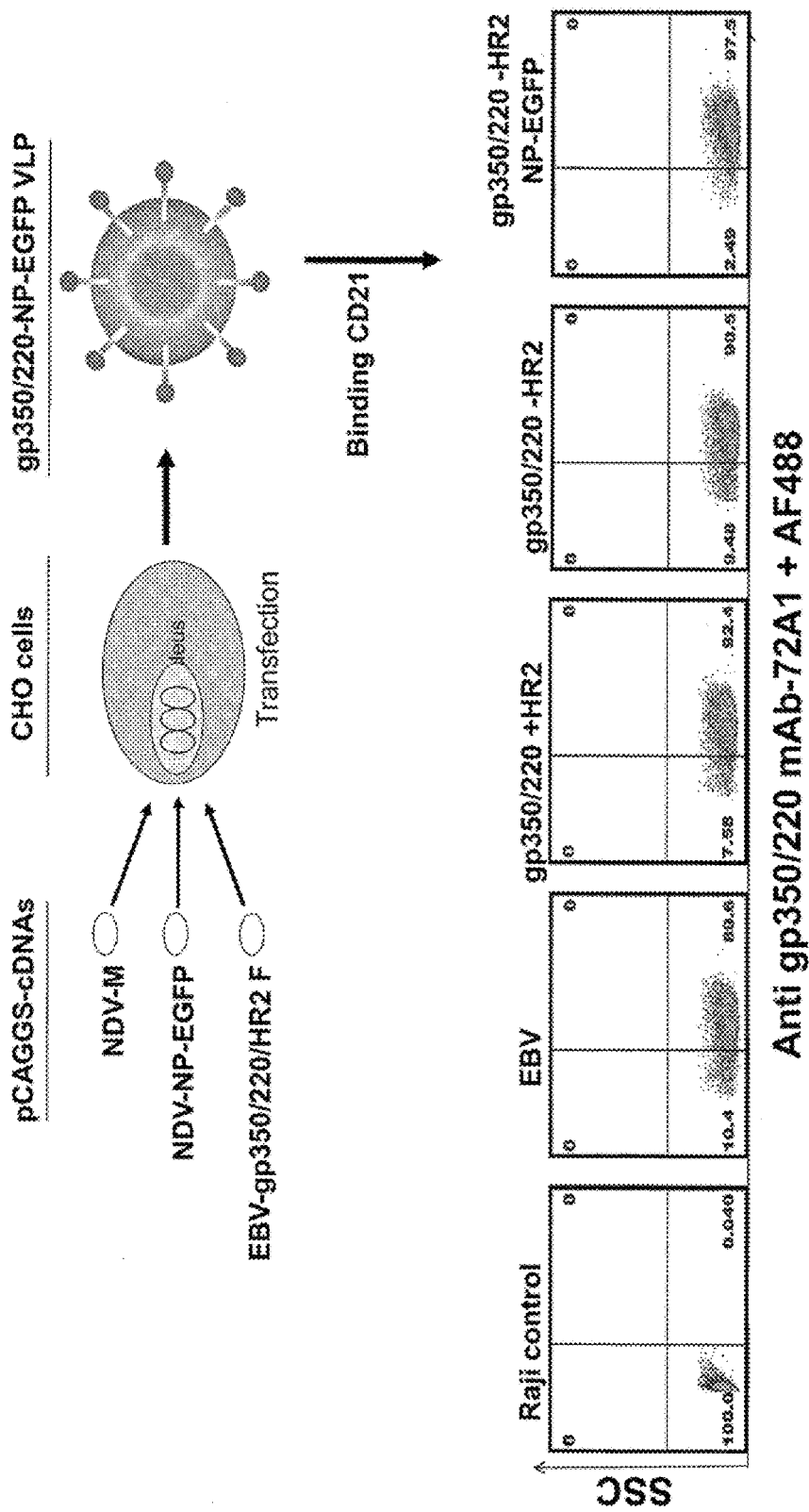
Figure 39:
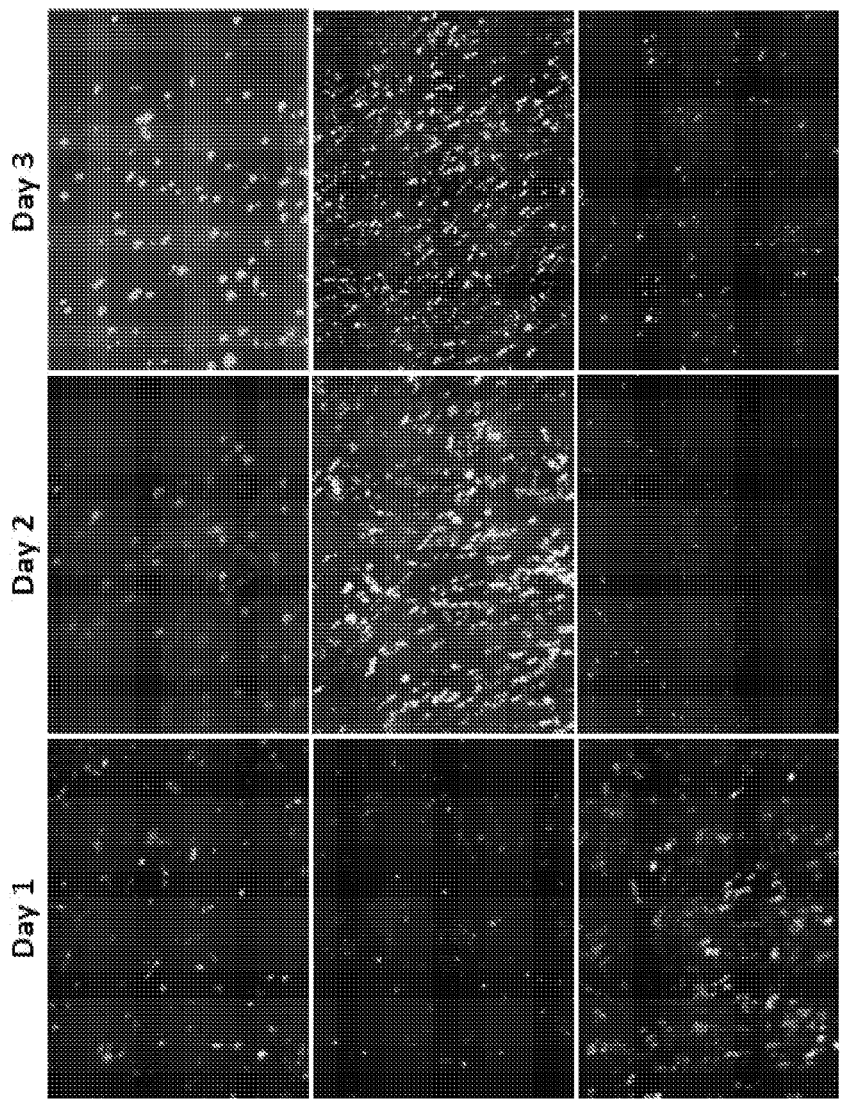
Figure 40:
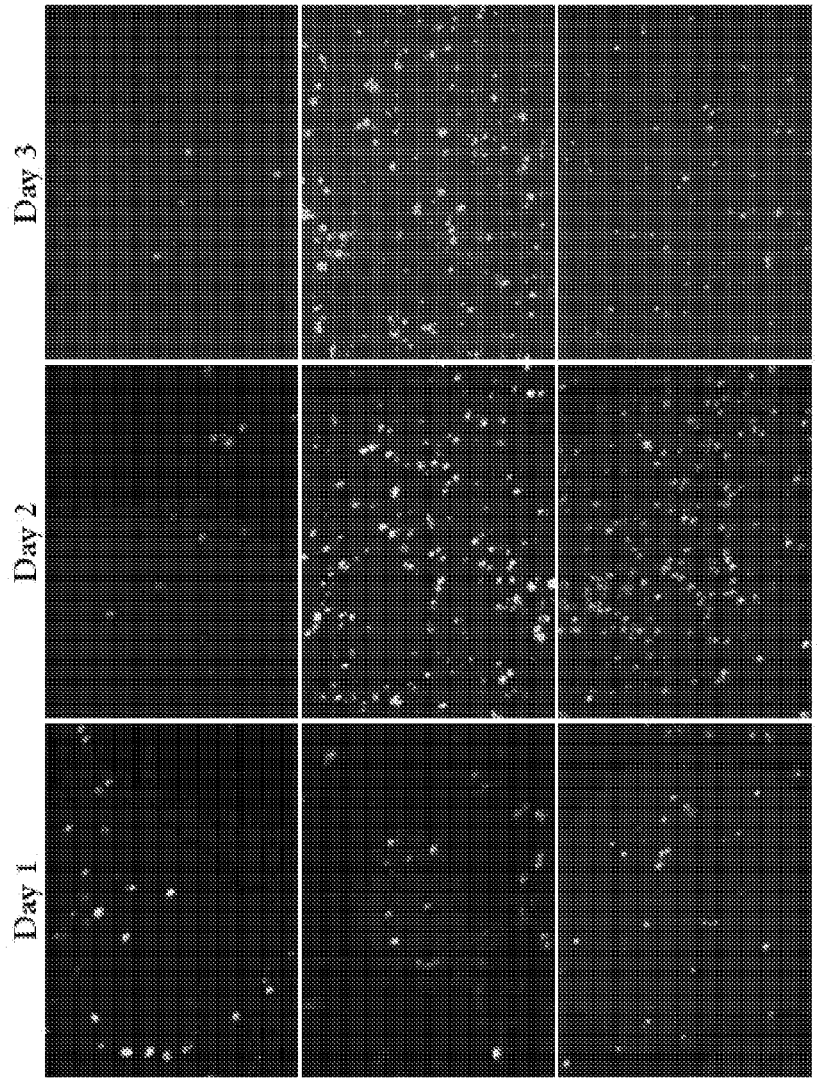
Figure 41:
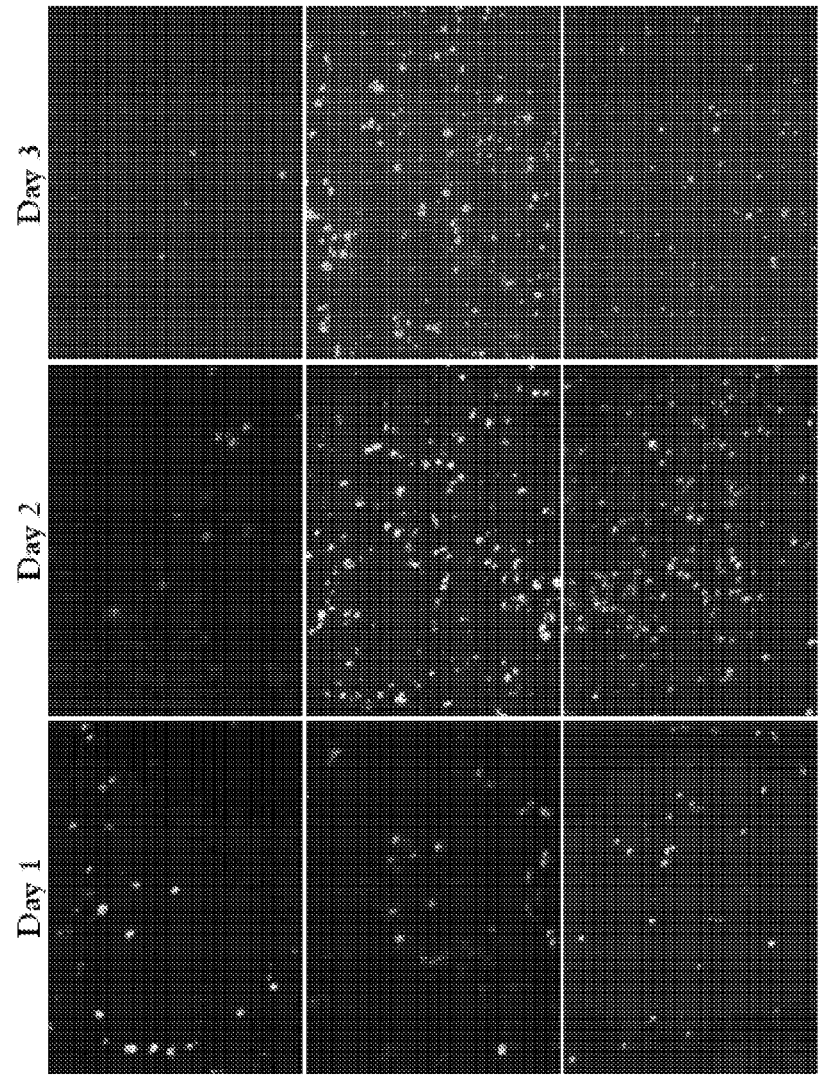
Figure 42:
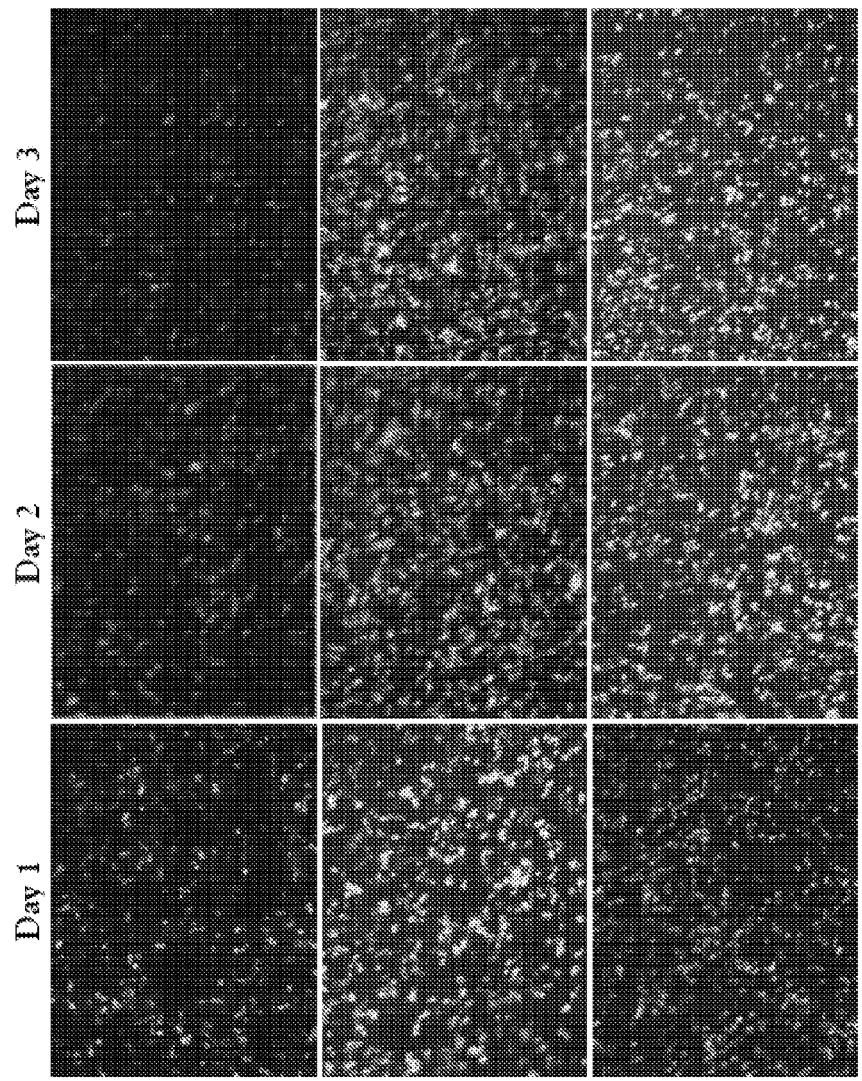
Figure 43:
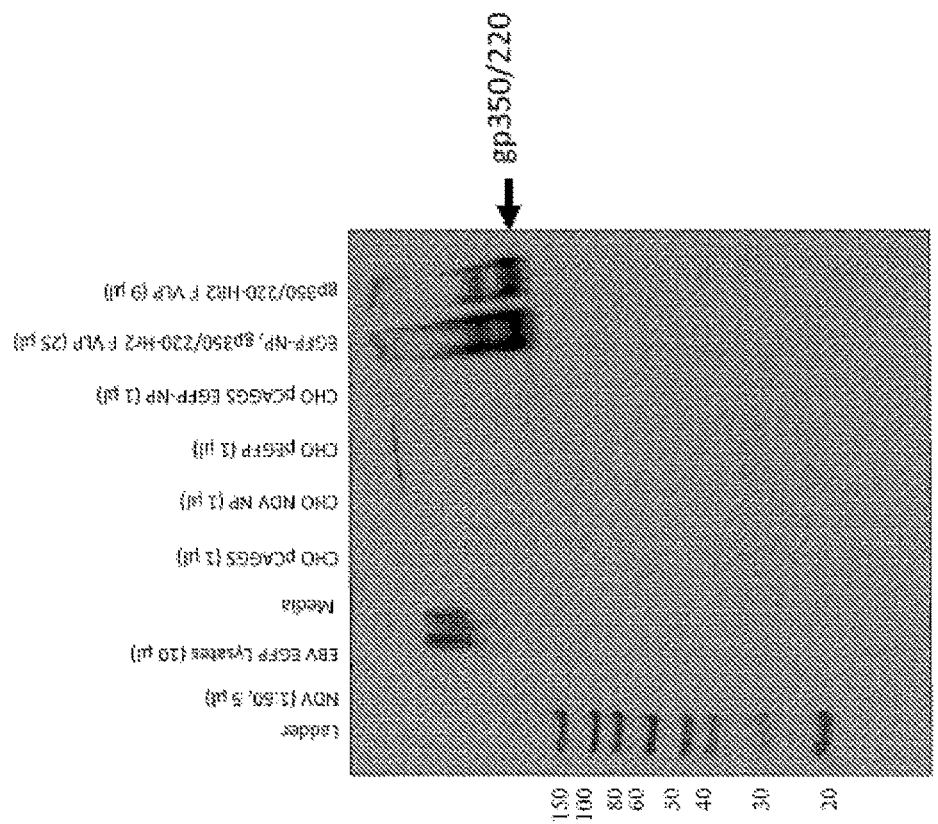
Figure 44:
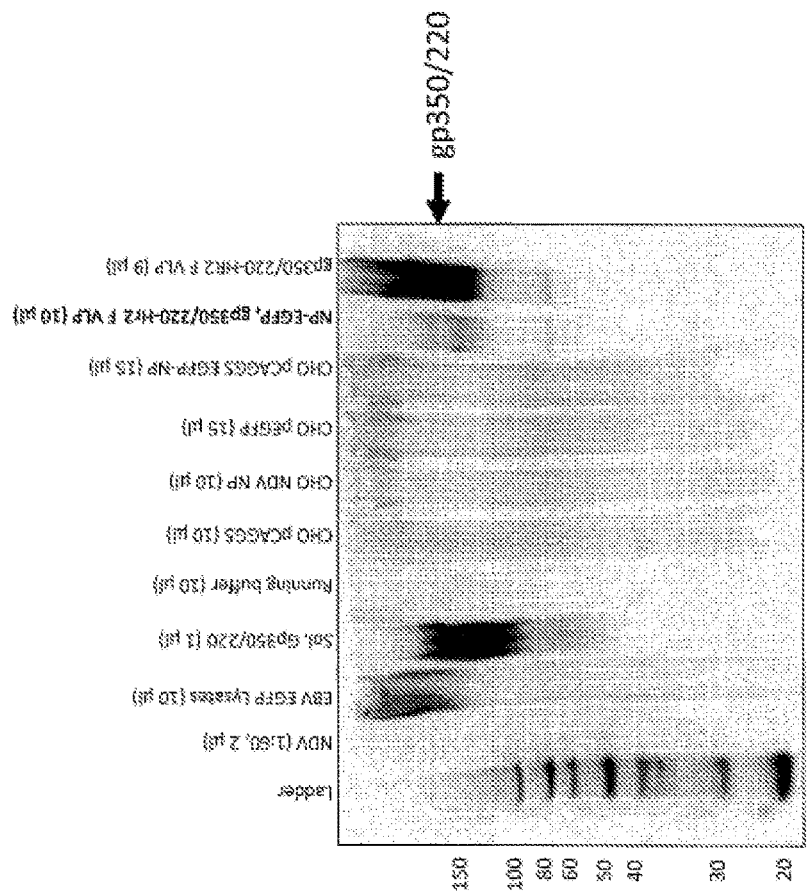
Figure 45:
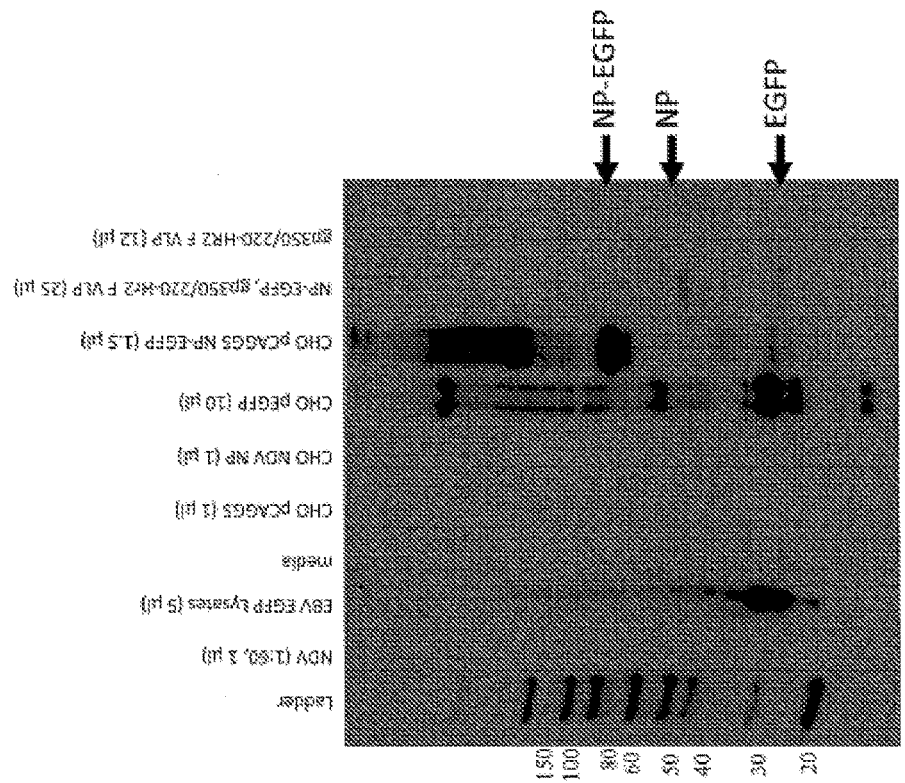
Figure 46:
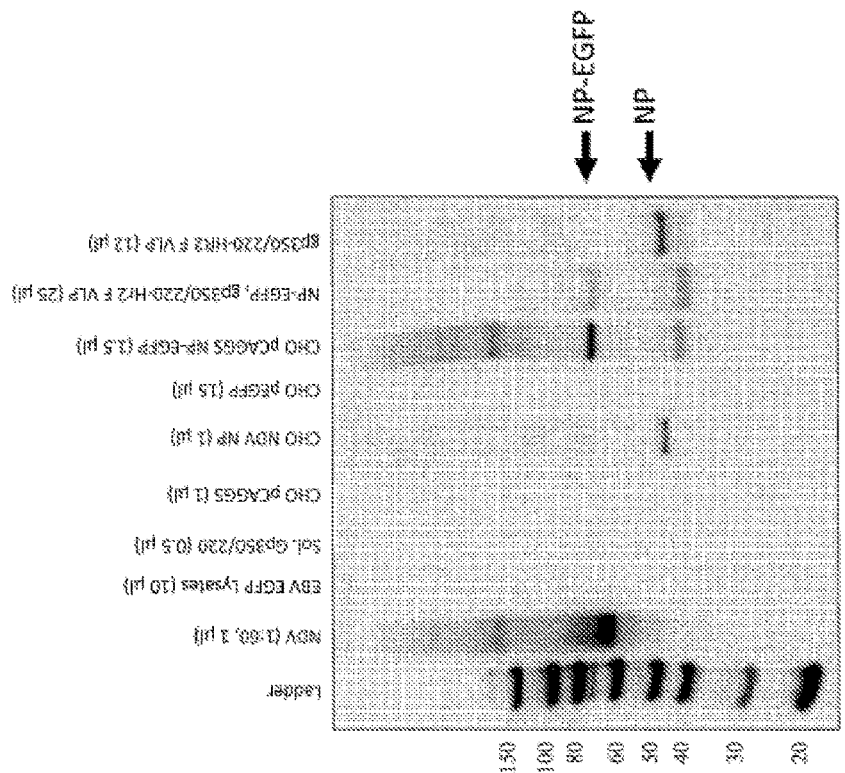
Figure 47:
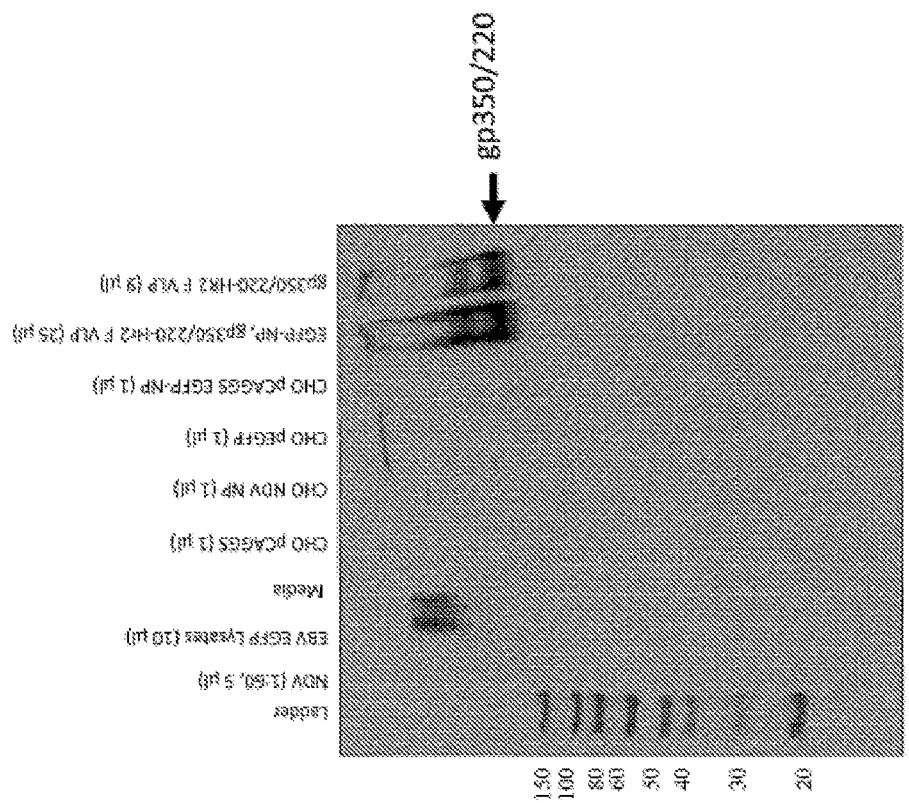

Generating NP-tEBNA1-LMP2 Chimera Protein.
See FIGS. 35-37.

Example 7

NP-EGFP Blots.
See FIGS. 38-47.

Example 8

Generating VLPS containing NP-tEBNA1 Chimera Protein and containing NP-tEBNA1-LMP2 Chimera Protein.
See FIGS. 50-53 and 62-71.

Example 9

Figure 72:
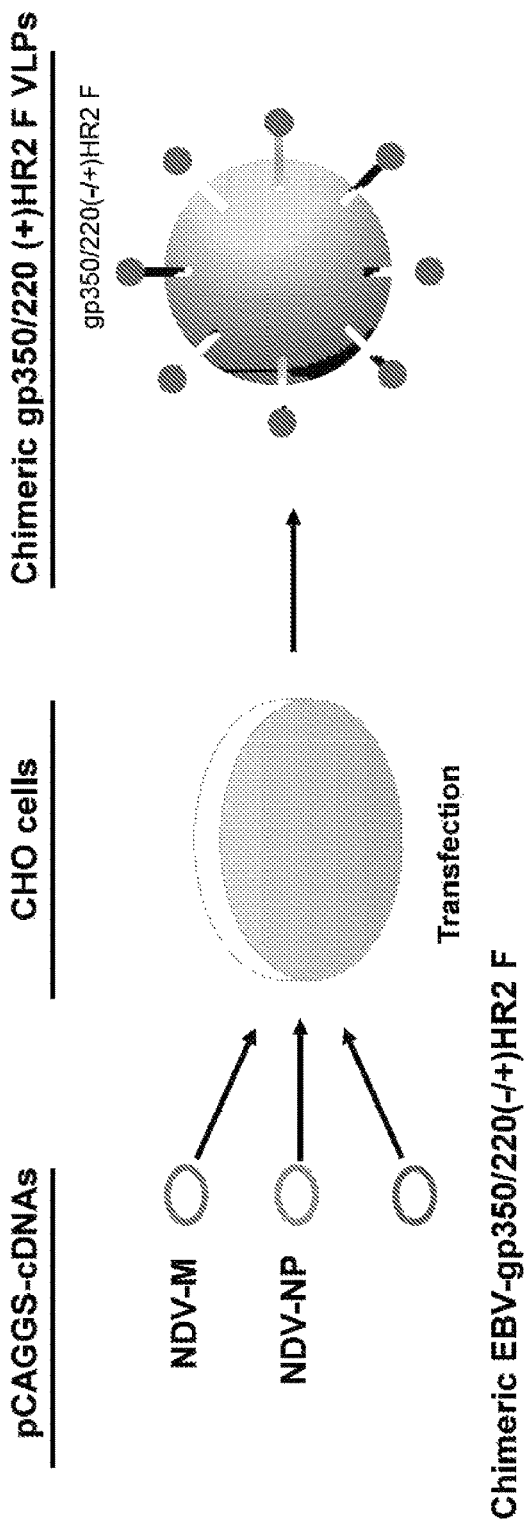
FIG. 72. A diagram showing the transfection process used in the production of chimeric EBV gp350/220(−/+)HR2 F VLPs. Ogembo et al., J. Trans. Med. 2015; 13:50, Pantua et al., J. Virol. 2006; 11062-73.

Detection of Chimeric EBV-Gp350/220-F, EBV gH-F/gL-HN and EBV gB-F on the Surface of Mammalian and Avian Cell Lines In this study, we generated novel VLPs known for their safety, adjuvanicity and efficacy; to present select EBV glycoproteins (gp350/220, gH/gL or gB) and/or latent genes expressed in EBV positive tumors (EBNA1 and/or LMP2) to elicit neutralizing antibodies and T-cell responses, respectively. These VLPs are devoid of EBV genomic DNA and are efficiently produced in CHO cell line; an FDA approved vehicle. Newcastle disease VLP-based platform has been shown to efficiently assemble from three or four virion proteins, the envelope glycoproteins, F (fusion, a type 1 glycoprotein) and/or HN (hemaglutinin-neuraminidase, a type 2 glycoprotein), together with core proteins M (matrix) and NP (nucleocapsid protein) that drive assembly and release as described (58, 64); patent issued to Morrison et al., U.S. Pat. No. 7,951,384 issued to Morrison et al. on May 1, 2011; U.S. Pat. No. 8,974,797, issued to Morrison on Mar. 10, 2015, each of which is incorporated by reference and see also FIG. 72. Further novel methods for producing NDV-based VLPs are disclosed herein.

Figure 73:
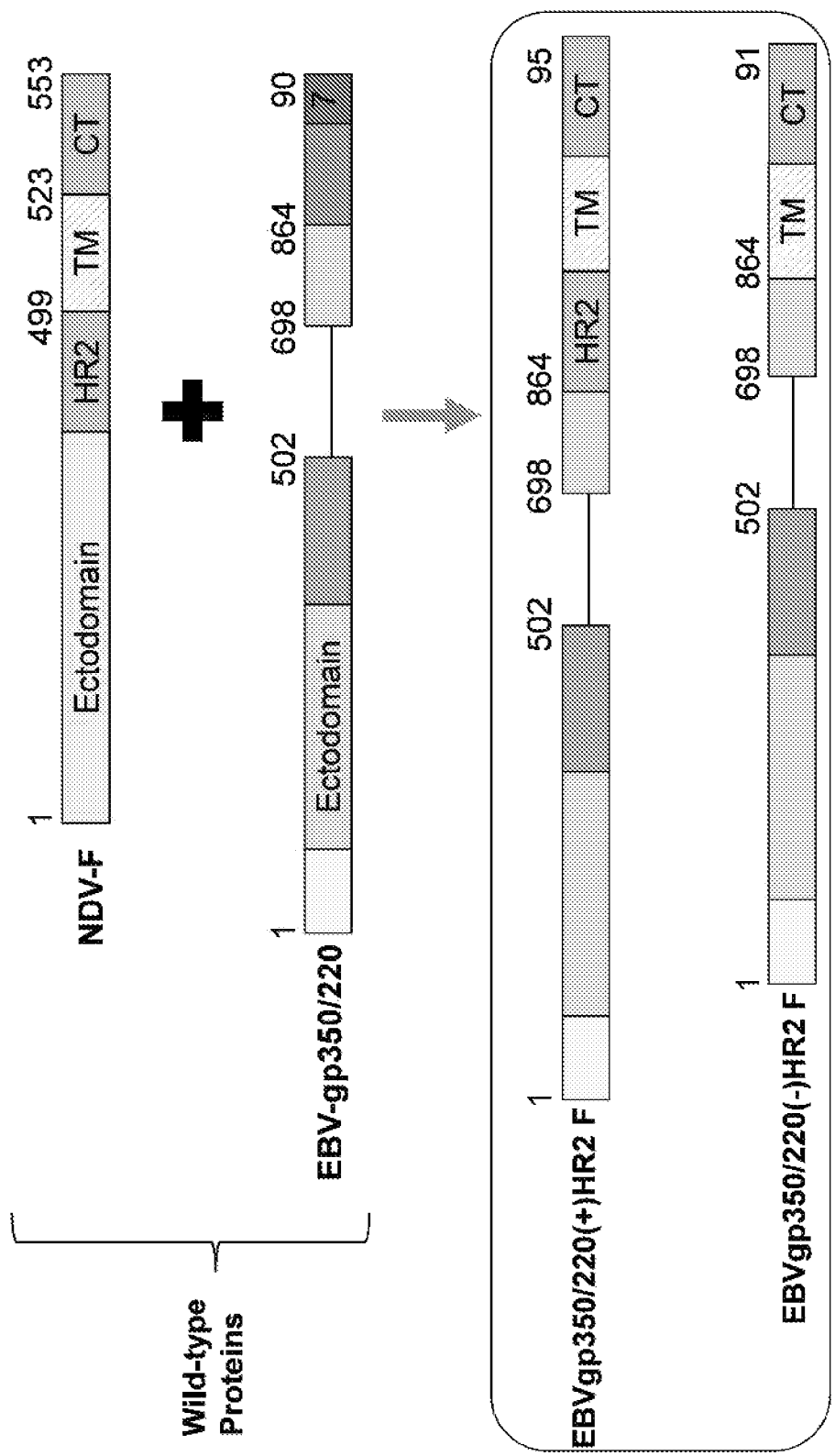
FIG. 73. Schematic of EBV gp350/220 F chimeric protein. A diagram of full length wild type NDV-F (top), full length EBV gp350/220-WT (center), and chimeric EBV gp350/220(−/+)HR2 F construct (bottom) (not to scale). C-terminal amino acid sequences comprising the gp350/220 ectodomain (ED) and N-terminal sequences from NDV-F HR2 at the point of fusion are indicated. The single line represents amino acid sequences deleted in frame in the gp220 isoform. Both isoforms contain the N-terminal B-cell attachment epitope. Ogembo et al., J. Trans. Med. 2015; 13:50.
Figure 74:
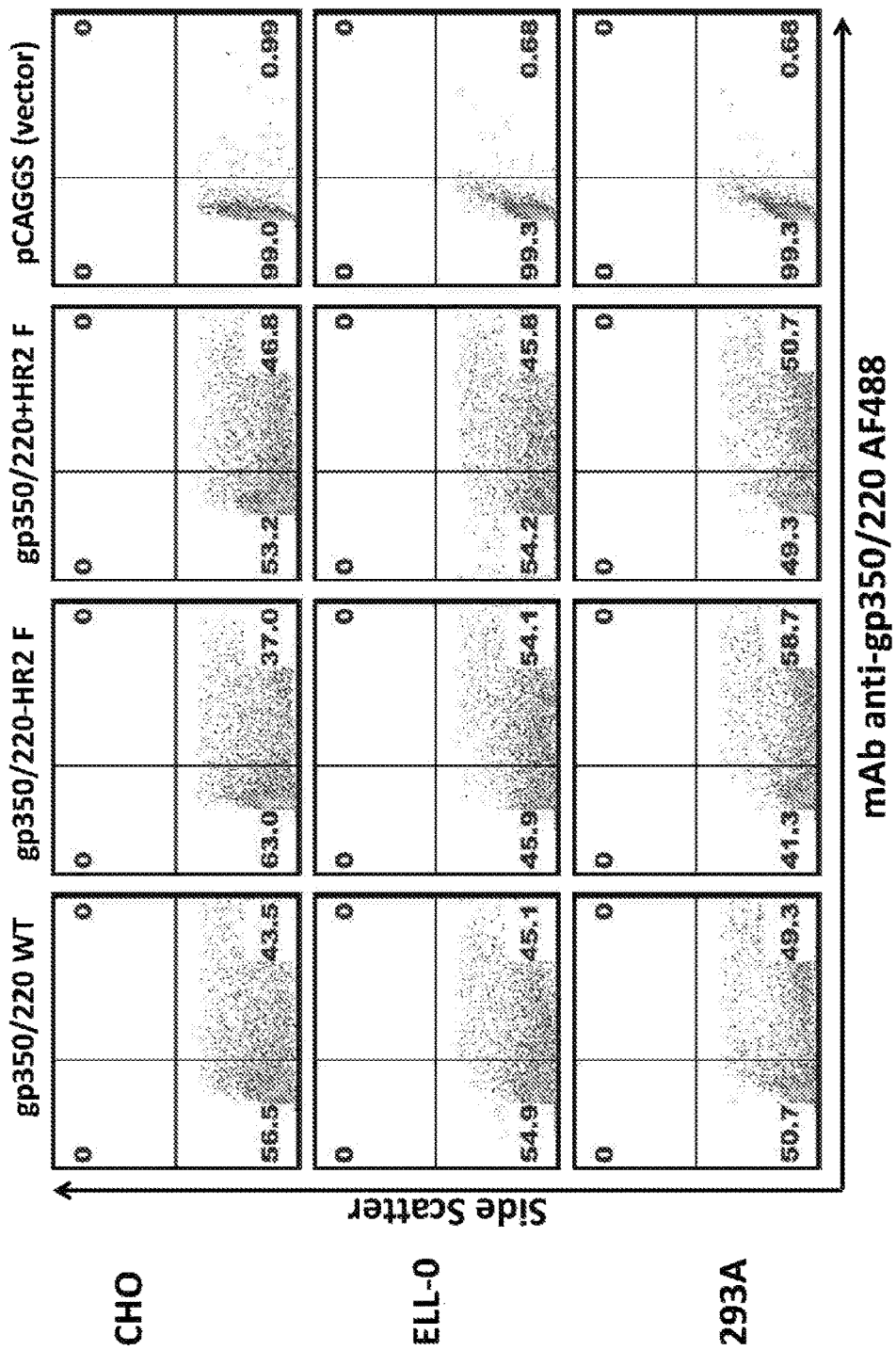
FIG. 74. Expression of EBV gp350/220-WT and EBV gp350/220-F was measured in three transfected cell lines (CHO, ELL-0, and 293A) compared to the vector control. One million cells from each cell line was transfected with 1 μg of either pCAGGS-EBV gp350/220 WT, pCAGGS-EBV gp350/220-HR2 F, pCAGGS-EBV gp350/220+HR2 F or pCAGGS alone (vector control). At 72 h post-transfection, cells were stained with anti-gp350/220 mAb-72A1 followed by AF488-coupled goat anti-mouse IgG (H+L) and analyzed by flow cytometry.

To generate EBV gp350/220 bearing VLPs; we first constructed an EBV gp350/220 F, EBV gp350/220-HR2 F, chimeric plasmids (FIG. 73). To assess whether the expressed chimera proteins appropriately localized to the plasma membrane, pCAGGS-EBV gp350/220-F, pCAGGS-EBV gp350/220-HR2 F and pCAGGS-EBV gp350/220 WT plasmids were individually transfected into CHO, ELL-0 and 293A cell lines from three different species. Membrane expression of the gp350/220 was analyzed by cytometry. MAb-72A1 directed to the N-terminal attachment protein binding epitope of gp350/220 (65) detected expression of both gp350/220 WT and chimeric EBV gp350/220 F proteins at the surface of all relevant transfectants (FIG. 74).

Example 10

Assembly and Characterization of Chimeric EBV gp350/220 F VLPs

Figure 75:
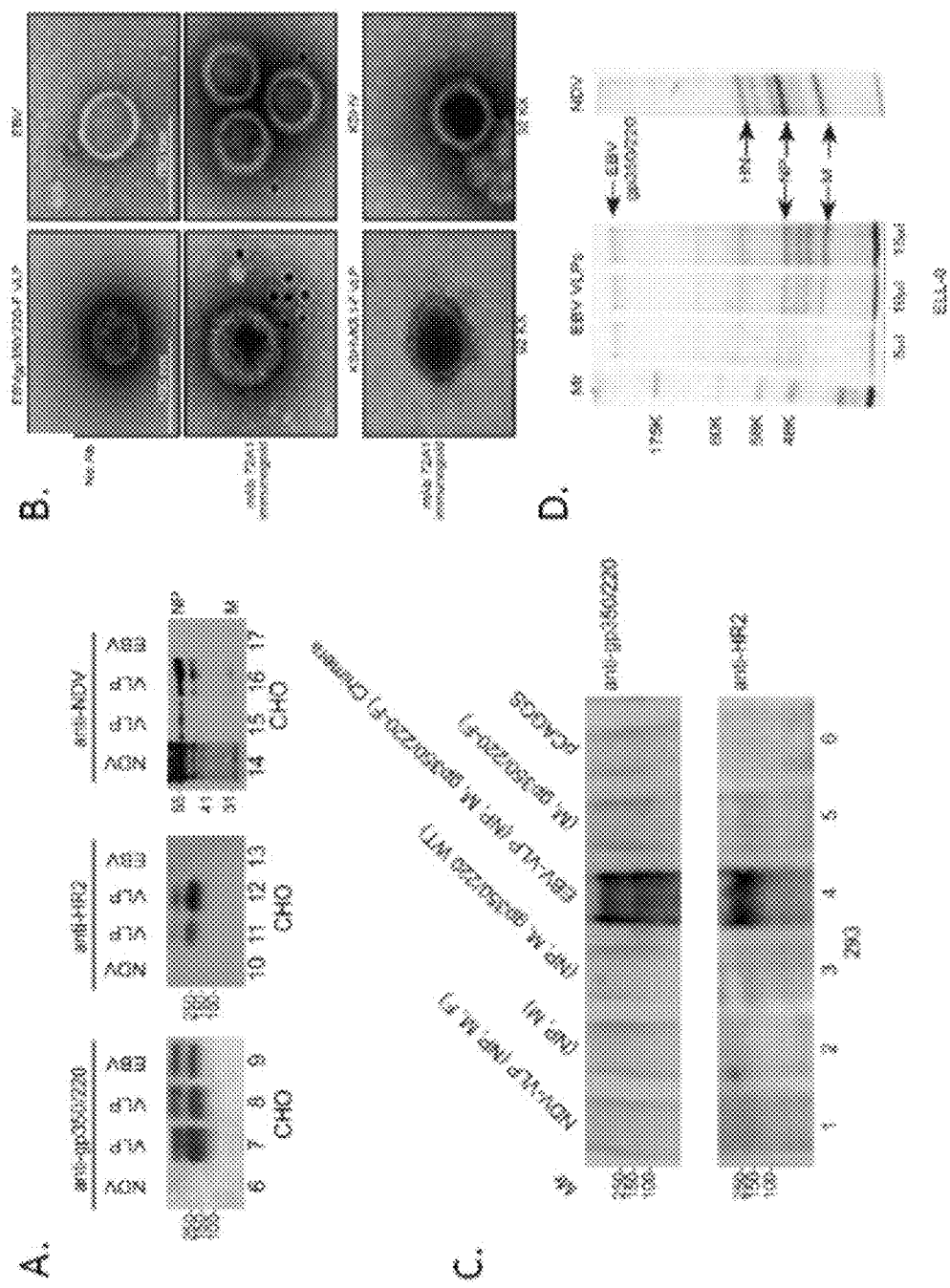
FIG. 75. Characterization of EBV-gp350/220-F VLPs. Cell supernatants from independent EBV VLP preparations were harvested daily between 24-96 h, concentrated, and purified by sucrose-gradient centrifugation followed by particle lysis and immunoblot analysis. (A) Supernatants produced in CHO cells were pooled and purified. Immunoblot indicating the presence of EBV gp350/220 ED, and NDV-F C-terminal peptides using mAb-72A1 anti-gp350/220 (left panel), polyclonal anti-HR2 (middle panel), and polyclonal anti-NDV (right panel), respectively. Each blot included lysates of purified EBV and ND, which served as controls. (B) Electron micrograph of negatively stained sucrose gradient purified EBV gp350/220-F VLPs prepared in CHO cells compared with native EBV using immunogold-coupled goat anti-mouse IgG binds the surface of a chimeric EBV gp350/220-F VLP and EBV (control). Image shows the structure and size of the chimeric VLP compared with EBV in the absence of antibody (top), and in the presence of mAb-72A1 anti-gp350/220 (middle), as well as a chimeric KSHV-derived VLP or KSHV. (C) Different combinations of pCAGGS plasmids encoding F, M, NP gp350/220 and gp350/220-F as indicated were co-transfected into 293T cells. Material released into the supernatant was pelleted and analyzed by immunoblot using anti-gp350/220 and anti-HR2 antibodies, Lane 1: NDV-VLP (NP, M, F), lane 2: NP, M, lane 3: NP, M, gp350/220 WT, lane 4: EBV VLP (NP, M, EBVgp350/220-F), lane 5: M, EBV gp350/220-F, lane 6: pCAGGS. Bands of the expected molecular weight were detected by both antibodies in lane 4 alone, indicating a chimeric EBV VLP specifically assembled and was released. (D) Silver stain of increasing amounts of purified chimeric VLPs released from ELL-0 cells compared with NDV. The position of EBV gp350/220-F protein, NDV-NP and -M are indicated by arrows. Molecular weight markers are indicated at left.

Following confirmation of plasma membrane expression, as required for particle assembly, pCAGGS-EBV gp350/220-F was co-transfected with NDV core proteins M, NP into CHO, 293 T or ELL-0 cell lines to generate chimeric VLPs as diagram in FIG. 75A. Particles from distinct preparations released into cell supernatants were purified, characterized by immunoblot (FIG. 75A, 75C): electron microscopy (FIG. 75B), and silver stain (FIG. 75D) as outlined (56). These analyses confirmed that proteins of correct sizes (350 and 220 kDa) were made and these VLPs are similar in size, shape and structure to the native virus, by negative staining and immunogold-conjugated antibody analysis.

Example 11

Visualization of EBV gp350/220-F VLP Attachment to CD21 and CD35 Bearing Cells

Figure 76:
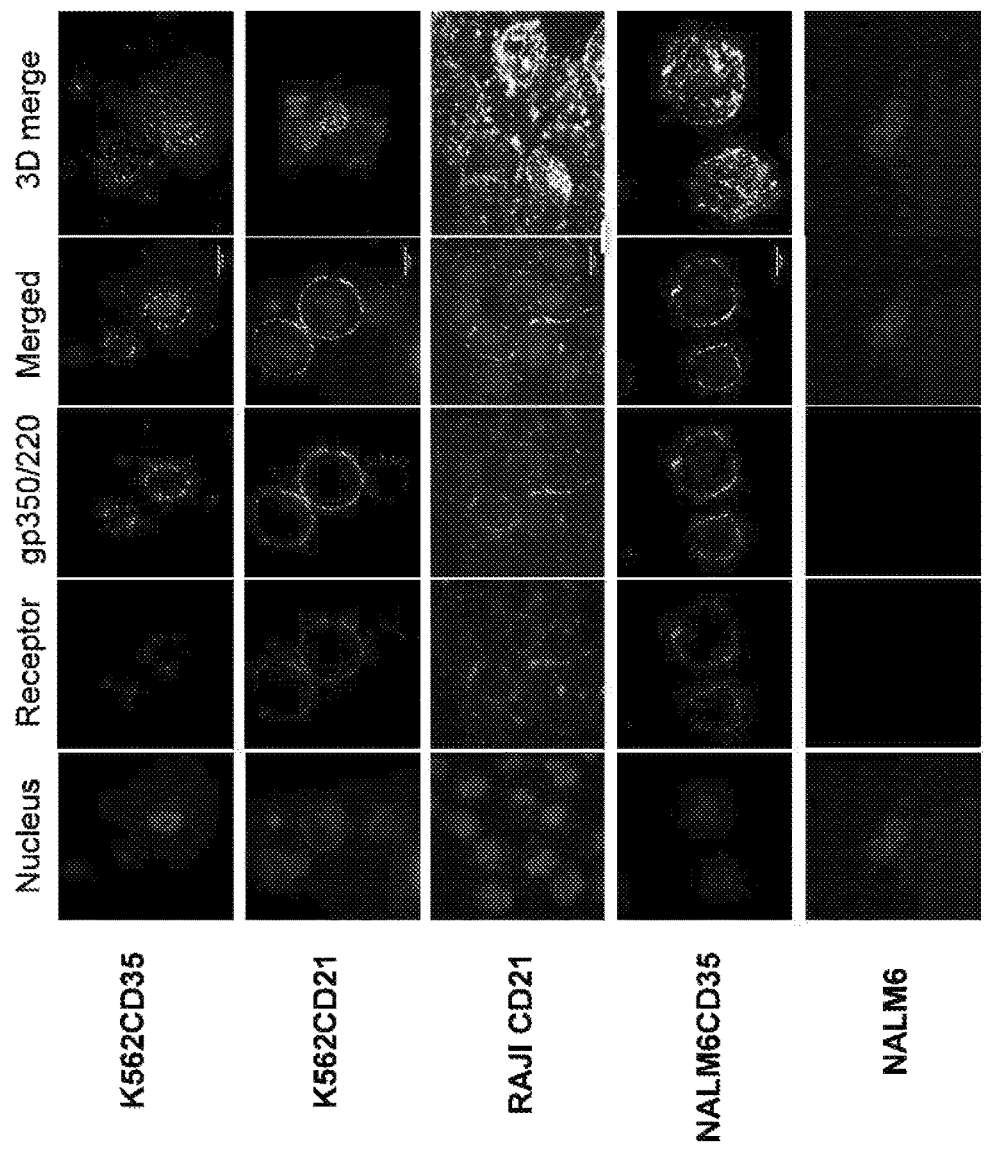
FIG. 76. Purified EBV gp350/220-F VLPs bind CD21 and CD35. Raji, Nalm6, and K562 cells lines transfected with either CD21 or CD35 were characterized and prepared as described (Ogembo et al., *Cell Reports* 2013; 371-385). Untransfected NALM6 cells were used as a control. The cells were stained with primary mAbs to either CD35 or CD21 depending on which complement receptor they had been transfected with followed by AF594-coupled goat Fab'2-F anti-mouse IgG (red). Next, attachment of EBV gp350/220-F VLPs was detected directly with AF488-coupled anti-gp350/220 (mAb-2L10) (green) that recognizes an epitope distal to the attachment site. Cell content was documented by nuclear staining with DAPI. Sequential confocal images showed that the chimeric VLP binds to CD21 or CD35 bearing cells whereas no binding to receptor negative Nalm6 cells was seen. Visualization of 3D merged images confirmed extensive co-localization (yellow) of the chimeric VLPs with both CD21 and CD35. Ogembo et al., *J. Trans. Med.* 2015; 1350.

EBV gp350/220 binds CD21 and/or CD35 on human cells (23, 26). To determine whether chimeric VLPs expressed from CHO cells retained the receptor-binding specificity of the virion envelope protein, we incubated EBV gp350/220-F VLPs with Raji, a latently EBV-infected B-cell line that naturally expresses high amounts of CD21 (23) and can be superinfected with EBV. In addition, a panel of receptor negative cell lines, Nalm6 and K562 (not shown), together with their CD21 or CD35 transfected sublines was investigated (26). Receptors (red) and VLPs (green) were visualized by indirect immunofluorescence using a confocal microscope for detection as shown in FIG. 76, EBV gp350/220 F VLPs abundantly bound Raji, no attachment to Nalm6 was detected. Nalm6CD21, Nalm6CD35 K562CD21 and K562CD36 all bound EBVgp350/220-F VLPs.

Example 12

Figure 77:
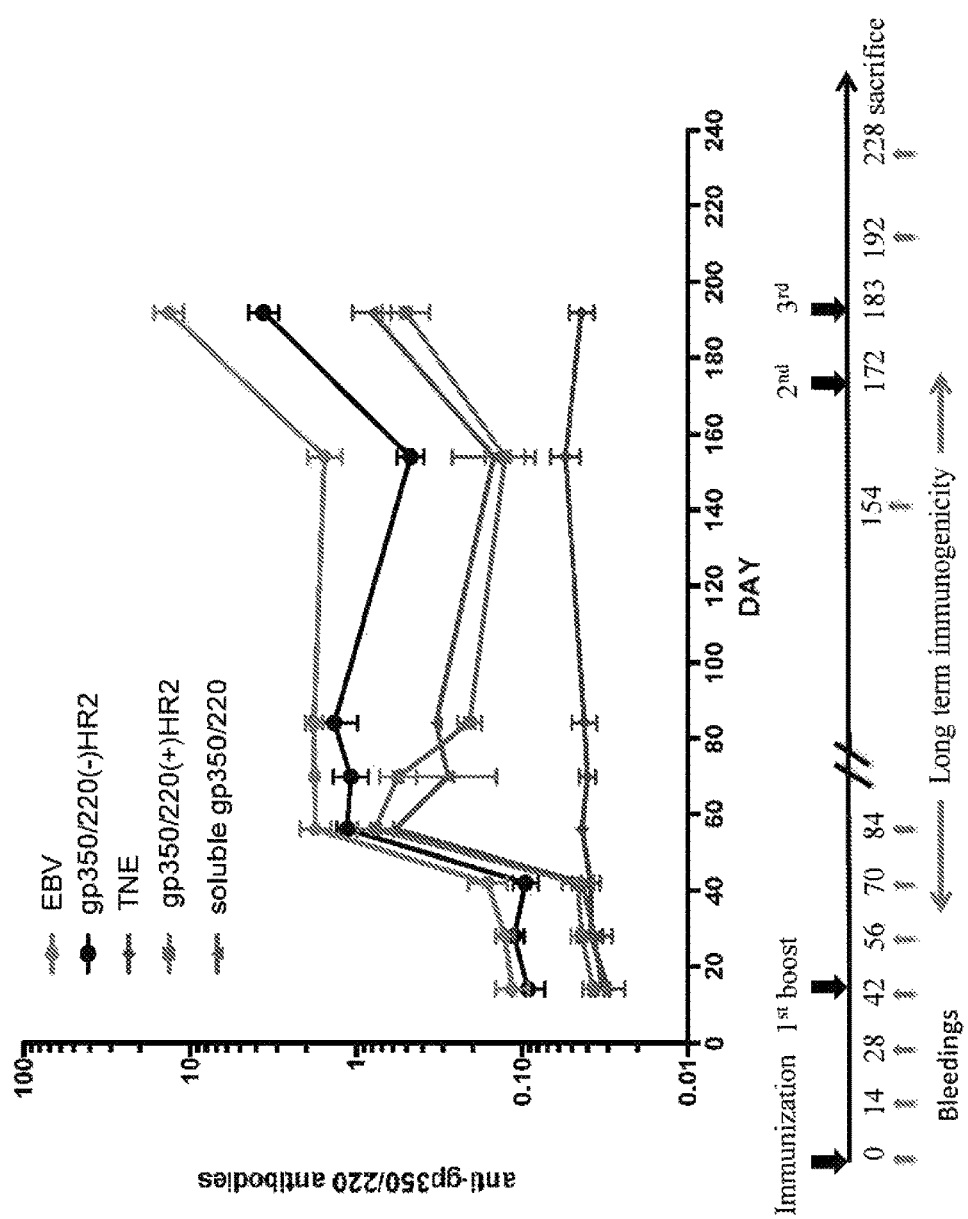
FIG. 77. Long-term IgG anti-gp350/220 antibodies are generated in mice immunized with EBV gp350/220-F VLPs, UV-EBV and soluble recombinant gp350/220 ED. Groups of five mice were immunized intraperitoneally with either EBV gp350/220(+)HR2 VLPs (green), EBV gp350/220(−)HR2 VLPs (black), inactivated UV-EBV (red), soluble recombinant gp350/220 ED (purple) or TNE, which served as vehicle control (blue). Each immunogen contained equivalent amounts of gp350/220, and both primary and booster vaccinations contained equivalent immunogen. Booster immunizations were performed on days 43, 172, 183 and 218 as indicated on the time line (bottom). All immunizations were performed in the absence of adjuvant. Anti-gp350/220 IgG titers were determined for 8 time points during the immunization schedule using ELISA. Ogembo et al., *J. Trans. Med.* 2015; 1350.

Development of Specific IgG Responses to EBV gp350/220 in BALB/c Mice Immunized with EBV gp350/220-F VLPs To determine whether chimeric VLPs elicit EBV gp350/220 specific antibody responses, a group of five mice were immunized intraperitoneally with 10 µg of EBV gp350/220-F VLP derived from CHO cells. UV-EBV and soluble gp350/220 ED served as positive controls and TNE as vehicle/negative control. Equivalence of gp350/220 protein content among the different immunogens was determined by both silver stain and Bradford assay (not shown). All animals received booster immunizations on days 43, 172, 183 and 218. Sera were collected two weeks post-boost. None of the animals displayed signs of local or systemic inflammation or changes in feeding or body weight that would indicate toxicity. Soluble recombinant gp350/220 ED served as the target antigen in an IgG ELISA. Anti-gp350/220 specific total IgG antibody titers significantly increased among mice immunized with the chimeric VLP, UV-EBV and soluble recombinant gp350/220 ED compared with pre-vaccination and control titers (FIG. 77). Historical controls using NDV-F VLPs as immunogen were non-reactive in gp350/220-based ELISAs (not shown). The increase in EBV-gp350/220 specific antibody appeared to plateau on day 84 after the initial boost, but then further increased after the second and third boosts. There was a significant difference in antibody titers of mice immunized with UV-EBV, compared with soluble gp350/220 ED and EBVgp350/220-F VLP, although the slopes of the response curves were similar. Gp350/220 specific antibody was absent from TNE-immunized mice. All gp350/220-based immunogens produced long-term gp350/220-specific responses, though mice immunized with native EBV maintained significantly higher titers of gp350/220 antibody compared to mice immunized with VLP or soluble recombinant protein.

Example 12

Anti EBV-Gp350/220 Antibodies Generated Following VLP Immunization Neutralize EBV Infection In Vitro.

Figure 78:
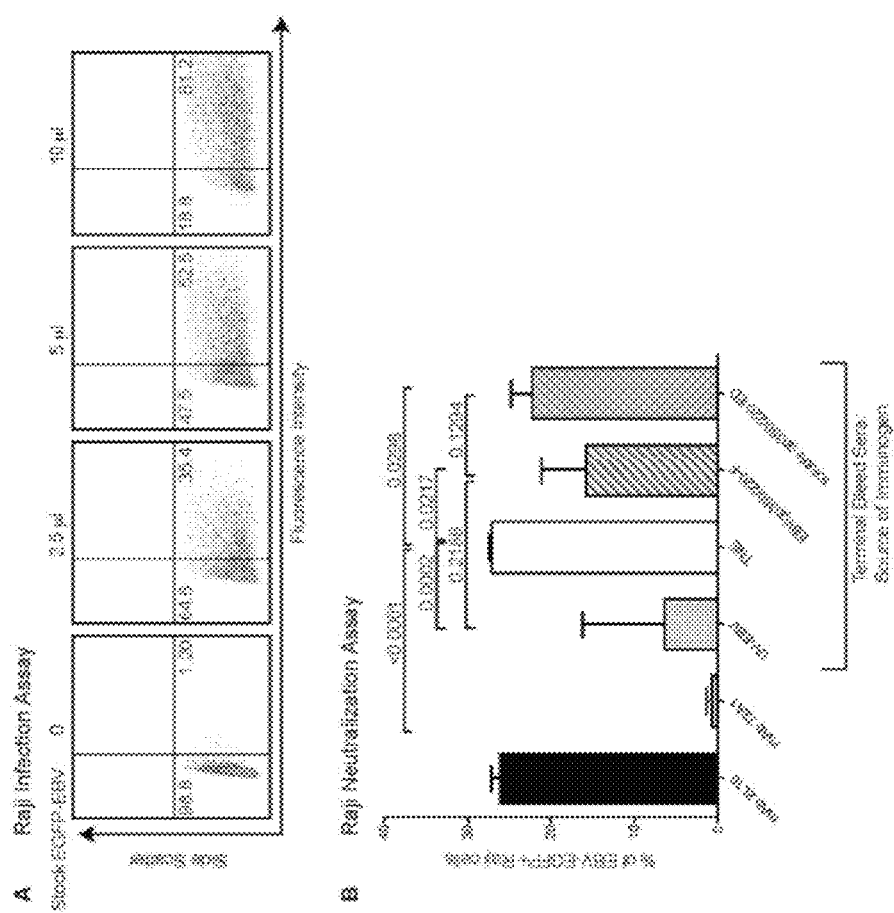
FIG. 78. Neutralization of EBV (EGFP-EBV) infection of Raji cells by pre-incubation with antibodies generated in response to EBV gp350/220-F VLP immunization. (A) EBV infection assay. Because EBV does not plaque, the infectivity of EGFP-EBV from frozen stock was directly quantitated by cytometry. Five microliters of stock virus in the absence of serum yielded ~50% infection (green fluorescence) 73 h after infection of Raji and was selected for neutralization experiments. (B) EBV neutralization assay. Pooled terminal bleed sera from groups of five BALB/c mice immunized with EBV gp350/220-F VLP, UV-EBV or soluble recombinant gp350/220 ED were pre-incubated with EGFP-EBV to assess neutralization (Methods). Infected cells were incubated at 37° C. for 72 h at which time EGFP positive Raji cells were enumerated by cytometry. X-axis indicates neutralizing antibody source. Y-axis displays percent of EGFP+ Raji cells post-infection. Terminal sera or mAb controls were pre-incubated 1:1 with EGFP-EBV resulting in further virus dilution such that ~25% of Raji cells were maximally infected (fluoresced green) in the presence of the non-blocking mAb-2L10 or TNE. Pre-incubation with mAb-72A1 (neutralizing) served as the positive control. Results are expressed as mean±standard deviations (SD). Horizontal black lines terminating in short vertical lines compare sets of neutralization experiments with p values indicated above the line. Ogembo et al., *J. Trans. Med.* 2015; 13:50.

It is well known that titer is not the sole gauge of a protective antibody response, as certain immunogens can induce antibodies that promote, rather than block infection and high affinity blocking antibodies can be highly effective at low titers (55). To evaluate the protective efficacy of antibodies generated in response to chimeric EBV-VLP, UV-EBV and soluble recombinant gp350/220 ED, we assessed the in vitro neutralizing antibody titers of sera boosted four times (collected day 228) with the immunogens described above. Because EBV does not plaque and large virus quantities are difficult to obtain, EBV was titered by the Raji cell infection assay (FIG. 78A). As predicted, pre-incubation of EGFP-EBV 1:1 with serum from TNE treated mice (negative control) produced ~27% fluorescence of Raji (FIG. 78B) as did pre-treatment with the non-neutralizing anti-gp350/220 mAb-2L10. In contrast when terminal sera from mice immunized with EBV gp350/220-F VLPs or UV-EBV was pre-incubated with EGFP-EBV, infection was reduced in comparison with TNE-immunized sera: 15% (p=0.0217) and 5% fluorescent cells (p=0.0002), respectively. As expected, purified mAb-72A1 (positive control) containing only IgG1 antibody directed to the gp350/220 attachment epitope was most effective at neutralization (1% fluorescent cells, p=<0.0001 compared with TNE). Antibodies generated after immunization with soluble recombinant gp350/220 ED were least effective (22% fluorescent cells, p=0.0298 versus TNE). Though the numbers are small, the comparative ability of antibodies generated in response to immunization with chimeric VLP versus UV-EBV to neutralize EBV infection of Raji cells was not significant (p=0.2188).

Because of the inability of sera from mice immunized with gp350/220 VLPs to effectively neutralize EBV infection in vitro (sterile condition), we reasoned that incorporation of EBVgH/gL or EBVgB with tumor-associated EBV antigens EBNA-1 and/or LMP2 as components of VLPs will enhance and sustain both humoral and T-cell responses. Furthermore, adoptive transfer of antigen-specific cytotoxic T lymphocytes (CTLs) offers safe and effective therapy for eradication of EBV-associated cancers, however, they do not expand or persist long term (42, 67). Thus, vaccination strategies that induce a robust antibody response and enhance EBV specific T-cell immunity are crucial for an effective EBV vaccine.

Figure 79:
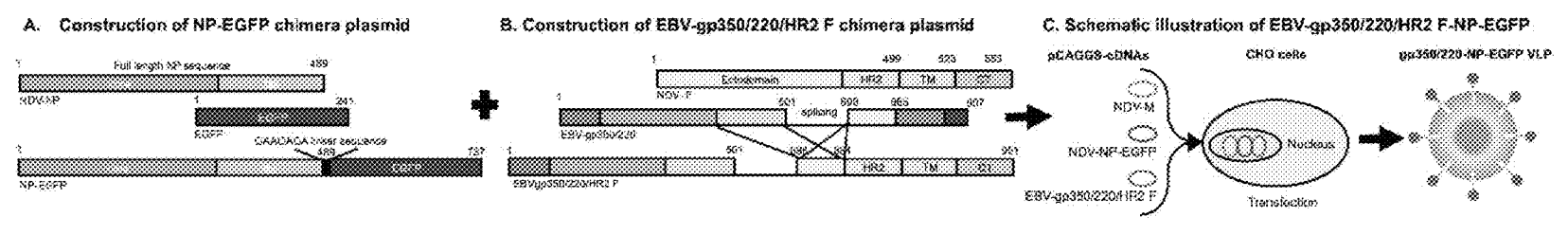
Figure 81:
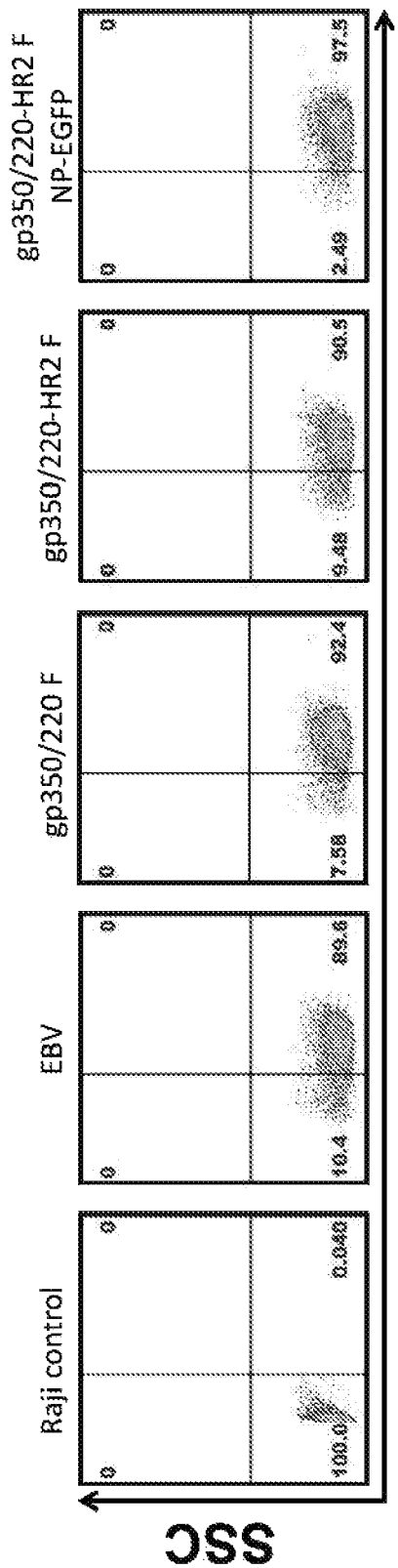
FIG. 81. EBV gp350/220-HR2 F EGFP VLPs binds CD21 on Raji cells. Raji cells expressing complement receptor type 2 (CD21) were incubated with purified EBV, EBVgp350/220 F, EBV gp350/220-HR2 F, or EBV gp350/220-HR2 F NP-EGFP VLPs. Attachment of EBV gp350/220 VLPs was next detected directly with AF488-coupled anti-gp350/220 (mAb-2L10) that recognizes an epitope distal to the attachment site. The results were measured by flow cytometry.

Immunization with inactivated virus particles or a subunit vaccine such as soluble recombinant proteins, in the absence of intracellular replication rarely induces robust CTL responses. An important reason for the poor immunogenicity is due to the difficult of an exogenous antigen to activate the major histocompatibility complex (MHC) class I pathway (68, 69). Typically, antigens that cannot gain access to the cytosol of the host cell activate the MHC class II pathway while antigens that are endocytosed are processed through the MHC class I pathway. VLPs are an interesting exception, since they can be efficiently processed by the MHC class I pathway through receptor mediated binding and entry (52, 70-72). This attribute makes VLPs promising candidates for the development of subunit vaccines, particularly for oncogenic viruses such as EBV. In nature, EBV only infects humans, however, humanized mouse models harboring functional human immune system components are easily infected with EBV (73). Many aspects of human EBV biology, including EBV latent infection, EBV-associated diseases, and T-cell-mediated immune responses are reproducible in humanized mice (74). Antibody responses are also elicited in humanized mice, however, the generation of antigen-specific IgG has been challenging (73). As a proof of concept, we first generated a fusion protein between NP and EGFP as illustrated (FIG. 79A), NDV-F and EBV gp350/220 (FIG. 79B). The NP-EGFP fusion protein was transfected into CHO cells together with gp350/220/HR2 F chimera, and NDV-M as illustrated in FIG. 79C. The transfected CHO cells expressed NP-EGFP protein (FIG. 80A), and efficiently assembled and released gp350/220-NP-EGFP VLPs into the supernatant when co-transfected with both pCAGGS-M and gp350/220. These gp350/220-NP-EGFP VLPs incorporated proteins of correct molecular sizes as confirmed by immunoblot (FIG. 80B) and bound CD21 expressed on the surface of Raji cells (FIG. 81).

Figure 82:
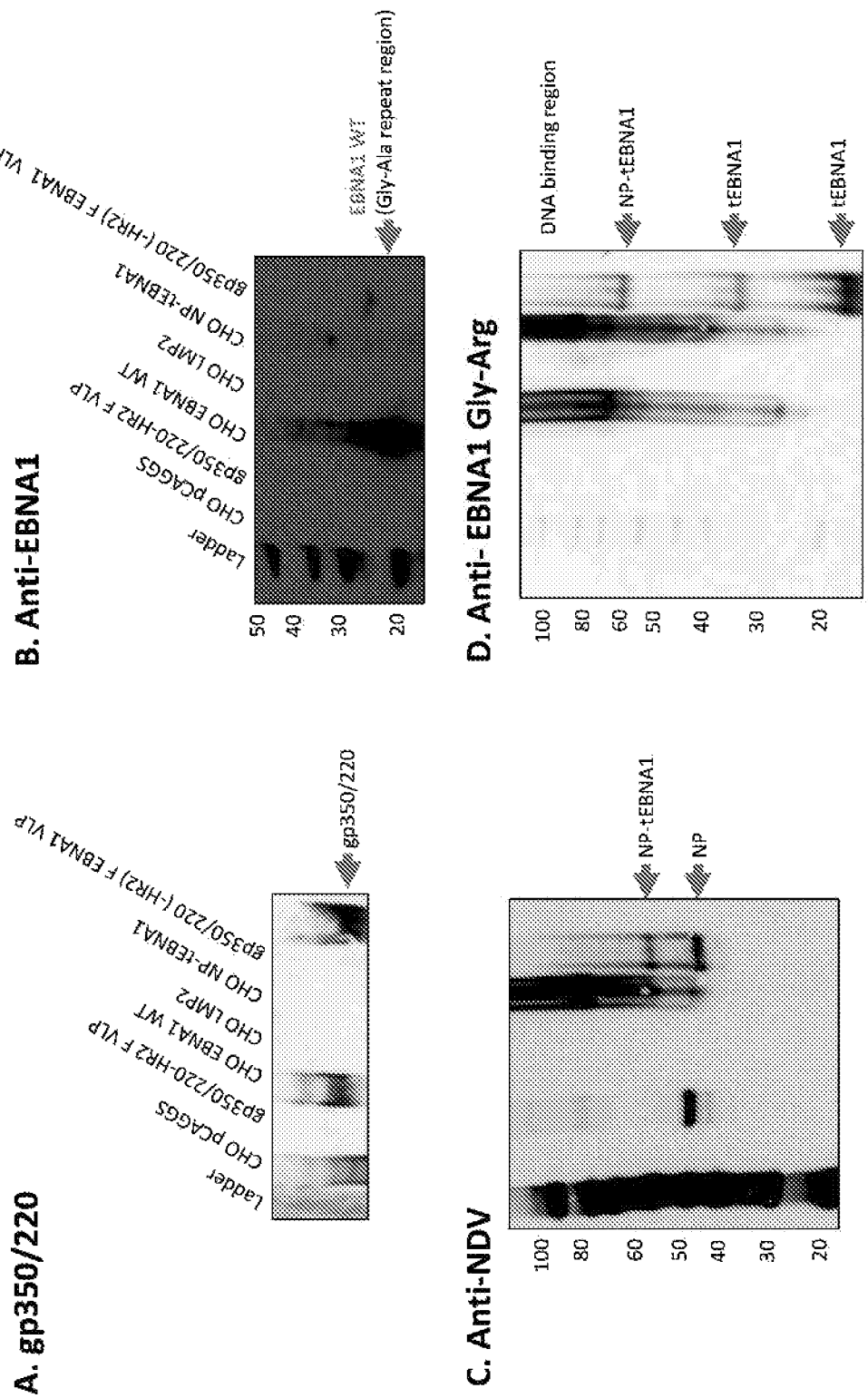
FIG. 82. Characterization of EBV gp350/220-EBNA1 VLPs. Purified EBV gp350/220-tEBNA1 VLPs were lysed in non-reducing Laemmli buffer and run on 4-20% SDS-agarose gel and proteins were detected via immunoblot. (A) mAb-72A1 anti-gp350/220, (B) mAb anti DNA binding domain EBV-EBNA1 (a gift from Dr. F. Grässer, Institut für Virologie, Germany), (C) polyclonal anti-NDV, and (D) anti-EBNA1 Gly-Arg regions Abs were used to detect respective proteins.
Figure 83:
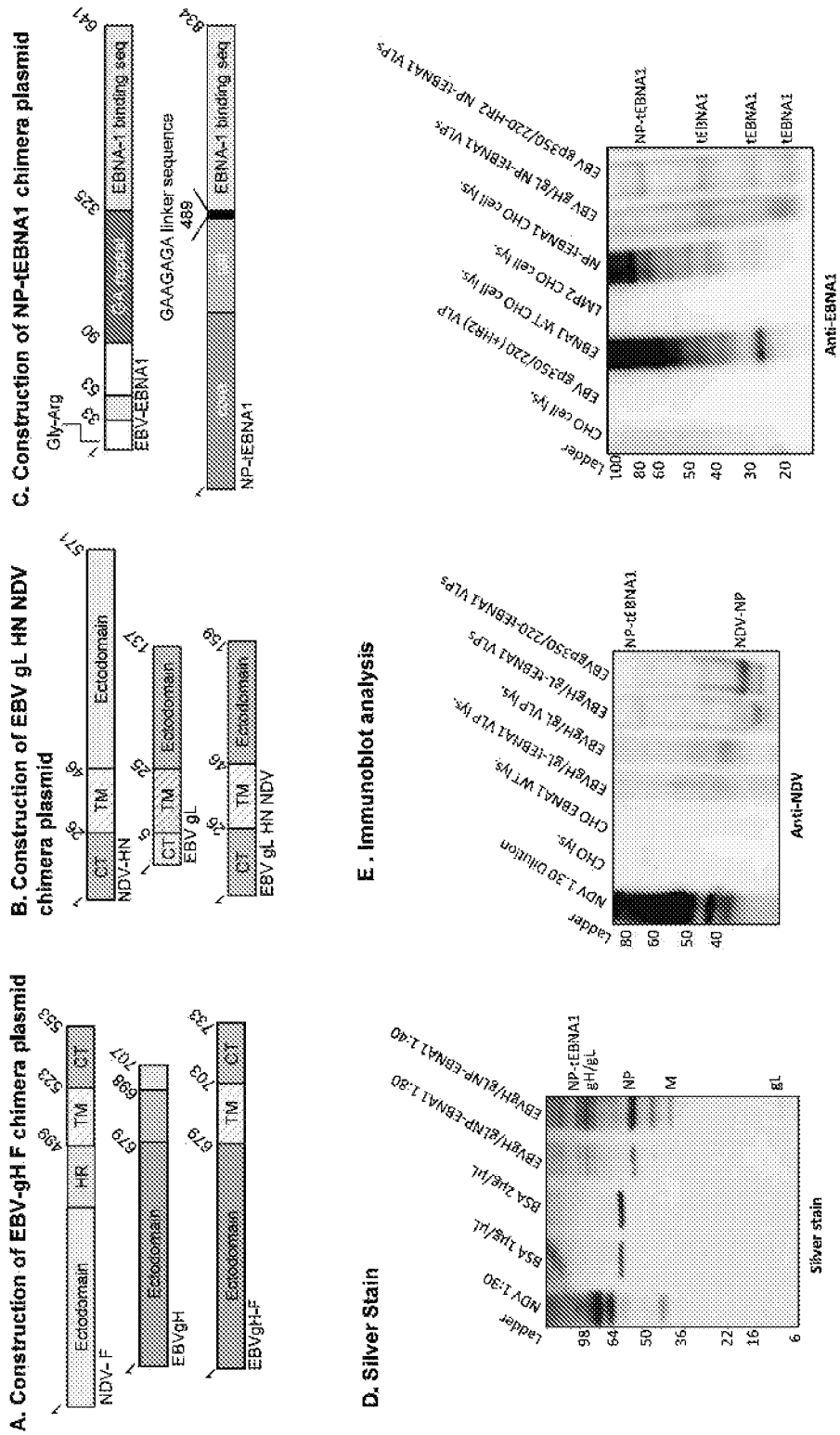
FIG. 83. Construction and schematic illustration of EBV gH/gL-NP-tEBNA1 VLP production and immunoblot detection of EBV gp350/220-NP-tEBNA1 VLPs. Construction and schematic of: (A) EBV gH-F, (B) EBV gL-HN, and (C) NP-tEBNA1 plasmids for VLP production. (D) EBV gp350/220-tEBNA1 VLPs were produced as outlined in FIG. 73. Purified EBV gp350/220-tEBNA1 VLPs were lysed on non-reducing Laemmli buffer and run on 4-20% SDS-agarose gel followed by silver stain and immunoblot. Polyclonal anti-NDV (top panel), mAb anti DNA binding domain EBV-EBNA1 (a gift from Dr. F. Grässer, Institut für Virologie, Germany, second panel), mAb-72A1 anti-gp350/220 (third panel) and anti-EBNA1 Gly-Arg regions (bottom panel) Abs were used to detect respective proteins.

Using a similar strategy, we incorporated a truncated form of EBNA1 (tEBNA1) in which the Gly-Ala region known to impair presentation of cis-linked sequences is deleted into EBVgp350/220 (FIG. 82) and EBVgH/gL-EBNA1 VLPs (FIG. 83). This confirmed that it is possible to generate VLPs containing antigens that are not expressed on the surface of the particles, in this case the latent EBV antigen EBNA1. The sequence of the antigen was present in detectable amounts in the supernatant of the transfected cells, and able to bind the antibody despite the deleted Gly-Ala region.

Figure 84:
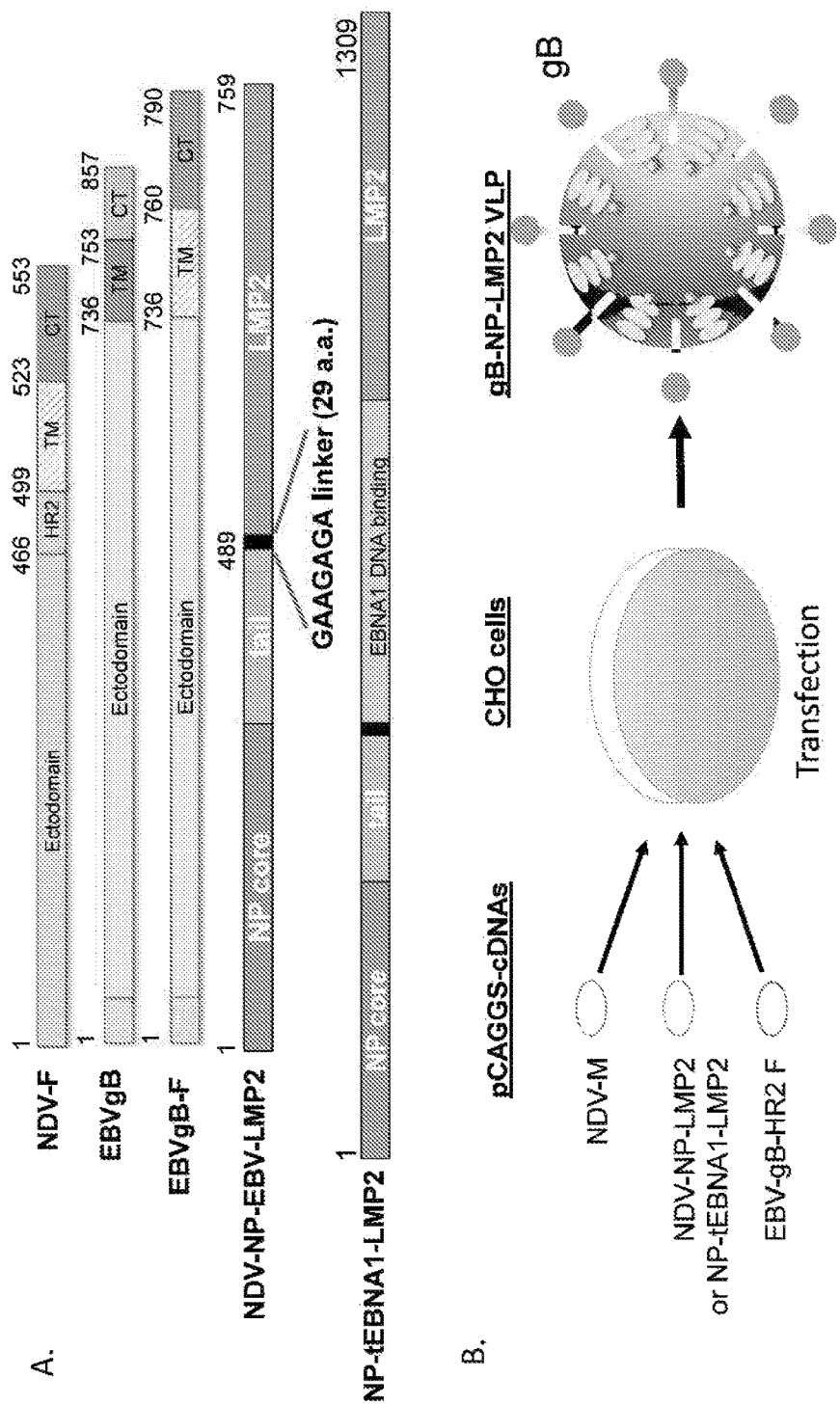
FIG. 84. Construction and schematic illustration of EBV gB-NP-LMP2 VLP or EBVgB-NP-tEBNA1-LMP2 VLP production. Schematic illustration of (A) NDV-F, EBVgB, EBVgB-F, NP-LMP2 and NO-tEBNA1-LMP2 plasmids for VLP production. (B) Schematic of cDNAs pCAGGS-NDV-M, -NP-tEBNA1-LMP2, and -gB-F chimera co-transfected into CHO cells for VLP production.
Figure 85:
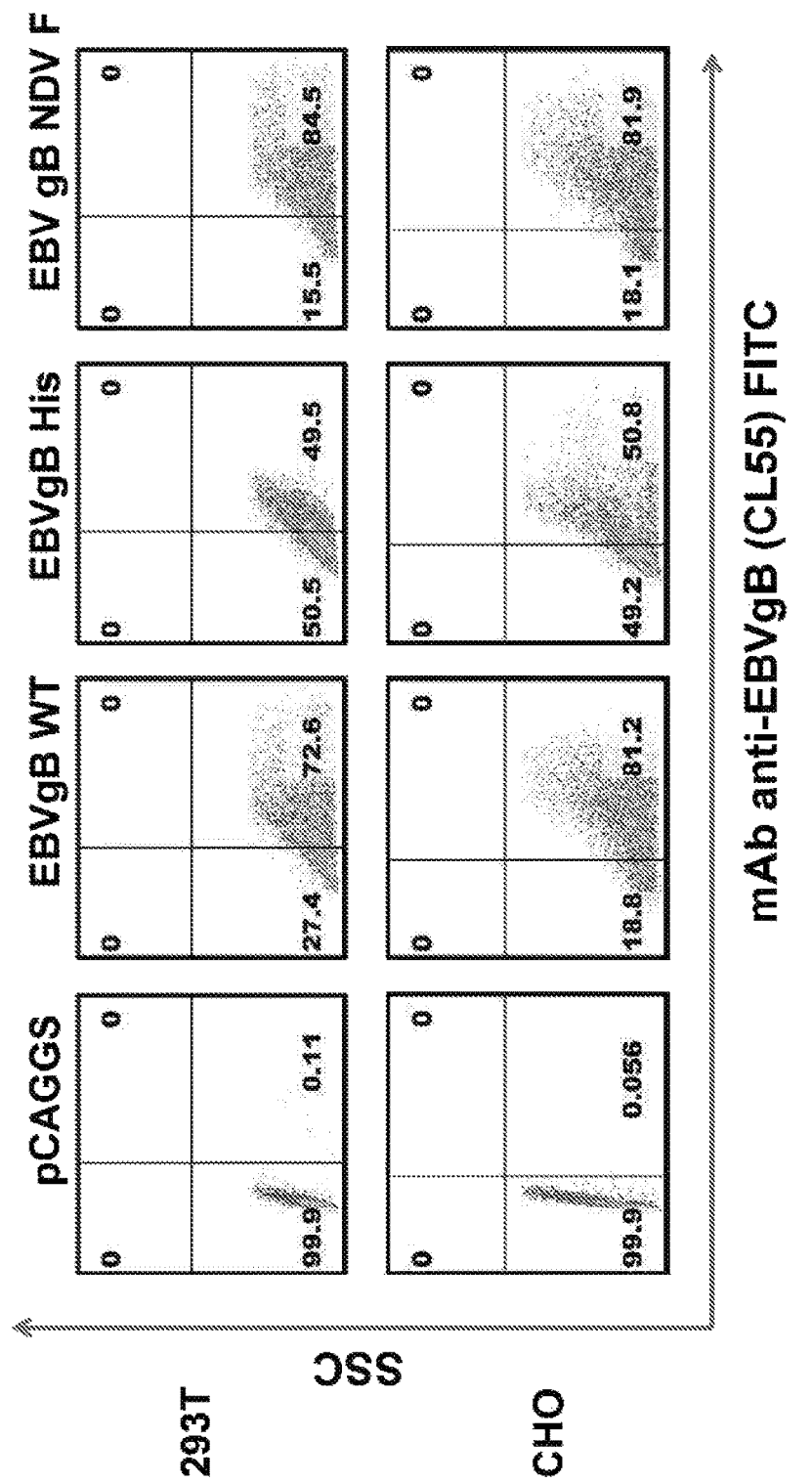
FIG. 85. Chimeric EBV gB-NDV F is well expressed on the surface of CHO cells. High expression of EBV gB-WT, EBV gB His and EBV gB-F on the surface of CHO cells. $10^6$ cells were transfected with 1 µg of EBV gB-WT. EBV gB His and EBV gB-F or pCAGGS alone (vector control). At 72 h post-transfection, cells were stained with mAb anti-gB (clone CL55) followed by AF488-coupled goat anti-mouse IgG (H+L) and analyzed by flow cytometry.
Figure 86:
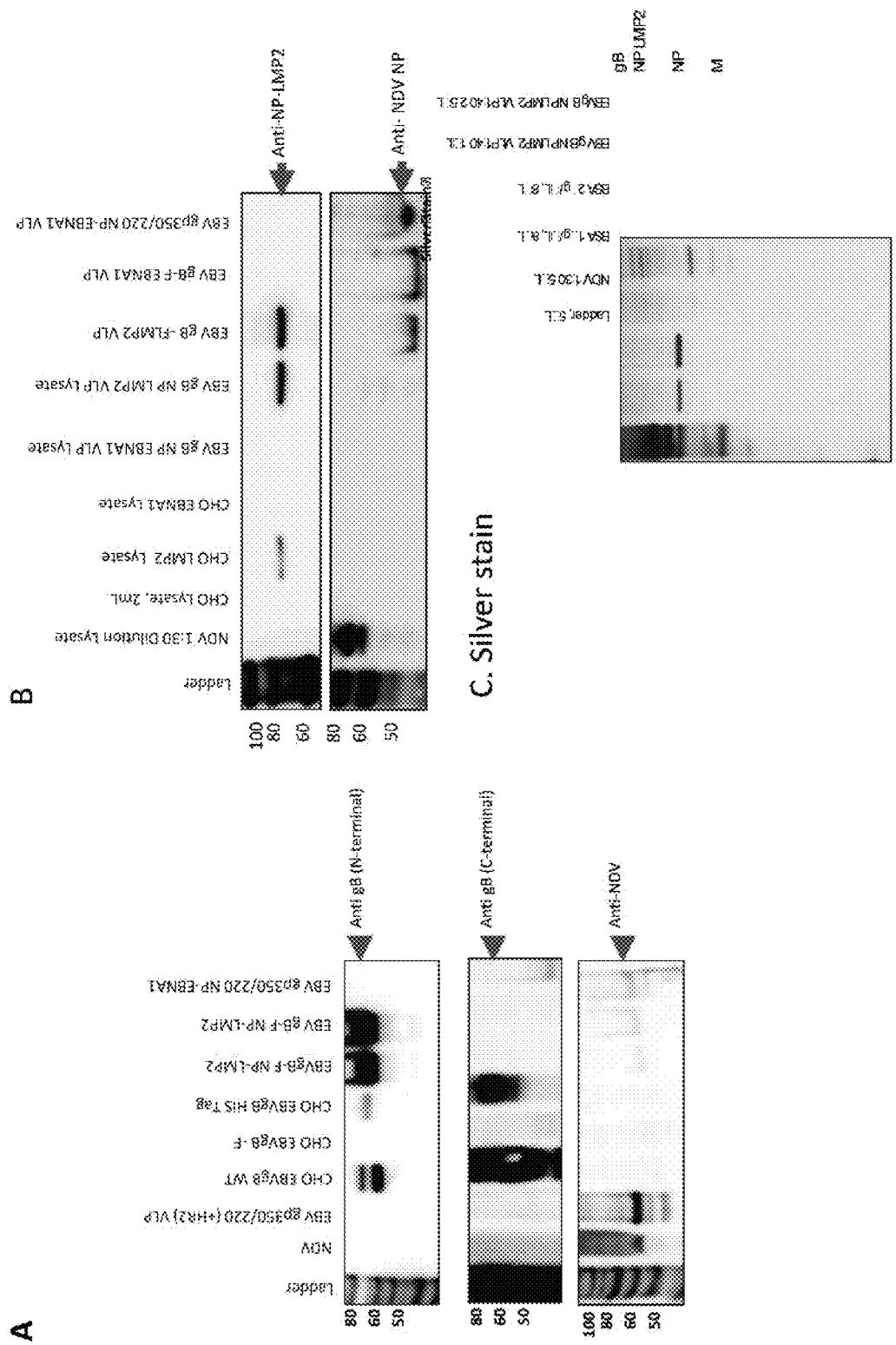
FIG. 86. Characterization of EBV gB-F NP-LMP2 and EBV gB-F NP-EBNA1 proteins were incorporated in VLPs. Characterization of EBV gp350/220-EBNA1 VLPs. Purified VLPs were lysed on non-reducing Laemmli buffer and run on 4-20% SDS-agarose gel followed by immunoblot. (A) mAb-CL55 and BA23 anti-B (top and middle panels), polyclonal anti-NDV bottom panel), (B) mAb anti EBV-LMP2 (top panel), and polyclonal anti-NDV (bottom panel) Abs were used to detect respective proteins. (C) Silver stain of increasing amounts of purified chimeric VLPs released from CHO cells compared with NDV. The position of EBV gB-F LMP2 protein, NDV-NP and -M are indicated by arrows. Molecular weight markers are indicated at left.

Construction and schematic illustration of pACGGS-EBV gB WT, chimeric pCAGSS-EBV gB-NDV F, chimeric pCA-GGS-NP-LMP2 plasmids is outlined in FIG. 84A-B. These constructs were transfected into CHO cells to determine expression of EBV gB on the cell surface was determined by cytometry (FIG. 85). We further confirmed that proteins (gB, LMP2, NP) were made and were of the right sizes (FIG. 86).

Figure 87:
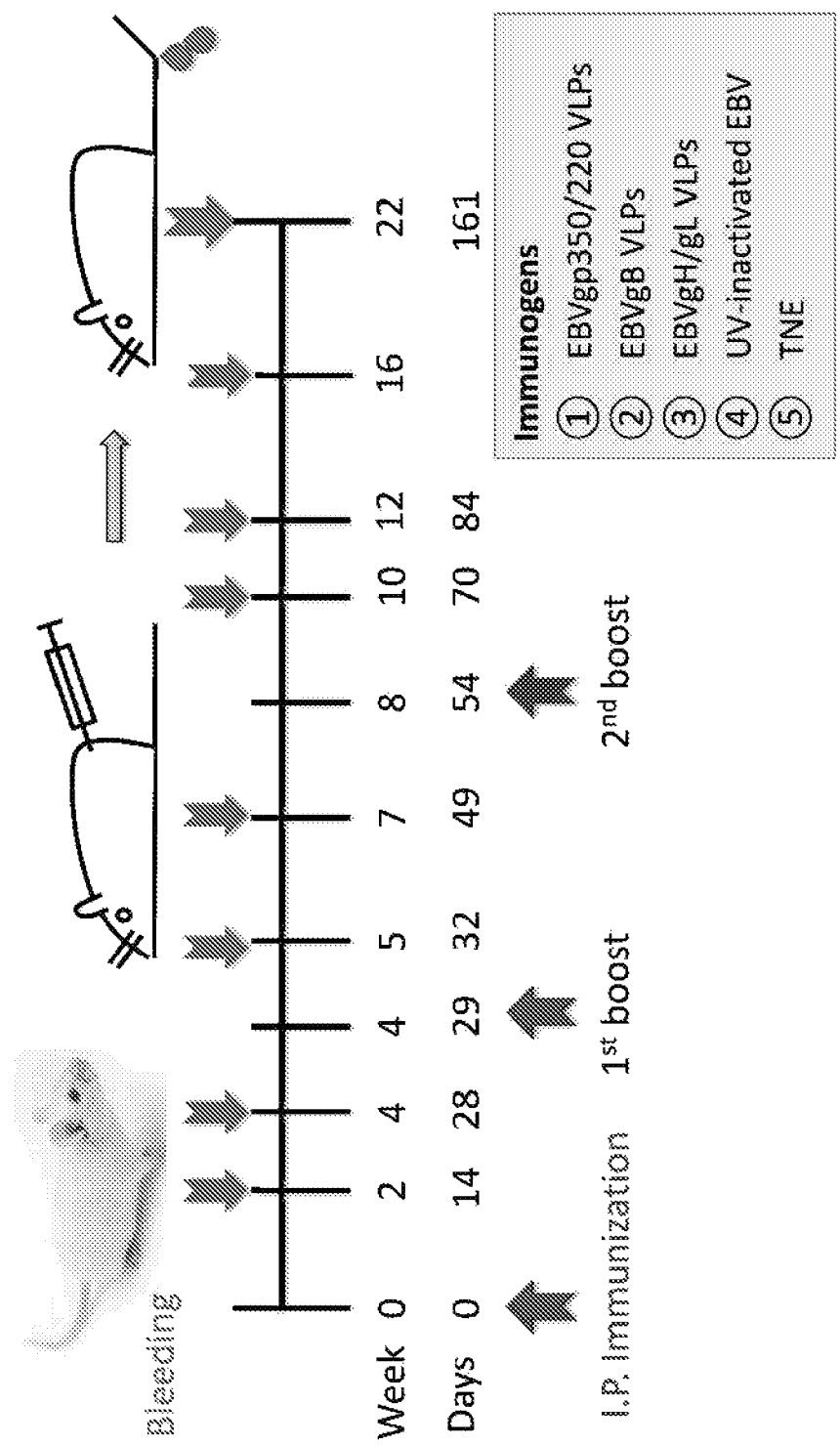
FIG. 87. Experimental layout and immunization of BALB/c mice with VLPs carrying EBV glycoproteins. BALB/c mice were immunized with 10 µg of EBV gH/gL-EBNA1 VLP, EBV gB-LMP2 VLP, or UV-inactivated EBV and boosted twice at days 26 and 56 without adjuvants. TNE served as a negative control for immunogen. At day 161 mice were sacrificed.
Figure 88:
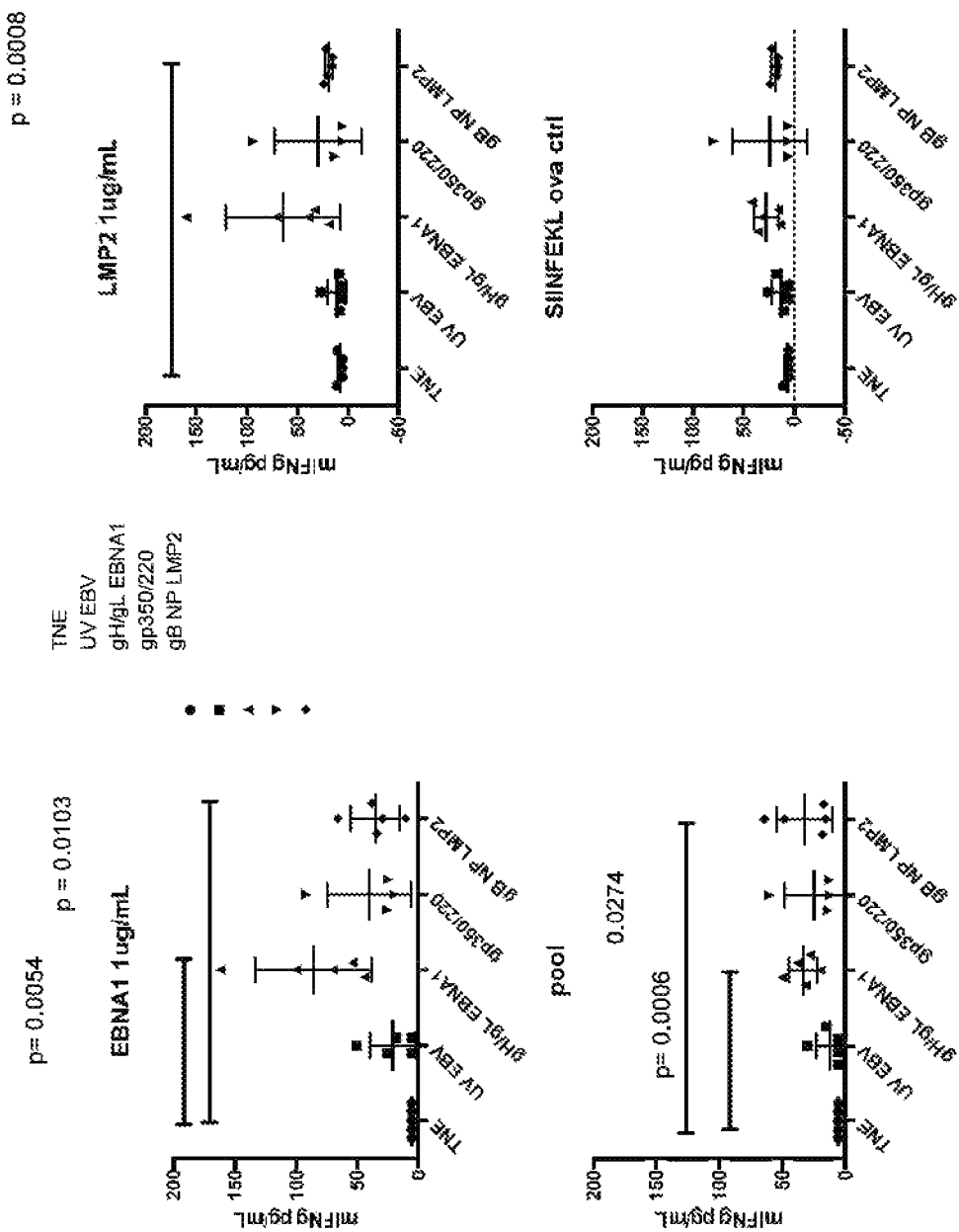
FIG. 88. Splenocytes from mice immunized with EBV gH/gL-EBNA1 VLPs and EBV gB-LMP2 VLPs generated significantly higher IFN-γ than mice immunized with UV-inactivated EBV and EBV gp350/220 VLPs. BALB/c mice were immunized with 10 µg of EBV gH/gL-EBNA1 VLP, EBV gB-LMP2 VLP, or UV-inactivated EBV and boosted twice at days 29 and 54 without adjuvants. TNF served as a negative control for immunogen. At day 161 mice were sacrificed and $5 \times 10^5$ splenocytes were stimulated in vitro with the corresponding as well as control peptides. 1 µg/mL of synthetic peptides derived from EBNA1$_{(HPVGEADYFEY)}$, LMP2$_{(CLGGLLTMV)}$ or Promix EBV peptide pool consisting of 26 peptides, each corresponding to a defined HLA class I-restricted T cell epitope from EBV were used in the assay. After overnight culturing, the supernatants were tested for IFN-γ release by ELISA. SIINFEKL ovalbumin was used as a negative control and concavalin A and IL1B wre used as model antigens.

Several studies on host immune responses against EBV have suggested that both B and T-cells immunity play a critical role in the protection against EBV infection and control of EBV-associated diseases. We hypothesized that incorporation of tumor-associated EBV antigens tEBNA-1 and LMP2 as components of VLPs will enhance and sustain both humoral and T-cell responses in BALB/c mice. To test our hypothesis, groups of 5 mice were immunized thrice at day 0, 29 and 54 intraperitoneally with 10 µg of EBVgH/gL-tEBNA1 VLPs, EBVgB-LMP2 VLPs, EBVgp350/220 VLPs, or UV-inactivated EBV resuspended in 500 µl of TNE. The animals were boosted twice at day 29 and 54 without adjuvants as illustrated (FIG. 87). TNE served as control for immunogens. At day 161 mice were sacrificed and $5\times10^5$ splenocytes were stimulated in vitro with the corresponding as well as control peptides. 1 µg/mL of synthetic peptides derived from EBNA1$_{(HPVGEADYFEY)}$, LMP2$_{(CLGGLLTMV)}$ or Promix EBV peptide pool consisting of 26 peptides, each corresponding to a defined HLA class I-restricted T cell epitope from EBV were used in the assay. After overnight culturing, the supernatants were tested for IFN-γ release by ELISA. SINFEKL ovalbumin was used as a negative control and concavalin A and IL1B were used as model antigens. Splenocytes from mice immunized with EBVgH/gL-EBNA1 VLPs and EBVgB-LMP2 VLPs generated significantly higher IFN-γ than mice immunized with UV-inactivated EBV and EBVgp350/220 VLPs (FIG. 88). Experiments are ongoing to determine the ability of the mice, sera from specific time points (including terminal bleed) to neutralize EBV expressing EGFP in an in vitro system as outlined (56).

REFERENCES

1. Rickinson A B, Kieff E. Epstein-Barr Virus. In: Knipe D, Howley P, editors, Fields Virology, Fifth ed. Philadelphia: Lippincott Wilkins and Williams; 2007, p. 2680-700.
2. Cohen J I, Fauci A S, Varmus H, Nabel G J, Epstein-Barr Virus: An Important Vaccine Target for Cancer Prevention, Science Translational Medicine. 2011; 3(107): 107fs7-fs7.
3. Kutok J, Wang F. Spectrum of Epstein-Barr virus-associated diseases. Annu Rev Pathol Mech Dis. 2006; 1:375-404.
4. Hjalgrim H, Friborg J, Melbye M. The epidemiology of EBV and its association with malignant disease. In: Arvin A, Capadelli-Fiume G, Mocarski E, Moore P S, Roizman B, Whitley R, et al., editors. Human Herpes viruses: Biology, Therapy, and Immunoprophylaxis. Cambridge 2007.
5. Luzuriaga K, Sullivan J L. Infectious mononucleosis. New England Journal of Medicine 2010; 362:1993-2000.
6. Babcock G J, Decker, L L, Volk M, Thorley-Lawson D A. EBV persistence in memory B cells in vivo. Immunity, 1998; 9(3): 395-404.
7. Goedert J J, Cote T R, Virgo P, Scoppa S M, Kingma D W, Gail M H, et al. Spectrum of AIDS-associated malignant disorders. Lancet. 1998; 351(9119): 1833-9, Epub 1998 Jul. 4. PubMed PMID: 9652666.
8. CotéT R, Biggar R J, Rosenberg P S, Devesa S S, Percy C, Yellin F J, et al. Non-Hodgkin's lymphoma among people with AIDS: Incidence, presentation and public health burden. International Journal of Cancer, 1998; 73(5):645-50.
9. Gottschalk S, Rooney C M, Heslop H E. Post-transplant lymphoproliferative disorders. Annu Rev Med. 2005; 56:29-44.
10. Cohen J I, Epstein-barr virus vaccines. Clinical & translational immunology. 2015; 4(1):e32, Epub 2015 Feb. 12, doi: 10.1038/cti.2014.27. PubMed PMID: 25671130; PubMed Central PMCID: PMC4318489.
11. Balfour H H, Jr. Progress, prospects, and problems in Epstein-Barr virus vaccine development. Curr Opin Virol. 2014:6C:1-5. Epub 2014 Mar. 19. doi; 10.1016/j.coviro.2014.02.006. PubMed PMID: 24632197.
12. Biggar R J, Henle G, Böcker j, Lennette E T, Fleisher G, Henle W. Primary Epstein-Barr virus infections in African infants. II. Clinical and serological observations during seroconversion. International Journal of Cancer. 1978; 22(3): 244-50.
13. Biggar R J, Henle W, Fleisher G, Böcker J, Lennette E T, Henle G. Primary Epstein-Barr virus infections in african infants. I. Decline of maternal antibodies and time of infection, International Journal of Cancer. 1978; 22(3): 239-43.
14. Gu S Y, Huang T M, Ruan L, Miao Y H, Lu H, Chu C M, et al. First EBV vaccine trial in humans using recombinant vaccina virus expressing the major membrane antigen. Dev Biol Stand. 1995; 84:171-7. Epub 1995 Jan. 1. PubMed PMID: 7796951.
15. Moutschen M, Leonard P, Sokal E M, Smets F, Haumont M, Mazzu P, et al. Phase I/II studies to evaluate safety and immunogenicity of a recombinant gp350 Epstein-Barr virus vaccine in healthy adults. Vaccine. 2007; 51(24):

16. Res L, Tizard E J, Morgan A J, Cubitt W D, Finerty S, Oyewole-Eletu T A, et al. A phase I trial of epstein-barr virus gp350 vaccine for children with chronic kidney disease awaiting transplantation. Transplantation. 2009; 88(8):1025-9. Epub 2009 Oct. 27. doi: 10.1097/TP.0b013c318b9d918 00007890-200910270-00013 [pii]. PubMed PMID: 19855249.

17. Sokal E M, Hoppenbrouwers K, Vandermeulen C, Moutschen M, Léonard P, Moreels A, et al. Recombinant gp350 vaccine for infectious mononucleosis; a phase 2, randomized, double-blind, placebo-controlled trial to evaluate the safety, immunogenicity, and efficacy of an Epstein-Barr virus vaccine in healthy young adults. Journal of Infectious Diseases. 2007; 196(12): 1749-53.

18. Janz A, Oczel M, Kurzeder C, Mautner J, Pich D, Kost M, et al. Infectious Epstein-Barr virus lacking major glycoprotein BLLF1 (gp350/220) demonstrates the existence of additional viral ligands. Journal of virology, 2000; 74(21): 1014-52. Epub 2000 Oct. 12. PubMed PMID: 11024143; PubMed Central PMCID: PMC102053.

19. Borza C M, Hutt-Fletcher L M. Alternate replication in B cells and epithelial cells switches tropism of Epstein-Barr virus. Nature medicine. 2002; 8(6): 594-9. Epub 2002 Jun. 4 doi: 10.1038/nm0602-594. PubMed PMID: 12042810.

20. Chesnokova L S, Hutt-Fletcher L M. Fusion of Epstein-Barr virus with epithelial cells can be triggered by alphavbeta5 in addition to alpha beta6 and alphavbet8, and integrin binding triggers a conformational change in glycoprotein gHgL. Journal of virology. 2011; 85(24): 13214-23. Epub 2011 Oct. 1. doi: 10.1138/JV1.05580-11. PubMed PMID: 21957301; PubMed Central PMCID: PMC3233123.

21. Miller N, Hutt-Fletcher L M. A monoclonal antibody to glycoprotein gp85 inhibit fusion but not attachment of Epstein-Barr virus, Journal of virology. 1988; 62(7): 2366-72. Epub 1988 Jul. 1. PubMed PMID: 2836619; PubMed Central PMCID: PMC253393.

22. Wang H B, Zhang H, Zhang J P, Li Y, Zhao B, Feng G K, et al. Neuropilin 1 is an entry factor that promotes EBV infection of nasopharyngeal epithelial cells. Nature communications. 2015; 6:6240. Epub 2015 Feb. 12. doi: 10.1038/ncomms7240. PubMed PMID: 25670642.

23. Fingeroth J D, Weis J J, Tedder T F, Strominger J L, Biro P A, Fearon D T. Epstein-Barr virus receptor of human B lymphocytes is the C3d receptor CR2. Proc Natl Acad Sci USA. 1984; 81(14): 4510-4. Epub 1984 Jul. 1. PubMed PMID: 6087328; PubMed Central PMCID: PMC345620.

24. Nemerow G R, Cooper N R. Early events in the infection of human B lymphocytes by Epstein-Barr virus; the internalization process. Virology. 1984; 132(1): 186-98. Epub 1984 Jan. 15. PubMed PMID: 6320532.

25. Nemerow G R, Houghten R A, Moore M D, Cooper N R. Identification of an epitope in the major envelope protein of Epstein-Barr virus that mediates viral binding to the B lymphocyte EBV receptor (CR2). Cell. 1989; 56(3): 369-77.

26. Ogemo J G, Kannan L, Ghiran I, Nicholson-Weller A, Finberg R W, Tsokos G C, et al. Human complement receptor type 1/CD35 is an Epstein-Barr Virus receptor. Cell Rep. 2013; 3(2): 371-85. Epub 2013 Feb. 19. doi: 10.1016/j.celrep.2013.01.023. PubMed PMID: 23416052; PubMed Central PMCID: PMC3633082.

27. Tanner J, Weis J, Fearon D, Whang Y, Kieff E. Epstein-Barr virus gp350/220 binding to the B lymphocyte C3d receptor mediates adsorption, capping, and endocytosis. Cell. 1987; 50(2): 203-13. Epub 1987 Jul. 17. doi: 0092-8674(87)90216-9 [pii]. PubMed PMID: 3036369.

28. Eisenberg R J, Atanasiu D, Cairns T M, Gallagher J R, Krummenacher C, Cohen G H. Herpes virus fusion and entry: a story with many characters. Viruses. 2012; 4(5): 800-32. Epub 2012 Jul. 4. doi: 10.3390/v4050800. PubMed PMID: 22754650; PubMed Central PMCID: PMC3386629.

29. Li Q, Turk S M, Hutt-Fletcher L M. The Epstein-Barr virus (EBV) BZLF2 gene product associates with the gH and gL homologs of EBV and carries an epitope critical to infection of B cells but not of epithelial cells. Journal of virology. 1994; 69(7): 3987-94. Epub 1995 Jul. 1. PubMed PMID: 7539502; PubMed Central PMCID: PMC189130.

30. Wang X, Hutt-Fletcher L M. Epstein-Barr virus lacking glycoprotein gp42 can bind to B cells but is not able to infect. Journal of virology. 1998; 72(1): 158-63.

31. Molesworth S J, Lake C M, Borza C M, Turk S M, Hutt-Fletcher L M. Epstein-Barr virus gH is essential for penetration of B cells but also plays a role in attachment of virus to epithelial cells. Journal of virology. 2000; 74(14): 6324-32. Epub 2000 Jun. 23. PubMed PMID: 10864642; PubMed Central PMCID: PMC112138.

32. Wu L, Borza C M, Hutt-Fletcher L M. Mutations of Epstein-Barr virus gH that are differentially able to support fusion with B cells or epithelial cells. Journal of virology. 2005; 79(17): 10923-30. Epub 2005 Aug. 17. doi: 10.1128/JV79.17.10923-10930.2005. PubMed PMID: 16103144; PubMed Central PMCID: PMC1193614.

33. Fuller A O, Santos R E, Spear P G. Neutralizing antibodies specific for glycoprotein H of herpes simplex virus permit viral attachment to cells but prevent penetration. Journal of virology. 1989; 63(8): 3435-43. Epub 1989 Aug. 1. PubMed PMID: 2545914; PubMed Central PMCID: PMC250919.

34. Gompels U A, Carss A L, Saxby C, Hancock D C, Forrester A, Minson A C. Characterization and sequence analyses of antibody-selected antigenic variants of herpes simplex virus show a conformationally complex epitope on glycoprotein H. Journal of virology. 1991; 65(5): 2393-401. Epub 1991 May 1. PubMed PMID: 1707982; PubMed Central PMCID: PMC240591.

35. Nokta M, Tolpin M D, Nadler P I, Pollard R B. Human monoclonal anti-cytomegalovirus (CMV) antibody (MSL 109): enhancement of in vitro foscarnet- and ganciclovir-induced inhibition of CMV replication. Antiviral research. 1994; 24(1); 17-26. Epub 1994 Jan. 1. PubMed PMID: 7944310.

36. Wussow F, Chiuppesi F, Martinez J, Campo J, Johnson E, Flechsig C, et al. Human cytomegalovirus vaccine based on the envelope gH/gL pentamer complex 2014.

37. Naranatt P P, Akula S M, Chandran B. Characterization of gamma2-human herpesvirus-8 glycoproteins gH and gL. Archives of virology. 2002; 147(7): 1349-70. Epub 2002 Jul. 12. doi: 10.1007/s00705-002-0813-7. PubMed PMID: 12111412.

38. Kirschner A N, Omerovic J, Popov B, Longnecker R, Jardetzky T S. Soluble Epstein-Barr virus glycoproteins gH, gL, and gp42 form a 1:1:1 stable complex that acts like soluble gp42 in B-cell fusion but not in epithelial cell fusion. Journal of virology. 2006; 80(19): 9444-54. Epub 39. Rowe C L, Connolly S A, Chen J, Jardetzky T S, Longnecker R. A soluble form of Epstein-Barr virus gH/gL inhibits EBV-induced membrane fusion and does not function in fusion. Virology. 2013; 436(1): 118-26. Epub 2012 Dec. 4. doi: 10.1016/j.virol.2012.10.039. PubMed PMID: 23200314; PubMed Central PMCID: PMC3545092.

40. Li Q, Spriggs M K, Kovats S, Turk S M, Comeau M R, Nepom B, et al. Epstein-Barr virus uses HLA class II as a cofactor for infection of B lymphocytes. Journal of virology. 1997; 71(6): 4657-62.

41. Icheva V, Kayser S, Wolff D, Tuve S, Kyzirakos C, Bethge W, et al. Adoptive transfer of Epstein-Barr virus (EBV) nuclear antigen 1-specific T cells as treatment for EBV reactivation and lymphoproliferative disorders after allogeneic stem-cell transplantation. Journal of Clinical Onocology, 2012; JCO. 2011.39.8495.

42. Heslop H E, Ng C Y, Li C, Smith C A, Loftin S K, Krance R A. et al. Long-term restoration of immunity against Epstein-Barr virus infection by adoptive transfer of gene-modified virus-specific T lymphocytes. Nature medicine. 1996; 2(5): 551-5.

43. Icheva V, Kayser S, Wolff D, Tuve S, Kyzirakos C, Bethge W, et al. Adoptive transfer of epstein-barr virus (EBV) nuclear antigen 1-specific t cells as treatment for EBV reactivation and lymphoproliferative disorders after allogeneic stem-cell transplantation. J Clin Oncol. 2013; 31(1): 39-48. Epub 2012 Nov. 22. doi: 10.1200/JCO.2011.39.8495. PubMed PMID: 23169501.

44. Taylor G S, Jia H, Harrington K, Lee L W, Turner J, Ladell K, et al. A Recombinant Modified Vaccinia Ankara Vaccine Encoding Epstein-Barr Virus (EBV) Target Antigens: A Phase I Trial in UK Patients with EBV-Positive Cancer. Clin Cancer Res. 2014; 20(19): 5009-22. Epub 2014 Aug. 16. doi: 10.1158/1078-0432.CCR-14-1122-T. PubMed PMID: 25124688.

45. Fogg M H, Wirth L J, Posner M, Wang F. Decreased EBNA-1-specific CD8+ T cells in patients with Epstein-Barr virus-associated nasopharyngeal carcinoma. Proc Natl Acad Sci USA. 2009; 106(9): 3318-23. Epub 2009 Feb. 13. doi: 10.1073/pnas.0813320106. PubMed PMID: 19211798; PubMed Central PMCID: PMC2651339.

46. Long H M, Chagoury O L, Leese A M, Ryan G B, James E, Morton L T, et al. MHC II tetramers visualize human CD4+ T cells responses to Epstein-Barr virus infection and demonstrate atypical kinetics of the nuclear antigen EBNA1 response. The Journal of experimental medicine. 2013; 210(5): 933-49. Epub 2013 Apr. 10. doi: 10.1084/jem.20121437. PubMed PMID: 23569328; PubMed Central PMCID: PMC3646497.

47. Lee S P, Brooks J M, Al-Jarrah H, Thomas W A, Haigh T A, Taylor G S, et al. CD8 T cell recognition of endogenously expressed Epstein-Barr virus nuclear antigen 1. The Journal of experimental medicine. 1004; 199(10): 1409-20. Epub 2004 May 19. doi: 10.1084/jem.2004121. PubMed PMID: 19148339; PubMed Central PMCID: PMC2211813.

48. Taylor G S, Haigh T A, Gudgeon N H, Phelps R J, Lee S P, Steven N M, et al. Dual stimulation of Epstein-Barr Virus (EBV)-specific CD4+- and CD8+-T-cell responses by a chimeric antigen construct: potential therapeutic vaccine for EBV-positive nasopharyngeal carcinoma. Journal of virology. 2004; 78(2): 768-78. Epub 2003 Dec. 25. PubMed PMID: 14694109; PubMed Central PMCID: PMC368843.

49. Apcher S, Daskalogianni C, Manoury B, Fahraeus R. Epstein-Barr virus-encoded EBNA1 interference with MHC class I antigen presentation reveals a close correlation between mRNA translation initiation and antigen presentation. PLoS Pathog. 2010; 6(10): c1001151. Epub 2010 Oct. 27. doi: 10.1371/journal.ppat.1001151. PubMed PMID: 20976201; PubMed Central PMCID: PMC2954899.

50. Hui E P, Taylor G S, Jia H, Ma B B, Chan S L, Ho R, et al. Phase I trial of recombinant modified vaccinia ankara encoding Epstein-Barr viral tumor antigens in nasopharyngeal carcinoma patients. Cancer Res. 2013; 73(6): 1676-88. Epub 2013 Jan. 26. doi: 10.1158/0008-5472.CAN-12-2448. PubMed PMID: 23348421.

51. Pavlova S, Feederic R, Gartner K, Fuchs W, Granzow H, Delecluse H J. An Epstein-Barr virus mutant produces immunogenic defective particles devoid of viral DNA. Journal of virology. 2013; 87(4): 2011-22. Epub 2012 Dec. 14. doi: 10.1128/JVL02533-12. PubMed PMID: 23236073; PubMed Central PMCID: PMC3571473.

52. Ruiss R, Jochum S, Wanner G, Reisbach G, Hammerschmidt W, Zeidler R. A virus-like particle-based Epstein-Barr virus vaccine. Journal of virology. 2011; 85(24): 13105-13.

53. Speck P, Longnecker R. Epstein-Barr virus (EBV) infection visualized by EGFP expression demonstrates dependence on known mediators of EBV entry. Achieve of Virology. 1999; 144(6): 1123-37. Epub 1999 Aug. 14. PubMed PMID: 10446648.

54. McGinnes L W, Reitter J N, Gravel K, Morrison T G. Evidence for mixed membrane topology of the newcastle disease virus fusion protein. Journal of Virology. 2003; 77(3): 1951-63. Epub 2003 Jan. 15. PubMed PMID: 12525629; PubMed Central PMCID: PMC140911.

55. Biggin M, Farrell P J, Barrell B G. Transcription and DNA sequence of the BamHI L fragment of B95-8 Epstein-Barr virus. EMBO J. 1984; 3(5): 1083-90. Epub 1984 May 1. PubMed PMID: 6203743; PubMed Central PMCID: PMC557577.

56. Ogembo J G, Muraswki M R, McGinnes L W, Parcharidou A, Sutiwisesak R, Tison T, et al. A chimeric EBV gp350/220-based VLP replicates the virion B-cell attachment mechanism and elicits long-lasting neutralizing antibodies in mice. Journal of Translational Medicine. 2015; 13(1): 50.

57. Pantua H D, Mcginnes L W, Peeples M E, Morrison T G. Requirements for the assembly and release of Newcastle disease virus-like particles. Journal of Virology. 2006; 80(22): 11062-73. Epub 2006 Sep. 15. doi: 10.1128/JVL00726-06. PubMed PMID: 16971425; PubMed Central PMCID: PMC1642154.

58. McGinnes L W, Morrison T G. Newcastle Disease Virus-Like Particles: Preparation, Purification, Quantification, and Incorporation of Foreign Glycoproteins. Current Protocols in Microbiology. 2013:18.2. 1-2.21.

59. Laliberte J P, McGinnes L W, Peeples M E, Morrison T G. Integrity of membrane lipid rafts is necessary for the ordered assembly and release of infectious Newcastle disease virus particles. Journal of virology. 2006; 80(21): 10652-62. Epub 2006 Oct. 17. doi: 10.1128/JVL01183-06. PubMed PMID: 17041223; PubMed Central PMCID: PMC1641742.

60. Battisti A J, Meng G, Winkler D C, McGinnes L W, Plevka P, Steven A C, et al. Structure and assembly of a paramyxovirus matrix protein. Proceedings of the National Academy of Sciences. 2012; 109(35): 13996-4000.
61. Ghiran I, Glodek A M, Weaver G, Klickstein L B, Nicholson-Weller A. Ligation of erythrocyte CR1 induces its clustering in complex with scaffolding protein FAP-1. Blood 2008; 112(8): 3465-73. Epub 2008 Aug. 8. doi: blood-2008-04-151845 [pii] 10.1182/blood-2008-04-158145. PubMed PMID: 18684861; PubMed Central PMCID: PMC2569183.
62. Murawski M R, McGinnes L W, Finberg R W, Kurt-Jones E A, Massare M J, Smith G, et al. Newcastle disease virus-like particles containing respiratory syncytial virus G protein induced protection in BALB/c mice, with no evidence of immunopathology. Journal of virology. 2010; 84(2): 1110-23. Epub 2009 Nov. 6. doi: 10.1128/JVL01709-09, PubMed PMID: 19889768; PubMed Central PMCID: PMC2798376.
63. Sashihara J, Burbelo P D, Savoldo B, Pierson T C, Cohen J L. Human antibody titers to Epstein-Barr Virus (EBV) gp350 correlate with neutralization of infectivity better than antibody titers to EBV gp42 using a rapid flow cytometry-based EBV neutralization assay. Virology. 2009; 391(2): 249-56. Epub 2009 Jul. 9. doi: S0042-6822(09)00358-4 [pii] 10.1016/j.virol.2009.06.013. PubMed PMID: 19584018; PubMed Central PMCID: PMC2728425.
64. Pantua H, McGinnes L W, Leszyk J, Morrison T G. Characterization of an alternate form of Newcastle disease virus fusion protein. Journal of virology. 2005; 79(18): 11660-70. Epub 2005 Sep. 6. doi: 10.1128/JVL79.18.11660-11670.2005. PubMed PMID: 16140743; PubMed Central PMCID: PMC1212644.
65. Tanner J, Whang Y, Sample J, Sears A, Kieff E. Soluble gp350/220 and deletion mutant glycoproteins block Epstein-Barr virus adsorption to lymphocytes. Journal of virology. 1988; 62(12): 4452-64. Epub 1988 Dec. 1. PubMed PMID: 2460635; PubMed Central PMCID: PMC253554.
66. Civoli F, Kroenke M A, Reynhardt K, Zhuang Y, Kaliyaperumal A, Gupta S. Development and optimization of neutralizing antibody assays to monitor clinical immunogenicity. Bioanalysis 2012; 4(22): 2725-35. Epub 2012 Dec. 6. doi: 10.4155/bio 12.239, PubMed PMID: 23210655.
67. Gallot G, Vollant S, Saïagh S, Clémenceau B, Viven R, Cerato E, et al. T-cell Therapy Using a Bank of EBV-specific Cytotoxic T Cells: Lessons From a Phase I/II Feasibility and Safety Study. Journal of Immunotherapy. 2014; 37(3): 170-9.
68. Braciale T J, Morrison L A, Sweetser M T, Sambrook J, Gething M J, Braciale V L. Antigen presentation pathways to class I and class II MHC-restricted T lymphocytes. Immunological reviews. 1987; 98:95-114. PubMed PMID: 2443444.
69. Germain R N. Immunology. The ins and outs of antigen processing and presentation. Nature 1986; 322(6081): 687-9. doi: 10.1038/322687a0. PubMed PMID: 3489186.
70. Adhikary D, Behrends U, Feederle R, Delecluse H J, Mautner J. Standardized and highly efficient expansion of Epstein-Barr virus-specific CD4+ T cells by using virus-like particles. Journal of virology, 2008; 82(8): 3903-11. Epub 2008/02/15. doi: 10.1138/JVL0227-07. PubMed PMID: 18272580; PubMed Central PMCID: PMC2293016.
71. Schirmbeck R, Böhm W, Reimann J. Virus-like particles induce MHC class I-restricted T-cell responses. Intervirology. 1996; 39(1-2): 111-9.
72. Paliard X, Liu Y, Wagner R, Wolf H, Baenziger J, Walker C M. Priming of strong, broad, and long-lived HIV type 1 p55gag-specific CD8+ cytotoxic T cells after administration of a virus-like particle vaccine in rhesus macaques. AIDS research and human retroviruses. 2000; 16(3): 273-82.
73. Yajima M, Imadome K, Nakagawa A, Watanabe S, Terashima K, Nakamura H, et al. A new humanized mouse model of Epstein-Barr virus infection that reproduces persistent infection, lymphoproliferative disorder, and cell-mediated and humoral immune responses. The Journal of infectious diseases. 2008; 198(5): 673-82. Epub 2008 Jul. 17. doi: 10.1086/590502. PubMed PMID: 18627269.
74. Chatterjee B, Leung C S, Münz C. Animal models of Epstein-Barr virus infection. Journal of immunological methods, 2014.

Each and every publication and patent mentioned in the above specification is herein incorporated by reference in its entirety for all purposes. Various modifications and variations of the described methods and system of the invention will be apparent to those skilled in the art without departing from the scope and spirit of the invention. Although the invention has been described in connection with specific embodiments, the invention as claimed should not be unduly limited to such specific embodiments. Indeed, various modifications of the described modes for carrying out the invention which are obvious to those skilled in the art and in fields related thereto are intended to be within the scope of the following claims.

We claim:

1. A recombinant virus-like particle (VLP) comprising, in operable combination,
   a) Newcastle disease virus (NDV) matrix (M) protein,
   b) NDV nucleocapsid (NP) protein, and
   c) one or more tumor-associated EBV antigen,
wherein said one or more tumor-associated EBV antigen is fused to the C-terminal end of said NDV NP protein and is inside said VLP.

2. The VLP of claim 1, wherein said tumor-associated EBV antigen is selected from the group consisting of EBNA1, tEBNA1 and LMP2.

3. The VLP of claim 1, wherein said tumor-associated EBV antigen comprises tEBNA1 and LMP2.

4. The VLP of claim 3, further comprising, in operable combination, one or more Epstein-Barr Virus (EBV) antigens, wherein at least one of said one or more antigens is selected from the group consisting of gB, gH, and gL.

5. The VLP of claim 3, wherein said VLP further comprises, in operable combination, EBV gp350/220.

6. The VLP of claim 3, wherein said VLP further comprises, in operable combination, one or more NDV proteins.

7. The VLP of claim 6, wherein said one or more NDV proteins comprise NDV heptad repeat domain 2 (HR2) protein.

8. The VLP of claim 7, wherein said one or more NDV proteins comprise NDV fusion (F) protein.

9. The VLP of claim 8, wherein said one or more NDV proteins comprise NDV heamagglutinin-neuraminidase (HN) protein.

10. The VLP of claim 1, further comprising, in operable combination, one or more human papillomavirus antigens.

11. The VLP of claim 10, wherein said one or more human papillomavirus antigens comprises one or more of L1 and L2.

12. A vaccine comprising the VLP of claim 1 and a physiologically acceptable carrier.

13. An expression vector encoding the recombinant VLP of claim 1.

14. A method for immunizing a mammalian subject against cancer, comprising administering an immunologically effective amount of one or more vaccine of claim 12 to a mammalian subject in need thereof to produce a treated subject, wherein said administering is under conditions to produce an immune response to one or more tumor-associated EBV antigen.

15. The method of claim 14, wherein said cancer comprises an Epstein-Barr Virus (EBV) associated cancer.

16. The method of claim 14, wherein said EBV-associated cancer comprises nasopharyngeal carcinoma.

17. The method of claim 14, wherein said immune response comprises T lymphocytes that specifically bind to said one or more tumor-associated EBV antigen.

18. The method of claim 17, wherein said immune response lacks antibody that specifically binds to said one or more tumor-associated EBV antigen.

19. The method of claim 17, wherein said T lymphocytes are selected from $CD4^+$ lymphocytes and $CD8^+$ lymphocytes.

20. The method of claim 14, wherein said method further comprises administering a recombinant VLP that contains, in operable combination,
   a) Newcastle disease virus (NDV) matrix (M) protein, and
   b) EBV gp350/220.

21. The method of claim 14, wherein said method further comprises one or more of
   a) detecting said immune response to said one or more tumor-associated EBV antigen, and
   b) detecting a reduction in one or more symptoms of said cancer in said treated subject.

22. The method of claim 14, wherein said administering is before manifestation of one or more symptoms of said cancer.

23. The method of claim 14, wherein said administering is after manifestation of one or more symptoms of said cancer.

* * * * *